(12) United States Patent
van der Heijden et al.

(10) Patent No.: US 10,889,822 B2
(45) Date of Patent: Jan. 12, 2021

(54) CONSTRUCT AND SEQUENCE FOR ENHANCED GENE EXPRESSION

(71) Applicant: PROTEONIC BIOTECHNOLOGY IP B.V., Leiden (NL)

(72) Inventors: Maurice Wilhelmus van der Heijden, Gouda (NL); Bart Marinus Engels, Woerden (NL)

(73) Assignee: Proteonic Biotechnology IP BV

( * ) Notice: Subject to any disclaimer, the term of this patent is extended or adjusted under 35 U.S.C. 154(b) by 0 days.

(21) Appl. No.: 15/109,301

(22) PCT Filed: Dec. 24, 2014

(86) PCT No.: PCT/NL2014/050907
§ 371 (c)(1),
(2) Date: Jun. 30, 2016

(87) PCT Pub. No.: WO2015/102487
PCT Pub. Date: Jul. 9, 2015

(65) Prior Publication Data
US 2017/0029826 A1 Feb. 2, 2017

(30) Foreign Application Priority Data

Dec. 31, 2013 (EP) ...................................... 13199873
Dec. 31, 2013 (EP) ...................................... 13199875

(51) Int. Cl.
| | | |
|---|---|---|
| *C07H 21/04* | (2006.01) | |
| *C12N 15/00* | (2006.01) | |
| *C12N 15/63* | (2006.01) | |
| *C12N 15/67* | (2006.01) | |
| *C07K 16/00* | (2006.01) | |
| *A61K 39/395* | (2006.01) | |
| *A61K 48/00* | (2006.01) | |
| *C07K 16/24* | (2006.01) | |
| *C12N 15/85* | (2006.01) | |
| *C12P 21/00* | (2006.01) | |

(52) U.S. Cl.
CPC .......... *C12N 15/67* (2013.01); *A61K 39/3955* (2013.01); *A61K 48/0066* (2013.01); *C07K 16/00* (2013.01); *C07K 16/241* (2013.01); *C12N 15/85* (2013.01); *C12P 21/005* (2013.01); *C07K 2317/14* (2013.01); *C07K 2317/21* (2013.01); *C07K 2317/24* (2013.01); *C07K 2317/51* (2013.01); *C07K 2317/515* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,547,862 | A * | 8/1996 | Meador | C12N 15/70 435/320.1 |
| 6,063,598 | A * | 5/2000 | Enenkel | C07K 14/47 435/320.1 |
| 6,368,825 | B1 * | 4/2002 | Chao | C12N 15/86 435/235.1 |
| 9,284,588 | B2 * | 3/2016 | Merino | C12N 9/0065 |
| 2005/0101017 | A1 * | 5/2005 | Auerbach | C12N 15/8509 435/455 |
| 2009/0203071 | A1 * | 8/2009 | Chen | |
| 2012/0183955 | A1 * | 7/2012 | Rao | A61K 48/00 435/6.1 |
| 2013/0281516 | A1 * | 10/2013 | Gao | C12N 15/1137 514/44 R |
| 2013/0298263 | A1 * | 11/2013 | Iwawaki | C07K 14/82 800/3 |

OTHER PUBLICATIONS

Li et al. Usage of an intronic promoter for stable gene expression in *Saccharomyces cerevisiae*. Letters in Applied Microbiology 40: 347-352, 2005.*
Zauberman et al. A functional p53-responsive intronic promoter is contained within the human mdm2 gene. Nucleic Acids Res. 23: 2584-2592, 1995.*
Kolb, A. The first intron of the murine beta-casein gene contains a functional promoter. Biochem. Biophys. Res. Commun. 306:1099-1105, 2003.*
Alam et al. Lung surfactant protein B promoter function is dependent on the helical phasing, orientation and combinatorial action of cis-DNA elements. Gene 282:103-111, 2002.*
Muller et al. Repression of lac promoter as a function of distance, phase and quality of an auxiliary lac operator. J. Mol. Biol. 257:21-29, 1996.*
Xie et al. Domains of the rat rDNA promoter must be aligned stereospecifically. Mol. Cell. Biol. 12:1266-1275, 1992.*
Chapman et al. Effect of intron A from human cytomegalovirus (Towne) immediate-early gene on heterologous expression in mammalian cells. Nucleic Acids Res. 19:3979-3986, (Year: 1991).*
Schorpp et al. The human ubiquitin C promoter directs high ubiquitous expression of transgenes in mice. Nucleic Acids Research 24:1787-1788, (Year: 1996).*
Lo et al. Novel baculovirus DNA elements strongly stimulate activities of exogenous and endogenous promoters. J. Biol. Chem. 277:5256-5264, (Year: 2002).*

(Continued)

*Primary Examiner* — Quang Nguyen
(74) *Attorney, Agent, or Firm* — McDonnell Boehnen Hulbert & Berghoff LLP

(57) ABSTRACT

The invention relates to a method for transcription and expression using a nucleic acid construct which is characterized by the presence of a promoter followed by an intronic promoter. The invention further relates to the nucleic acid construct, an expression vector and a cell comprising the construct, and its use. The invention also relates to methods for transcription and optionally expression using a nucleotide sequence. The invention further relates to the nucleotide sequence and a construct, expression vector and cell comprising the nucleotide sequence, and its use.

9 Claims, 11 Drawing Sheets

Figure 1:
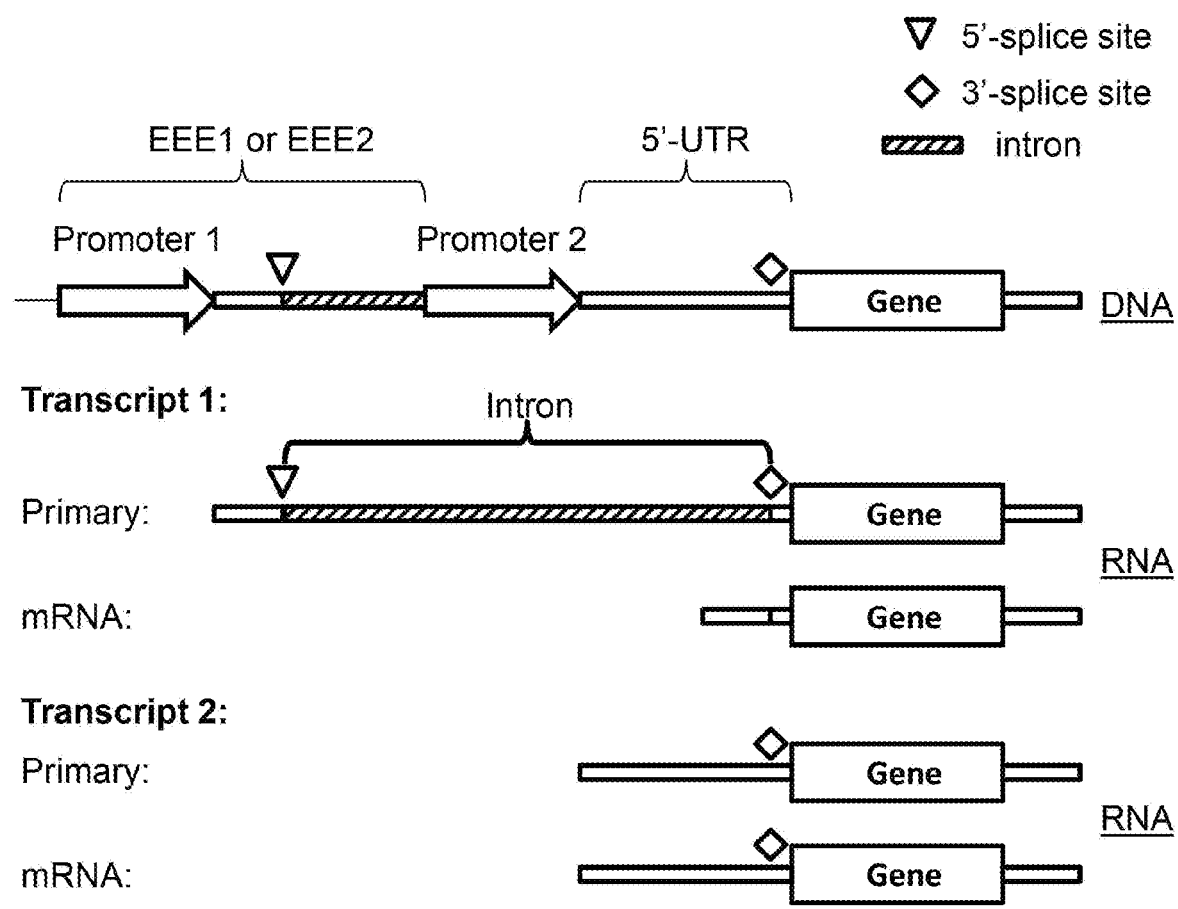

Specification includes a Sequence Listing.

(56) References Cited

OTHER PUBLICATIONS

Lee et al. A baculovirus superinfection system: Efficient vehicle for gene transfer into *Drosophila* S2 cells. J. Virology 74:11873-11880, (Year: 2000).*

Angelichio et al. Comparison of several promoters and polyadenylation signals for use in heterologous gene expression in cultured *Drosophila* cells. Nucleic Acids Research 19:5037-5043, (Year: 1991).*

Christensen, Alan H. et al., Ubiquitin promoter-based vectors for high-level expression of selectable and/or screenable marker genes in monocotyledonous plants, Transgenic Research, vol. 5, No. 3, 1996, pp. 213-218.

Sivamani, Elumalai et al., Expression enhancement of a rice polyubiquitin gene promoter, Plant Molecular Biology, Kluwer Academic Publishers, Dordrecht, NL, vol. 60, No. 2, Jan. 1, 2006, pp. 225-239.

Bianchi, Marzia et al., Yin Yang 1 Intronic Binding Sequences and Splicing Elicit Intron-Mediated Enhancement of Ubiquitin C Gene Express, PLOS One, vol. 8, No. 6, Jun. 12, 2013, e65932, 19 pages.

Nenoi, M. et al., Comparison of the 5' upstream region of the evolutionarily equivalent polyubiquitin gene of humans and Chinese hamsters, Gene, Elsevier, Amsterdam, NL, vol. 179, No. 2, Nov. 14, 1996, pp. 297-299.

Nenoi, M. et al., Novel structure of a Chinese hamster polyubiquitin gene, Biochimica et Biophysica Acta, Elsevier, NL, vol. 1204, No. 2, Jan. 1, 1994, pp. 271-278.

* cited by examiner

Reference vector

TEE vector

SEQUENCE LISTING

```
<160> NUMBER OF SEQ ID NOS: 88

<210> SEQ ID NO 1
<211> LENGTH: 1449
<212> TYPE: DNA
<213> ORGANISM: Artificial sequence
<220> FEATURE:
<223> OTHER INFORMATION: EEE1

<400> SEQUENCE: 1
tttcaggcaa ccagagctac atagtgagat cctgtctcaa caaaaataaa ataatctaag        60
gcttcaaagg gttcaatctc ttaggtagct aaatatgaac aaaatttggg aaatgtgacc       120
ttttccttag tgacagtcag atagaacctt ctcgagtgca aggacaccaa gtgcaaacag       180
gctcaagaac agcctggaaa ggtctagtgc tatggggctt caggtcgaat gccaactgtt       240
ttcaagaact gtgtggattt ttctgcctgt aacgaattca gattcattt tcaaaactcg       300 gggagagttt tcccccttta taattttttt tttaaattta ttaaactttg tttcgttccc       360
cttgttttga gaattgcaga gtcatccacc ctgtcacagt gccagggagc tcagggatgg       420
gcccaggggc ctggcggggc tgaagggact ggggaagcga gggctccaaa gggaccccag       480
tgtggcagga gccaaagccc taggtcccta gaacgcagag gccaccggga cccccagac       540 ggggtaagcg ggtgggtgtc tggggcgcga agccgcactg cgcatgcgcc gaggtccgct       600
ccggccgcgc tgatccaagc cgggttctcg cgccgacctg gtcgtgattg acaagtcaca       660
cacgctgatc cctccgcggg gccgcacagg gtcacagcct ttccctcc cacaaagccc       720 cctactctct gggcaccaca cacgaacatt ccttgagcgt gaccttgttg gctctagtca       780
ggcgcctccg gtgcagagac tggaacggcc ttgggaagta gtccctaacc gcatttccgc       840
```

```
ggagggatcg tcgggagggc gtggcttctg aggattatat aaggcgactc cgggcgggtc    900
ttagctagtt ccgtcggaga cccgagttca gtcgccgctt ctctgtgagg actgctgccg    960
ccgccgctgg tgaggagaag ccgccgcgct tggcgtagct gagagacggg gaggggcgc    1020 ggacacgagg ggcagcccgc ggcctggacg ttctgtttcc gtggcccgcg aggaaggcga   1080
ctgtcctgag gcggaggacc cagcggcaag atggcggcca agtggaagcc tgagggata    1140 ggcgagcggc cctgaggcgc tcgacgtgggt tgggggggaa gcaggcccgc gaggcagctg   1200
cagccgggaa cgtgcggcca acccttatt tttttgacg ggttgcgggc cgtaggtgcc    1260
tccgaagtga gagccgtggg cgtttgactg tcgggagagg tcggtcggat tttcatccgt   1320
tgctaaagac ggaagtgcga ctgagacggg aagggggggg agtcggttgg tggcggttga   1380
acctggacta aggcgcacat gacgtcgcgg tttctatggg ctcataatgg gtggtgagga   1440
catttccct                                                           1449

<210> SEQ ID NO 2
<211> LENGTH: 1228
<212> TYPE: DNA
<213> ORGANISM: Artificial sequence
<220> FEATURE:
<223> OTHER INFORMATION: EEE2

<400> SEQUENCE: 2
gtaaagcaga tcacacagaa tatggcacac ttgagcactt gatgtgtact acattactct     60
tagtgacgac tttaattatc gtgcgcattc ccagcgcttc ctatggtgcc caacacagag    120
cggacgccta gagacaattt tggggggatgg ggcagatgct ctgcctcggg aaaaaaaaag    180
cacacctgcc ctgacgttgg tggctgggtc tggaagatac gtggaaatta agctaaggat    240
gtgtggcttc cagatcaaaa accgcaaaaa tctaacgccg tgactactga ctacggtcag    300
agagcacaga ctggagcaac ctctcacggc ctgggctgtc tgcgcgtgcg tgagccagaa    360
acccgagggg ctccctgggc ccgccctatc gatcgacccg atcggggatc gtcagcttgg    420
ttctggccac agaggttgct cttctcgcga tgcttcagac ctggcggcag ggaaagggtg    480
ggctaattgg agagccagga agagcgtgag gcggccccac gctgctttcc cagaaggctg    540
tgcgtgctcc tcgcttcctc cgcggtcttc cgagcggtcg cgtgaactgc ttccagcagg    600
ctggccatgg cgcttcacgt tcccaaggct ccgggctttg cccagatgct caaggaggga    660
gcgaaagtaa gggctgaagg aaaggaatga ggtgggagcg tcagcatagg gctgcggcgg    720
cggcggcgaa gtaggagggc ctactaacgg gctgagcgtg ctgccctggc tcagcggccg    780
ggggaagaga agattccaga aagggaggtg attttggaag ggctcggcca ccggagcctg    840
cgggcacttc tcttcttccg cgaccgggag aaggccgagg gatcggcggc acgatcgaca    900
ttgtacacct tgaaggtgga cggatgtgaa gccgcgcgtg cgttttgcct ccatccgtaa    960
atggggctaa ggcccgtcac ccttaaagga ggttgtgagg gtgaaattga ataacgtaga   1020
tgaaattgtc ttgagaactg cgacgtcgat tatcacatag ctcgcgagtt gtaggatggg   1080
gaagaacgag aactagccga tccagagaag agagtgggaa aaagggccgg gtcttggttg   1140
cttgcttccc agtgagaaac atacggcttt cagcttagtt gacagaagcc atgcgttgta   1200
gccaaatgag ttccggtccc aacttatg                                      1228

<210> SEQ ID NO 3
<211> LENGTH: 173
<212> TYPE: DNA
<213> ORGANISM: Artificial sequence
```

```
<220> FEATURE:
<223> OTHER INFORMATION: TEE

<400> SEQUENCE: 3
caagctctag caggaagaag aaataagaag aagaagaaga agaagaagaa gcgtctcctc      60
ttcttcttgt gagagtaaaa aataaaactc ccaaaaaaaa gaaaatcatc aaaaaaacaa     120
atttcaaaaa gagttttgt gtttggggat taaagaataa aaaaaacaac gtc             173

<210> SEQ ID NO 4
<211> LENGTH: 175
<212> TYPE: DNA
<213> ORGANISM: Artificial sequence
<220> FEATURE:
<223> OTHER INFORMATION: TEE

<400> SEQUENCE: 4
caagctctag caggaagaag aaataagaag aagaagaaga agaagaagaa gcgtctcctc      60
ttcttcttgt gagagtaaaa aataaaactc ccaaaaaaaa gaaaatcatc aaaaaaacaa     120
atttcaaaaa gagttttgt gtttggggat taaagaataa aaaaaacaac gtccc           175

<210> SEQ ID NO 5
<211> LENGTH: 189
<212> TYPE: DNA
<213> ORGANISM: Artificial sequence
<220> FEATURE:
<223> OTHER INFORMATION: TEE

<400> SEQUENCE: 5
agatcactag aagcttcaag ctctagcagg aagaagaaat aagaagaaga agaagaagaa      60
gaagaagcgt ctcctcttct tcttgtgaga gtaaaaaata aaactcccaa aaaaagaaaa     120
atcatcaaaa aacaaatttt caaaaagagt ttttgtgttt ggggattaaa gaataaaaaa     180
aacaacgcc                                                             189

<210> SEQ ID NO 6
<211> LENGTH: 189
<212> TYPE: DNA
<213> ORGANISM: Artificial sequence
<220> FEATURE:
<223> OTHER INFORMATION: TEE

<400> SEQUENCE: 6
agatcactag aagcttcaag ctctagcagg aagaagaaag aagaagaaga agaagaagaa      60
gaagaagcgt ctcctcttct tcttgtgaga gtaaaaaaga aaactcccaa aaaaagaaaa     120
atcatcaaaa aacaaattt caaaaagagt ttttgtgttt ggggattaaa gaagaaaaaa     180
aacaacgcc                                                             189

<210> SEQ ID NO 7
<211> LENGTH: 191
<212> TYPE: DNA
<213> ORGANISM: Artificial sequence
<220> FEATURE:
<223> OTHER INFORMATION: TEE

<400> SEQUENCE: 7
agatcactag aagcttcaag ctctagcagg aagaagaaat aagaagaaga agaagaagaa      60
gaagaagcgt ctcctcttct tcttgtgaga gtaaaaaata aaactcccaa aaaaagaaaa     120
atcatcaaaa aacaaatttt caaaaagagt ttttgtgttt ggggattaaa gaataaaaaa     180
```

```
aacaacaggc c                                                      191

<210> SEQ ID NO 8
<211> LENGTH: 284
<212> TYPE: DNA
<213> ORGANISM: Artificial sequence
<220> FEATURE:
<223> OTHER INFORMATION: TEE

<400> SEQUENCE: 8 cttttttcgca acgggtttgc cgccagaaca caggtgtcgt gaggaattag cttggtacta    60
atacgactca ctatagggag acccaagctg gctaggtaag cttggtaccc aagctctagc   120
aggaagaaga aataagaaga agaagaagaa gaagaagaag cgtctcctct tcttcttgtg   180
agagtaaaaa ataaaactcc caaaaaaaag aaaatcatca aaaaaacaaa tttcaaaaag   240 agttttgtg tttggggatt aaagaataaa aaaaacaacg tccc                     284

<210> SEQ ID NO 9
<211> LENGTH: 230
<212> TYPE: DNA
<213> ORGANISM: Artificial sequence
<220> FEATURE:
<223> OTHER INFORMATION: TEE

<400> SEQUENCE: 9
aacccactgc ttactggctt atcgaaatta atacgactca ctatagggag acccaagctc    60
tagcaggaag aagaaataag aagaagaaga agaagaagaa gaagcgtctc ctcttcttct   120
tgtgagagta aaaaataaaa ctcccaaaaa aagaaaatc atcaaaaaaa caaatttcaa   180
aaagagtttt tgtgtttggg gattaaagaa taaaaaaaac aacctccacc               230

<210> SEQ ID NO 10
<211> LENGTH: 177
<212> TYPE: DNA
<213> ORGANISM: Artificial sequence
<220> FEATURE:
<223> OTHER INFORMATION: TEE

<400> SEQUENCE: 10
caagctctag cagcaacaac aaataacaac aacaacaaca acaacaacaa gcgtctcctc    60
ttcttcttgt gagagtaaaa aataaaactc ccaaaaaaaa gaaaatcatc aaaaaaacaa   120
atttcaaaaa gagttttgt gtttggggat taaagaataa aaaaaacaac ctccacc        177

<210> SEQ ID NO 11
<211> LENGTH: 191
<212> TYPE: DNA
<213> ORGANISM: Artificial sequence
<220> FEATURE:
<223> OTHER INFORMATION: TEE

<400> SEQUENCE: 11
agatcactag aagcttcaag ctctagcagg aagaagaaat aagaagaaga agaagaataa    60
gaagaagcgt ctcgtcttct tcttgtgaga gtaaaaaata aaactcccaa aaaaataaa   120 atcatcaaaa aaagaaattt caaaagagt ttttgtgttt ggggattaaa gaataaaaaa   180
aacaacaggc c                                                        191

<210> SEQ ID NO 12
<211> LENGTH: 189
<212> TYPE: DNA
<213> ORGANISM: Artificial sequence
```

```
<220> FEATURE:
<223> OTHER INFORMATION: TEE

<400> SEQUENCE: 12
agatcactag aagcttcaag ctctagcagg aagaagaaat aataagaaga agaagaataa      60
gaagaagcgt ctcctcttct tcttgtgaga gtaaaaaata aaactcccaa aaaaaataaa     120
atcatcaaaa aaataaattt caaaagagt ttttgtgttt ggggattaaa gaataaaaaa      180
aacaacgcc                                                             189

<210> SEQ ID NO 13
<211> LENGTH: 173
<212> TYPE: DNA
<213> ORGANISM: Artificial sequence
<220> FEATURE:
<223> OTHER INFORMATION: TEE

<400> SEQUENCE: 13
caagctctag caggaagaag aaakaagaag aagaagaaga agaagaagaa gcgtctcctc      60
ttcttcttgt gagagtaaaa aakaaaactc ccaaaaaaaa kaaaatcatc aaaaaaacaa     120
atttcaaaaa gagttttgt gtttggggat taaagaakaa aaaaaacaac gtc             173

<210> SEQ ID NO 14
<211> LENGTH: 274
<212> TYPE: DNA
<213> ORGANISM: Artificial sequence
<220> FEATURE:
<223> OTHER INFORMATION: UN2

<400> SEQUENCE: 14
caagctctag caggaagaag aaakaagaag aagaagaaga agaagaagaa gcgtctcctc      60
ttcttcttgt gagagtaaaa aakaaaactc ccaaaaaaaa kaaaatcatc aaaaaaacaa     120
atttcaaaaa gagttttgt gtttggggat taaagaakaa aaaaaacaac aggtgagtaa     180
gcgcagttgt cgtctcttgc ggtgccgttg ctggttctca cccttttag gtctgttctc     240 gtcttccgtt ctgactctct ctttttcgtt gcag                                 274

<210> SEQ ID NO 15
<211> LENGTH: 123
<212> TYPE: DNA
<213> ORGANISM: Artificial sequence
<220> FEATURE:
<223> OTHER INFORMATION: UN1dGAA

<400> SEQUENCE: 15
ggcgtctcct cttcttcttg tgagagtaaa aaataaaact cccaaaaaaa akaaaatcat      60
caaaaaaaca aatttcaaaa agagttttg tgtttgggga ttaaagaaka aaaaaacaac     120
gtc                                                                   123

<210> SEQ ID NO 16
<211> LENGTH: 257
<212> TYPE: DNA
<213> ORGANISM: Artificial sequence
<220> FEATURE:
<223> OTHER INFORMATION: UN2dGAA

<400> SEQUENCE: 16
aaagtatcaa caaaaagct tcgtctcctc ttcttcttgt gagagtaaaa aakaaaactc       60
ccaaaaaaaa kaaaatcatc aaaaaaacaa atttcaaaaa gagttttgt gtttgtaagt    120
```

```
caggactcta gctttctact gtagtatcct ctaaaggact gctgttctgt gcacccccctt      180 cctttgttta tcatagcgca cgacaagagt actaactaat taacttaggg ggattaaaga       240
akaaaaaaaa caacaaa                                                     257
```

<210> SEQ ID NO 17
<211> LENGTH: 173
<212> TYPE: DNA
<213> ORGANISM: Artificial sequence
<220> FEATURE:
<223> OTHER INFORMATION: R3

<400> SEQUENCE: 17

```
caagctctag cacgtctcct cttcttcttg tgagagtaaa aaakaaaact cccaaaaaaa       60
akaaaatcat caaaaaaaca aatttcaaaa agagtttttg tgtttgggga ttaaagaaka       120
aaaaaaacaa ggaagaagaa akaagaagaa gaagaagaag aagaagaagc ctc             173
```

<210> SEQ ID NO 18
<211> LENGTH: 384
<212> TYPE: DNA
<213> ORGANISM: Artificial sequence
<220> FEATURE:
<223> OTHER INFORMATION: fUN1

<400> SEQUENCE: 18

```
caagctctag caggaagaag aaataagaag aagaagaaga agaagaagaa gcgtctcctc       60
ttcttcttgt gagagtaaaa aataaaactc ccaaaaaaaa gaaaatcatc aaaaaaacaa       120
atttcaaaaa gagttttttgt gtttggggat taaagaataa aaaaaacaac gtctggacaa     180
accacaacta gaatgcagtg aaaaaaatgc tttatttgtg aaatttgtga tgctattgct      240
ttatttgtaa ccattataag ctgcaataaa caagttaaca acaacaattg cattcatttt     300
atgtttcagg ttcaggggga ggtgtgggag gttttttaaa gcaagtaaaa cctctacaaa     360
tgtggtaaaa tcgataagga tccg                                            384
```

<210> SEQ ID NO 19
<211> LENGTH: 277
<212> TYPE: DNA
<213> ORGANISM: Artificial sequence
<220> FEATURE:
<223> OTHER INFORMATION: UN2-2

<400> SEQUENCE: 19

```
caagctctag caggaagaag aaakaagaag aagaagaaga agaagaagaa gcgtctcctc       60
ttcttcttgt gagagtaaaa aakaaaactc ccaaaaaaaa gaaaatcatc aaaaaaacaa       120
atttcaaaaa gagttttttgt gtttggggat taaagaagaa aaaaaacaac aggtgagtaa     180
gcgcagttgt cgtctcttgc ggtgccgttg ctggttctca cacctttag gtctgttctc      240 gtcttccgtt ctgactctct cttttttcgtt gcaggcc                              277
```

<210> SEQ ID NO 20
<211> LENGTH: 252
<212> TYPE: DNA
<213> ORGANISM: Artificial sequence
<220> FEATURE:
<223> OTHER INFORMATION: UN2-3

<400> SEQUENCE: 20

```
aagctctagc aggaagaaga aakaagaaga agaagaagaa gaagaagaag cgtctcctct       60
tcttcttgtg agagtaaaaa akaaaactcc caaaaaaaak aaaatcatca aaaaaacaaa      120
```

-continued

```
tttcaaaaag agtaggtaag attatctctt cccaaaattg attactttt  tattgaacaa    180 ttattaacca atcatggctt aacgaaaaac aggttttgtg tttggggatt aaagaakaaa    240
aaaaacaaaa ca                                                        252
```

<210> SEQ ID NO 21
<211> LENGTH: 254
<212> TYPE: DNA
<213> ORGANISM: Artificial sequence
<220> FEATURE:
<223> OTHER INFORMATION: UN2-4

<400> SEQUENCE: 21

```
caagctctag caggaagaag aaakaagaag aagaagaaga agaagaagaa gcgtctcctc    60
ttcttcttgt gagagtaaaa aakaaaactc ccaaaaaaaa kaaatcatc  aaaaaaacaa   120 atttcaaaaa gagtaggtaa gattatctct tcccaaaatt gattactttt attattgaac   180
aattactaac atttcatggc ttaacgaaaa acaggttttg tgtttgggga ttaaagaaka   240
aaaaaaacaa aaca                                                     254
```

<210> SEQ ID NO 22
<211> LENGTH: 266
<212> TYPE: DNA
<213> ORGANISM: Artificial sequence
<220> FEATURE:
<223> OTHER INFORMATION: UN2-5

<400> SEQUENCE: 22

```
caagctctag caggaagaag aaakaagaag aagaagaaga agaagaagaa gcgtctcctc    60
ttcttcttgt gagagtaaaa aakaaaactc ccaaaaaaaa kaaatcatc  aaaaaaacaa   120 atttcaaaaa gagtgaggta agattatcga tatttaaatt atttatttct tcttttccat   180 tttttggct  aacattttcc atggttttat gatatcatgc aggtacgttt tgtgtttggg   240
gattaaagaa kaaaaaaaac aaaaca                                        266
```

<210> SEQ ID NO 23
<211> LENGTH: 266
<212> TYPE: DNA
<213> ORGANISM: Artificial sequence
<220> FEATURE:
<223> OTHER INFORMATION: UN2-6

<400> SEQUENCE: 23

```
caagctctag caggaagaag aaakaagaag aagaagaaga agaagaagaa gcgtctcctc    60
ttcttcttgt gagagtaaaa aakaaaactc ccaaaaaaaa kaaatcatc  aaaaaaacaa   120 atttcaaaaa gagtgaggta agattatcga tatttaaatt atttatttct tcttttccat   180 tttttggct  aacattttcc taggttttat tatatctagc aggtacgttt tgtgtttggg   240
gattaaagaa kaaaaaaaac aaaaca                                        266
```

<210> SEQ ID NO 24
<211> LENGTH: 265
<212> TYPE: DNA
<213> ORGANISM: Artificial sequence
<220> FEATURE:
<223> OTHER INFORMATION: UN2-7

<400> SEQUENCE: 24

```
aagctctagc aggaagaaga aakaagaaga agaagaagaa gaagaagaag cgtctcctct    60
```

| | |
|---|---|
| tcttcttgtg agagtaaaaa akaaaactcc caaaaaaaak aaaatcatca aaaaaacaaa | 120 |
| tttcaaaaag agtgaggtaa gattatcgat atttaaatta tttatttctt cttttccatt | 180 |
| tttttggcta acattttcct aggttttatt atatctagca ggtacgtttt gtgtttgggg | 240 |
| attaaagaak aaaaaaaaca aaaca | 265 |

<210> SEQ ID NO 25
<211> LENGTH: 266
<212> TYPE: DNA
<213> ORGANISM: Artificial sequence
<220> FEATURE:
<223> OTHER INFORMATION: UN2-8

<400> SEQUENCE: 25

| | |
|---|---|
| caagctctag caggaagaag aaakaagaag aagaagaaga agaagaagaa gcgtctcctc | 60 |
| ttcttcttgt gagagtaaaa akaaaactc ccaaaaaaaa kaaaatcatc aaaaaaacaa | 120 |
| atttcaaaaa gagtgaggta agattatcga tatttaaatt atttatttct tcttttccat | 180 |
| ttttttggct aacattttcc taggttttat tatatctagc aggtacgttt tgtgtttggg | 240 |
| gattaaagaa kaaaaaaaac aaaacc | 266 |

<210> SEQ ID NO 26
<211> LENGTH: 287
<212> TYPE: DNA
<213> ORGANISM: Artificial sequence
<220> FEATURE:
<223> OTHER INFORMATION: UN2-9

<400> SEQUENCE: 26

| | |
|---|---|
| caagctctag caggaagaag aaakaagaag aagaagaaga agaagaagaa gcgtctcctc | 60 |
| ttcttcttgt gagagtaaaa akaaaactc ccaaaaaaaa kaaaatcatc aaaaaaacaa | 120 |
| atttcaaaaa gagttttgt gtttgtaagt caggactcta gctttctact gtagtatcct | 180 |
| ctaaaggact gctgttctgt gcacccccctt cctttgttta tcatagcgca cgacaagagt | 240 |
| actaactaat taacttaggg ggattaaaga akaaaaaaaa caacaaa | 287 |

<210> SEQ ID NO 27
<211> LENGTH: 251
<212> TYPE: DNA
<213> ORGANISM: Artificial sequence
<220> FEATURE:
<223> OTHER INFORMATION: UN2-10

<400> SEQUENCE: 27

| | |
|---|---|
| caagctctag caggaagaag aaakaagaag aagaagaaga agaagaagaa gcgtctcctc | 60 |
| ttcttcttgt gagagtaaaa akaaaactc ccaaaaaaaa kaaaatcatc aaaaaaacaa | 120 |
| atttcaaaaa gagttttgt gtttgggtaa gtaattgcct tactcggaaa ataatcaatc | 180 |
| atcatactaa cgcaagaggc gctgatattg cggttataca gggattaaag aakaaaaaaa | 240 |
| acaacgtcac c | 251 |

<210> SEQ ID NO 28
<211> LENGTH: 143
<212> TYPE: DNA
<213> ORGANISM: Artificial sequence
<220> FEATURE:
<223> OTHER INFORMATION: UN1dGAA-2

<400> SEQUENCE: 28

| | |
|---|---|
| aaagtatcaa caaaaaagct tcgtctcctc ttcttcttgt gagagtaaaa akaaaactc | 60 |

```
ccaaaaaaaa kaaaatcatc aaaaaaacaa atttcaaaaa gagtttttgt gtttggggat      120
taaagaakaa aaaaaacaac aaa                                             143

<210> SEQ ID NO 29
<211> LENGTH: 123
<212> TYPE: DNA
<213> ORGANISM: Artificial sequence
<220> FEATURE:
<223> OTHER INFORMATION: UN1dGAA-3

<400> SEQUENCE: 29
tcgtctcctc ttcttcttgt gagagtaaaa aakaaaactc ccaaaaaaaa kaaaatcatc      60
aaaaaaacaa atttcaaaaa gagtttttgt gtttggggat taaagaakaa aaaaaacaac     120
gtc                                                                  123

<210> SEQ ID NO 30
<211> LENGTH: 134
<212> TYPE: DNA
<213> ORGANISM: Artificial sequence
<220> FEATURE:
<223> OTHER INFORMATION: UN1dGAA-4

<400> SEQUENCE: 30
caagctctag cacgtctcct cttcttcttg tgagagtaaa aaakaaaact cccaaaaaaa      60
akaaaatcat caaaaaaaca aatttcaaaa agagttttgt gtttgggga ttaaagaaka     120 aaaaaaacaa cgcc                                                      134

<210> SEQ ID NO 31
<211> LENGTH: 140
<212> TYPE: DNA
<213> ORGANISM: Artificial sequence
<220> FEATURE:
<223> OTHER INFORMATION: UN1dGAA-5

<400> SEQUENCE: 31
ggcaagctct agcacgtctc ctcttcttct tgtgagagta aaaakaaaa ctcccaaaaa       60 aaakaaaatc atcaaaaaaa caaatttcaa aaagagtttt tgtgtttggg gattaaagaa    120
kaaaaaaaac aacctccacc                                                140

<210> SEQ ID NO 32
<211> LENGTH: 130
<212> TYPE: DNA
<213> ORGANISM: Artificial sequence
<220> FEATURE:
<223> OTHER INFORMATION: UN1dGAA-6

<400> SEQUENCE: 32
caagcgtctc ctcttcttct tgtgagagta aaaakaaaa ctcccaaaaa aaakaaaatc       60
atcaaaaaaa caaatttcaa aaagagtttt tgtgtttggg gattaaagaa kaaaaaaaac    120
aacctccacc                                                           130

<210> SEQ ID NO 33
<211> LENGTH: 178
<212> TYPE: DNA
<213> ORGANISM: Artificial sequence
<220> FEATURE:
<223> OTHER INFORMATION: UN2dGAA-2

<400> SEQUENCE: 33
```

```
cgtctcctct tcttcttgtg agagtaaaaa akaaaactcc caaaaaaaak aaaatcatca    60
aaaaaacaaa tttcaaaaag agttttgtg tttggggatt aaagaakaaa aaaaacaacc   120
tcgtgcgtgt tgccgattcg cgtacgaata cgccttgtgc tgacacttct gtagcacc    178
```

<210> SEQ ID NO 34
<211> LENGTH: 238
<212> TYPE: DNA
<213> ORGANISM: Artificial sequence
<220> FEATURE:
<223> OTHER INFORMATION: UN2dGAA-3

<400> SEQUENCE: 34

```
caagctctag cacgtctcct cttcttcttg tgagagtaaa aakaaaact cccaaaaaaa    60 akaaaatcat caaaaaaaca aatttcaaaa agagttttg tgtttggga ttaaagaaka   120 aaaaaaacaa caggtgagta agcgcagttg tcgtctcttg cggtgccgtt gctggttctc   180 acaccttta ggtctgttct cgtcttccgt tctgactctc tcttttttcgt tgcaggcc    238
```

<210> SEQ ID NO 35
<211> LENGTH: 229
<212> TYPE: DNA
<213> ORGANISM: Artificial sequence
<220> FEATURE:
<223> OTHER INFORMATION: UN2dGAA-4

<400> SEQUENCE: 35

```
atcaagctct agcacgtctc ctcttcttct tgtgagagta aaaakaaaa ctcccaaaaa    60 aaakaaaatc atcaaaaaaa caaatttcaa aaagagtgag gtaagattat cgatattta   120 attatttatt tcttcttttc cattttttg gctaacattt tcctaggttt tattatatct   180
agcaggtacg ttttgtgttt ggggattaaa gaakaaaaaa aacaaaaca              229
```

<210> SEQ ID NO 36
<211> LENGTH: 188
<212> TYPE: DNA
<213> ORGANISM: Artificial sequence
<220> FEATURE:
<223> OTHER INFORMATION: UN1shuffle

<400> SEQUENCE: 36

```
caagctctag cacgtctcct cttcttcttg tgagagtaaa aakaaaact cccaaaaaaa    60 akaaaatcat caaaaaaaca aatttcaaaa agagttttg tgtttgggga ttaaagaaka   120
aaaaaaacaa ggaagaagaa akaagaagaa gaagaagaag aagaagaagg gcggccgccc   180
ccttcacc                                                            188
```

<210> SEQ ID NO 37
<211> LENGTH: 173
<212> TYPE: DNA
<213> ORGANISM: Artificial sequence
<220> FEATURE:
<223> OTHER INFORMATION: UN1shuffle-2

<400> SEQUENCE: 37

```
caagctctag cacgtctcct cttcttcttg tgagagtaaa aakaaaact cccaaaaaaa    60 akaaaatcat caaaaaaaca aatttcaaaa agagttttg tgtttgggga ttaaagaaka   120
aaaaaaacaa ggaagaagaa akaagaagaa gaagaagaag aagaagaagc gcc         173
```

<210> SEQ ID NO 38
<211> LENGTH: 154

```
<212> TYPE: DNA
<213> ORGANISM: Artificial sequence
<220> FEATURE:
<223> OTHER INFORMATION: UN1shuffle-3

<400> SEQUENCE: 38
gaagctctag cacgtctcct cttcttcttg tgagagtaaa aaakaaaact cccaaaaaaa    60
akaaaatcat caaaaaaaca aatttcaaaa agagttttttg tgtttgggga ttaaagaaka    120
aaaaaaacaa ggaagaagaa gaagaagaag cgcc                                154

<210> SEQ ID NO 39
<211> LENGTH: 179
<212> TYPE: DNA
<213> ORGANISM: Artificial sequence
<220> FEATURE:
<223> OTHER INFORMATION: UN1shuffle-4

<400> SEQUENCE: 39
ggcaagctct agcacgtctc ctcttcttct tgtgagagta aaaakaaaa ctcccaaaaa     60 aaakaaaatc atcaaaaaaa caaatttcaa aaagagttttt tgtgtttggg gattaaagaa    120
kaaaaaaaac aaggaagaag aaakaagaag aagaagaaga agaagaagaa gcctccacc    179

<210> SEQ ID NO 40
<211> LENGTH: 160
<212> TYPE: DNA
<213> ORGANISM: Artificial sequence
<220> FEATURE:
<223> OTHER INFORMATION: UN1shuffle-5

<400> SEQUENCE: 40
ggcaagctct agcacgtctc ctcttcttct tgtgagagta aaaataaaa ctcccaaaaa     60 aaagaaaatc atcaaaaaaa caaatttcaa aaagagttttt tgtgtttggg gattaaagaa    120
taaaaaaaac aaggaagaag aagaagaaga agcctccacc                          160

<210> SEQ ID NO 41
<211> LENGTH: 177
<212> TYPE: DNA
<213> ORGANISM: Artificial sequence
<220> FEATURE:
<223> OTHER INFORMATION: UN1shuffle-6

<400> SEQUENCE: 41
caagctctag cacgtctcct cttcttcttg tgagagtaaa aaakaaaact cccaaaaaaa    60
akaaaatcat caaaaaaaca aatttcaaaa agagttttttg tgtttgggga ttaaagaaka    120
aaaaaaacaa ggaagaagaa akaagaagaa gaagaagaag aagaagagc ctccacc       177

<210> SEQ ID NO 42
<211> LENGTH: 277
<212> TYPE: DNA
<213> ORGANISM: Artificial sequence
<220> FEATURE:
<223> OTHER INFORMATION: UN2shuffle-1

<400> SEQUENCE: 42
caagctctag cacgtctcct cttcttcttg tgagagtaaa aaakaaaact cccaaaaaaa    60
akaaaatcat caaaaaaaca aatttcaaaa agagttttttg tgtttgggga ttaaagaaka    120
aaaaaaacaa ggaagaagaa akaagaagaa gaagaagaag aagaagaagc aggtgagtaa    180
gcgcagttgt cgtctcttgc ggtgccgttg ctggttctca cacctttttag gtctgttctc    240
```

<210> SEQ ID NO 43
<211> LENGTH: 267
<212> TYPE: DNA
<213> ORGANISM: Artificial sequence
<220> FEATURE:
<223> OTHER INFORMATION: UN2shuffle-2

<400> SEQUENCE: 43

```
atcaagctct agcacgtctc ctcttcttct tgtgagagta aaaakaaaa ctcccaaaaa      60
aaakaaaatc atcaaaaaaa caaatttcaa aaagagtgag gtaagattat cgatatttaa    120
attatttatt tcttcttttc catttttttg gctaacattt tcctaggttt tattatatct    180
agcaggtacg ttttgtgttt ggggattaaa gaakaaaaaa acaaggaag aagaaakaag     240
aagaagaaga agaagaagaa gaaaaca                                         267
```

<210> SEQ ID NO 44
<211> LENGTH: 264
<212> TYPE: DNA
<213> ORGANISM: Artificial sequence
<220> FEATURE:
<223> OTHER INFORMATION: CAA1

<400> SEQUENCE: 44

```
caagctctac caccaagaac aaacaacaac aacatatata aaacaacaac caccatctcc     60
tcttcttctt gtcaactcca aaatcaaact cccaaaaaaa agcaaatcat caaaagtgag    120
gtaagattat cgatatttaa attatttatt tcttcttttc catttttttg gctaacattt    180
tcctaggttt tattatatct agcaggtacg aaatttcaaa caacaacaac aaacaacaaa    240
caacattaac atcatatcaa aacc                                            264
```

<210> SEQ ID NO 45
<211> LENGTH: 188
<212> TYPE: DNA
<213> ORGANISM: Artificial sequence
<220> FEATURE:
<223> OTHER INFORMATION: CAA2

<400> SEQUENCE: 45

```
caacctctac caccaacaac aaacaacaac aacaacaaca caacaacaa ccctctccac      60
atctccctct cagagtaaaa aacaaaactc caaaaaaaa gaaaatcatc aaaaaaacaa     120
atttcaaaaa gacttcttct cattccttat taaagaacaa aaaaaacaag gcggccgccc    180
ccttcacc                                                              188
```

<210> SEQ ID NO 46
<211> LENGTH: 207
<212> TYPE: DNA
<213> ORGANISM: Artificial sequence
<220> FEATURE:
<223> OTHER INFORMATION: CAA3

<400> SEQUENCE: 46

```
gtatttttac aacaattacc aacaacaaca aacaacaaac aacattacaa ttactattta     60
caattacaag cgtctcctct tcttcttgtg agagtaaaaa ataaaactcc caaaaaaag    120
aaaatcatca aaaaaacaaa tttcaaaaag agttttttgtg tttggggatt aaagaataaa   180
aaaaacaagg cggccgcccc cttcacc                                         207
```

<210> SEQ ID NO 47
<211> LENGTH: 188
<212> TYPE: DNA
<213> ORGANISM: Artificial sequence
<220> FEATURE:
<223> OTHER INFORMATION: CAA4

<400> SEQUENCE: 47

```
caagctctac caccaagaac aaacaacaac aacatatata aaacaacaac caccatctcc    60
tcttcttctt gtcaactcca aaatcaaact cccaaaaaaa agcaaatcat caaaaccaca   120
aatttcaaac aacaacaaca aacaacaaac aacattaaca tcatatcaag gcggccgccc   180
ccttcacc                                                            188
```

<210> SEQ ID NO 48
<211> LENGTH: 175
<212> TYPE: DNA
<213> ORGANISM: Artificial sequence
<220> FEATURE:
<223> OTHER INFORMATION: CAA5

<400> SEQUENCE: 48

```
caacctctac caccaacaac aaacaacaac aacaacaaca caacaacaa ccctctccac    60
atctccctct cagagtaaaa aacaaaattg acaaaaaaaa gatttattaa taaaaacaaa   120
tttcaaaaag aattcaactc attcaatatt acaacaagaa caaaggaggt cacat         175
```

<210> SEQ ID NO 49
<211> LENGTH: 177
<212> TYPE: DNA
<213> ORGANISM: Artificial sequence
<220> FEATURE:
<223> OTHER INFORMATION: CAA6

<400> SEQUENCE: 49

```
caagctctac caccaagaac aaacaacaac aacatatata aaacaacaac caccatctcc    60
tcttcttctt gtcaactcca aaatcaaact cccaaaaaaa agcaaatcat caaaaccaca   120
aatttcaaac aacaacaaca aacaacaaac aacattaaca tcatatcaac ctccacc       177
```

<210> SEQ ID NO 50
<211> LENGTH: 175
<212> TYPE: DNA
<213> ORGANISM: Artificial sequence
<220> FEATURE:
<223> OTHER INFORMATION: TATA1

<400> SEQUENCE: 50

```
caagctctag caggaagaag aaataagaag aagaagaaga agaagaagaa gcgtctcctc    60
ttcttcttga cagagtaaaa aataactttt ataataaaga aaatcatcaa aaaacaaat    120
ttcaaaaaga gttttttgtgt ttggggatta aagaataaaa aaaaggaggt cacat         175
```

<210> SEQ ID NO 51
<211> LENGTH: 177
<212> TYPE: DNA
<213> ORGANISM: Artificial sequence
<220> FEATURE:
<223> OTHER INFORMATION: TATA2

<400> SEQUENCE: 51

```
caagctctag caggaagaag aaataagaag aagtatataa aagaagaaga agcgtctcct    60
cttcttcttg tgaagtaaaa aataaaactc ccaaaaaaaa gaaaatcatc aaaaaaacaa   120
```

| | |
|---|---|
| atttcaaaaa gagtttttgt gtttggggat taaagaataa aaaaaacaac ctccacc | 177 |

<210> SEQ ID NO 52
<211> LENGTH: 315
<212> TYPE: DNA
<213> ORGANISM: Artificial sequence
<220> FEATURE:
<223> OTHER INFORMATION: fragment

<400> SEQUENCE: 52

| | |
|---|---|
| ggagttccgc gttacataac ttacggtaaa tggcccgcct ggctgaccgc ccaacgaccc | 60 |
| ccgcccattg acgtcaataa tgacgtatgt tcccatagta acgccaatag ggactttcca | 120 |
| ttgacgtcaa tgggtggagt atttacggta aactgcccac ttggcagtac atcaagtgta | 180 |
| tcatatgcca agtacgcccc ctattgacgt caatgacggt aaatggcccg cctggcatta | 240 |
| tgcccagtac atgaccttat gggactttcc tacttggcag tacatctacg tattagtcat | 300 |
| cgctattacc atggt | 315 |

<210> SEQ ID NO 53
<211> LENGTH: 303
<212> TYPE: DNA
<213> ORGANISM: Artificial sequence
<220> FEATURE:
<223> OTHER INFORMATION: fragment

<400> SEQUENCE: 53

| | |
|---|---|
| ggcctccgcg ccgggttttg gcgcctcccg cgggcgcccc cctcctcacg gcgagcgctg | 60 |
| ccacgtcaga cgaagggcgc agcgagcgtc ctgatccttc cgcccggacg ctcaggacag | 120 |
| cggcccgctg ctcataagac tcggccttag aaccccagta tcagcagaag gacattttag | 180 |
| gacgggactt gggtgactct agggcactgg ttttctttcc agagagcgga acaggcgagg | 240 |
| aaaagtagtc ccttctcggc gattctgcgg agggatctcc gtggggcggt gaacgccgat | 300 |
| gat | 303 |

<210> SEQ ID NO 54
<211> LENGTH: 305
<212> TYPE: DNA
<213> ORGANISM: Artificial sequence
<220> FEATURE:
<223> OTHER INFORMATION: fragment

<400> SEQUENCE: 54

| | |
|---|---|
| cgttacataa cttacggtaa atggcccgcc tggctgaccg cccaacgacc cccgcccatt | 60 |
| gacgtcaata atgacgtatg ttcccatagt aacgccaata gggactttcc attgacgtca | 120 |
| atgggtggag tatttacggt aaactgccca cttggcagta catcaagtgt atcatatgcc | 180 |
| aagtacgccc cctattgacg tcaatgacgg taaatggccc gcctggcatt atgcccagta | 240 |
| catgacctta tgggactttc ctacttggca gtacatctac gtattagtca tcgctattac | 300 |
| catga | 305 |

<210> SEQ ID NO 55
<211> LENGTH: 1428
<212> TYPE: DNA
<213> ORGANISM: Artificial sequence
<220> FEATURE:
<223> OTHER INFORMATION: fragment

<400> SEQUENCE: 55

| | |
|---|---|
| cgttacataa cttacggtaa atggcccgcc tggctgaccg cccaacgacc cccgcccatt | 60 |

```
gacgtcaata atgacgtatg ttcccatagt aacgccaata gggactttcc attgacgtca      120
atgggtggag tatttacggt aaactgccca cttggcagta catcaagtgt atcatatgcc      180
aagtacgccc cctattgacg tcaatgacgg taaatggccc gcctggcatt atgcccagta      240
catgacctta tgggactttc ctacttggca gtacatctac gtattagtca tcgctattac      300
catgaattgg tttgatctga ttataaccta ggtcgaggaa ggtttcttca actcaaattc      360
atccgcctga taattttctt atattttcct aaagaaggaa gagaagcgca tagaggagaa      420
gggaaataat ttttaggag cctttcttac ggctatgagg aatttggggc tcagttgaaa       480
agcctaaact gcctctcggg aggttgggcg cggcgaacta ctttcagcgg cgcacggaga      540
cggcgtctac gtgaggggtg ataagtgacg caacactcgt tgcataaatt tgcctccgcc      600
agcccggagc atttaggggc ggttggcttt gttgggtgag cttgtttgtg tccctgtggg      660
tggacgtggt tggtgattgg caggatcctg gtatccgcta acaggtactg gcccgcagcc      720
gtaacgacct ggggggggtg tgagaggggg gaatgggtga ggtcaaggtg gaggcttctt      780
ggggttgggt gggccgctga ggggagggcg tggggaggg gagggcgagg tgacgcggcg       840
ctgggccttt ccgggacagt gggccttgtt gacctgaggg gggcgagggc ggttggcgcg      900
cgcgggttga cggaaactaa cggacgccta accgatcggc gattctgtcg agtttacttc      960
gcggggaagg cggaaaagag gtagtttgtg tggtttctgg aagcctttac tttgaatct       1020 cagtgtgaga aggtgcccc ttcttgtgtt tcaatgggat tttatttcg cgagtcttgt        1080 gggtttggtt ttgttttcag tttgcctaac accgtgctta ggtttgaggc agattggagt      1140
tcggtcgggg gagtttgaat atccggaaca gttagtgggg aaagctgtgg acgattggta     1200
agagagcgct ctggattttc cgctgttgac gttgaaacct tgaatgacga atttcgtatt     1260
aagtgactta gccttgtaaa attgaggga ggcttgcgga atattaacgt atttaaggca      1320
ttttgaagga atagttgcta atttttgaaga atattaggtg taaaagcaag aaatacaatg    1380
atcctgaggt gacacgctta tgttttactt ttaaactagg tcagcatg                  1428
```

<210> SEQ ID NO 56
<211> LENGTH: 1055
<212> TYPE: DNA
<213> ORGANISM: Artificial sequence
<220> FEATURE:
<223> OTHER INFORMATION: fragment

<400> SEQUENCE: 56

```
ggagttccgc gttacataac ttacggtaaa tggcccgcct ggctgaccgc ccaacgaccc       60
ccgcccattg acgtcaataa tgacgtatgt tcccatagta acgccaatag ggactttcca      120
ttgacgtcaa tggtggagt atttacggta aactgcccac ttggcagtac atcaagtgta       180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtcgagg tgagccccac gttctgcttc actctcccca tctcccccc      360 ctccccaccc ccaattttgt atttatttat tttttaatta ttttgtgcag cgatgggggc     420 ggggggggg ggggcgcgc gccaggcggg gcggggcggg gcgaggggcg gggcggggcg       480
aggcggagag gtgcggcggc agccaatcag agcggcgcgc tccgaaagtt tccttttatg    540
gcgaggcggc ggcggcggcg gccctataaa aagcgaagcg cgcggcgggc gggagtcgct     600
gcgcgctgcc ttcgccccgt gccccgctcc gccgccgcct cgcgccgccc gccccggctc     660
```

| | |
|---|---|
| tgactgaccg cgttactaaa acaggtaagt ccggcctccg cgccgggttt tggcgcctcc | 720 |
| cgcgggcgcc cccctcctca cggcgagcgc tgccacgtca gacgaagggc gcagcgagcg | 780 |
| tcctgatcct tccgcccgga cgctcaggac agcggcccgc tgctcataag actcggcctt | 840 |
| agaaccccag tatcagcaga aggacatttt aggacgggac ttgggtgact ctagggcact | 900 |
| ggttttcttt ccagagagcg gaacaggcga ggaaaagtag tcccttctcg gcgattctgc | 960 |
| ggagggatct ccgtggggcg gtgaacgccg atgatgcctc tactaaccat gttcatgttt | 1020 |
| tctttttttt tctacaggtc ctgggtgacg aacag | 1055 |

<210> SEQ ID NO 57
<211> LENGTH: 753
<212> TYPE: DNA
<213> ORGANISM: Artificial sequence
<220> FEATURE:
<223> OTHER INFORMATION: CMV promoter

<400> SEQUENCE: 57

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca aacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccctattg acgtcaatga | 420 |
| cggtaaatgg cccgcctggc attatgccca gtacatgacc ttacgggact ttcctacttg | 480 |
| gcagtacatc tacgtattag tcatcgctat taccatagtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaataaccc | 660 |
| cgccccgttg acgcaaatgg gcggtaggcg tgtacggtgg gaggtctata taagcagagc | 720 |
| tcgtttagtg aaccgtcaga tcactagaag ctt | 753 |

<210> SEQ ID NO 58
<211> LENGTH: 69
<212> TYPE: DNA
<213> ORGANISM: Artificial sequence
<220> FEATURE:
<223> OTHER INFORMATION: minimal CMV promoter

<400> SEQUENCE: 58

| | |
|---|---|
| taggcgtgta cggtgggagg tctatataag cagagctcgt ttagtgaacc gtcagatcac | 60 |
| tagaagctt | 69 |

<210> SEQ ID NO 59
<211> LENGTH: 2248
<212> TYPE: DNA
<213> ORGANISM: Artificial sequence
<220> FEATURE:
<223> OTHER INFORMATION: EEE1-Xt

<400> SEQUENCE: 59

| | |
|---|---|
| tggtgaccct gtctcaaaaa accctcaaaa agtgttggga ttagtggcat gcaccaccat | 60 |
| tcccaccaaa ggtttatttt taataatatg tgtgtgagtg tgtatcacta tgagtatatg | 120 |
| tcaatatgtg tcaatgtccc cagggacatt taaagagccc ctgaagctgg agtcataggc | 180 |

```
cattatgaac tgcctgacat ggctaatggg aattgaactc agattttctg gaagttatac      240
ctgctcttac tgctgagcca tgtctctgaa gaccccaggg attttttttt ttttttgaga      300
caggtatttt ctgtatagcc ctggctgtcc tgaaagcact ctctatatgt agaccaggct      360
tgcctggagc ttggatatgc acctgcttct gcctcaggaa tggtgggatt gaaggtgtgc      420
accaccacat ccgctaacat gcacaattct taatgggttt atatcttatt taatgaatga      480
aaggtttggg ggatggatgt agcttaatgg aaaatgactg aagatttcaa ttaaaaatct      540
ggggcttagc tgcgcggtgg gtggtgcctg cctttagtcc cagtactggg gaggcagagg      600
aaggaggatc tctgtgagtt cgaggccagc tggtctataa cgtgagttcc aggacagcca      660
gagatacaca gacaaaccct gtctcaccaa aacaaaacaa caacaacaac aacaaatctg      720
ggacgtaggc ttggtgtggt ggcacacatt ttgattccag cacttggaag gaagaggcct      780
gcatggtcta catagcttgt ttcaggcaac cagagctaca tagtgagatc ctgtctcaac      840
aaaaataaaa taatctaagg cttcaaaggg ttcaatctct taggtagcta aatatgaaca      900
aaatttggga aatgtgacct tttccttagt gacagtcaga tagaaccttc tcgagtgcaa      960
ggacaccaag tgcaaacagg ctcaagaaca gcctggaaag gtctagtgct atggggcttc     1020
aggtcgaatg ccaactgttt tcaagaactg tgtggatttt tctgcctgta acgaattcag     1080
attcattttt caaaactcgg ggagagtttt ccccctttat aattttttt ttaaatttat      1140 taaactttgt ttcgttcccc ttgttttgag aattgcagag tcatccaccc tgtcacagtg     1200
ccagggagct cagggatggg cccaggggcc tggcggggct gaaggggctg gggaagcgag     1260
ggctccaaag ggaccccagt gtggcaggag ccaaagccct aggtccctag aacgcagagg     1320
ccaccgggac cccccagacg gggtaagcgg gtgggtgtct ggggcgcgaa gccgcactgc     1380
gcatgcgccg aggtccgctc cggccgcgct gatccaagcc gggttctcgc gccgacctgg     1440
tcgtgattga caagtcacac acgctgatcc ctccgcgggg ccgcacaggg tcacagcctt     1500
tcccctcccc acaaagcccc ctactctctg ggcaccacac acgaacattc cttgagcgtg     1560
accttgttgg ctctagtcag gcgcctccgg tgcagagact ggaacggcct tgggaagtag     1620
tccctaaccg catttccgcg gagggatcgt cgggagggcg tggcttctga ggattatata     1680
aggcgactcc gggcgggtct tagctagttc cgtcggagac ccgagttcag tcgccgcttc     1740
tctgtgagga ctgctgccgc cgccgctggt gaggagaagc cgccgcgctt ggcgtagctg     1800
agagacgggg aggggcgcg gacacgaggg gcagcccgcg gcctggacgt tctgtttccg      1860
tggcccgcga ggaaggcgac tgtcctgagg cggaggaccc agcggcaaga tggcggccaa     1920
gtggaagcct gaggggatag gcgagcggcc ctgaggcgct cgacggggtt ggggggaag      1980 caggcccgcg aggcagctgc agccgggaac gtgcggccaa ccccttattt tttttgacgg     2040
gttgcgggcc gtaggtgcct ccgaagtgag agccgtgggc gtttgactgt cgggagaggt     2100
cggtcggatt ttcatccgtt gctaaagacg gaagtgcgac tgagacggga aggggggga     2160 gtcggttggt ggcggttgaa cctggactaa ggcgcacatg acgtcgcggt ttctatgggc     2220
tcataatggg tggtgaggac atttcccct                                        2248
```

<210> SEQ ID NO 60
<211> LENGTH: 1159
<212> TYPE: DNA
<213> ORGANISM: Artificial sequence
<220> FEATURE:
<223> OTHER INFORMATION: EEE1-80

<400> SEQUENCE: 60

```
tcaaaactcg gggagagttt tcccccttta taatttttt tttaaattta ttaaactttg      60
tttcgttccc cttgttttga gaattgcaga gtcatccacc ctgtcacagt gccagggagc    120
tcagggatgg gcccagggc ctggcggggc tgaaggggct ggggaagcga gggctccaaa    180
gggaccccag tgtggcagga gccaaagccc taggtcccta gaacgcagag gccaccggga    240
ccccccagac ggggtaagcg ggtgggtgtc tggggcgcga agccgcactg cgcatgcgcc    300
gaggtccgct ccggccgcgc tgatccaagc cgggttctcg cgccgacctg gtcgtgattg    360
acaagtcaca cacgctgatc cctccgcggg gccgcacagg gtcacagcct ttcccctccc    420
cacaaagccc cctactctct gggcaccaca cacgaacatt ccttgagcgt gaccttgttg    480
gctctagtca ggcgcctccg gtgcagagac tggaacggcc ttgggaagta gtccctaacc    540
gcatttccgc ggagggatcg tcgggagggc gtggcttctg aggattatat aaggcgactc    600
cgggcgggtc ttagctagtt ccgtcggaga cccgagttca gtcgccgctt ctctgtgagg    660
actgctgccg ccgccgctgg tgaggagaag ccgccgcgct tggcgtagct gagagacggg    720
gaggggcgc ggacacgagg ggcagcccgc ggcctggacg ttctgtttcc gtggcccgcg    780
aggaaggcga ctgtcctgag gcggaggacc cagcggcaag atggcggcca agtggaagcc    840
tgagggata ggcgagcggc cctgaggcgc tcgacgggt tggggggaa gcaggcccgc    900
gaggcagctg cagccgggaa cgtgcggcca accccttatt tttttttgacg ggttgcgggc    960
cgtaggtgcc tccgaagtga gagccgtggg cgtttgactg tcgggagagg tcggtcggat   1020
tttcatccgt tgctaaagac ggaagtgcga ctgagacggg aagggggggg agtcggttgg   1080
tggcggttga acctggacta aggcgcacat gacgtcgcgg tttctatggg ctcataatgg   1140
gtggtgagga catttccct                                                 1159
```

<210> SEQ ID NO 61
<211> LENGTH: 869
<212> TYPE: DNA
<213> ORGANISM: Artificial sequence
<220> FEATURE:
<223> OTHER INFORMATION: EEE1-60

<400> SEQUENCE: 61

```
cgcatgcgcc gaggtccgct ccggccgcgc tgatccaagc cgggttctcg cgccgacctg      60
gtcgtgattg acaagtcaca cacgctgatc cctccgcggg gccgcacagg gtcacagcct    120
ttcccctccc cacaaagccc cctactctct gggcaccaca cacgaacatt ccttgagcgt    180
gaccttgttg gctctagtca ggcgcctccg gtgcagagac tggaacggcc ttgggaagta    240
gtccctaacc gcatttccgc ggagggatcg tcgggagggc gtggcttctg aggattatat    300
aaggcgactc cgggcgggtc ttagctagtt ccgtcggaga cccgagttca gtcgccgctt    360
ctctgtgagg actgctgccg ccgccgctgg tgaggagaag ccgccgcgct tggcgtagct    420
gagagacggg gaggggcgc ggacacgagg ggcagcccgc ggcctggacg ttctgtttcc    480
gtggcccgcg aggaaggcga ctgtcctgag gcggaggacc cagcggcaag atggcggcca    540
agtggaagcc tgagggata ggcgagcggc cctgaggcgc tcgacgggt tggggggaa    600
gcaggcccgc gaggcagctg cagccgggaa cgtgcggcca accccttatt tttttttgacg    660
ggttgcgggc cgtaggtgcc tccgaagtga gagccgtggg cgtttgactg tcgggagagg    720
tcggtcggat tttcatccgt tgctaaagac ggaagtgcga ctgagacggg aagggggggg    780
agtcggttgg tggcggttga acctggacta aggcgcacat gacgtcgcgg tttctatggg    840
```

```
ctcataatgg gtggtgagga catttccct                                      869
```

<210> SEQ ID NO 62
<211> LENGTH: 724
<212> TYPE: DNA
<213> ORGANISM: Artificial sequence
<220> FEATURE:
<223> OTHER INFORMATION: EEE1-50

<400> SEQUENCE: 62

```
tctctgggca ccacacacga acattccttg agcgtgacct tgttggctct agtcaggcgc     60
ctccggtgca gagactggaa cggccttggg aagtagtccc taaccgcatt tccgcggagg    120
gatcgtcggg agggcgtggc ttctgaggat tatataaggc gactccgggc gggtcttagc    180
tagttccgtc ggagacccga gttcagtcgc cgcttctctg tgaggactgc tgccgccgcc    240
gctggtgagg agaagccgcc gcgcttggcg tagctgagag acggggaggg ggcgcggaca    300
cgaggggcag cccgcggcct ggacgttctg tttccgtggc ccgcgaggaa ggcgactgtc    360
ctgaggcgga ggacccagcg gcaagatggc ggccaagtgg aagcctgagg ggataggcga    420
gcggccctga ggcgctcgac ggggttgggg ggaagcagg cccgcgaggc agctgcagcc     480
gggaacgtgc ggccaacccc ttattttttt tgacgggttg cgggccgtag gtgcctccga    540
agtgagagcc gtgggcgttt gactgtcggg agaggtcggt cggattttca tccgttgcta    600
aagacggaag tgcgactgag acgggaaggg ggggagtcg gttggtggcg gttgaacctg     660
gactaaggcg cacatgacgt cgcggtttct atgggctcat aatgggtggt gaggacattt    720
ccct                                                                 724
```

<210> SEQ ID NO 63
<211> LENGTH: 1449
<212> TYPE: DNA
<213> ORGANISM: Artificial sequence
<220> FEATURE:
<223> OTHER INFORMATION: EEE1-SL

<400> SEQUENCE: 63

```
tttcaggcaa ccagagctac atagtgagat cctgtctcaa caaaaataaa ataatctaag     60
gcttcaaagg gttcaatctc ttaggtagct aaatatgaac aaaatttggg aaatgtgacc    120
ttttccttag tgacagtcag atagaacctt ctcgagtgca aggacaccaa gtgcaaacag    180
gctcaagaac agcctggaaa ggtctagtgc tatgggctt caggtcgaat gccaactgtt      240
ttcaagaact gtgtggattt ttctgcctgt aacgaattca gattcatttt tcaaaactcg    300
gggagagttt tccccctta taatttttt tttaaattta ttaaactttg tttcgttccc      360
cttgttttga gaattgcaga gtcatccacc ctgtcacagt gccagggagc tcagggatgg    420
gcccaggggc ctggcggggc tgaaggggct ggggaagcga gggctccaaa gggaccccag    480
tgtggcagga gccaaagccc taggtcccta gaacgcagag gccaccggga cccccagac     540
ggggaaagcg gttgggtgtc tggggcgcga agccgcactg cgcatgcgcc gaggtccgct    600
ccggccgcgc tgatccaagc cgggttctcg cgccgacctg gtcgtgattg acaagtcaca    660
cacgctgatc cctccgcggg gccgcacagg gtcacagcct ttcccctccc cacaaagccc    720
cctactctct gggcaccaca cacgaacatt ccttgagcgt gaccttgttg gctctagtca    780
ggcgcctccg gtgcagagac tggaacggcc ttgggaagta gtccctaacc gcatttccgc    840
ggagggatcg tcggggggc gtggcttctg aggattatat aaggcgactc cgggcgggtc    900
```

```
ttagctagtt ccgtcggaga cccgagttca gtcgccgctt ctctgtgagg actgctgccg    960
ccgccgctgc tgaggagaag ccgccgcgct tggcgtagct gagagacggg gaggggcgc    1020 ggacacgagg ggcagcccgc ggcctggacg ttctgtttcc gtggcccgcg aggaaggcga   1080
ctgtcctgag gcgaggacc cagcggcaag atggcggcca agtggaagcc tgaggggata    1140
ggcgagcggc cctgaggcgc tcgacggggt tggggggaa gcaggcccgc gaggcagctg    1200
cagccgggaa cgtgcggcca acccttatt tttttgacg ggttgcgggc cgtaggtgcc     1260
tccgaattga gagccgtggg cgtttgactg tcgggagagg tcggtcggat tttcatccgt   1320
tgctaaagac ggaagtgcga ctgagacggg aaggggggg agtcggttgg tggcggttga    1380
acctggacta aggcgcacat gacgtcgcgg tttctatggg ctcataatgg gtggtgagga   1440
catttccct                                                           1449
```

<210> SEQ ID NO 64
<211> LENGTH: 33
<212> TYPE: DNA
<213> ORGANISM: Artificial sequence
<220> FEATURE:
<223> OTHER INFORMATION: HC RACE PRIMER

<400> SEQUENCE: 64

```
gctggtgccc aggtccttag cgcaatagta cac                                33
```

<210> SEQ ID NO 65
<211> LENGTH: 4128
<212> TYPE: DNA
<213> ORGANISM: Artificial sequence
<220> FEATURE:
<223> OTHER INFORMATION: Light chain vector sequence without the coding
      sequence

<400> SEQUENCE: 65

```
tgcaggcggc cgcttttcagg caaccagagc tacatagtga gatcctgtct caacaaaaat    60
aaaataatct aaggcttcaa agggttcaat ctcttaggta gctaaatatg aacaaaattt    120
gggaaatgtg acctttttcct tagtgacagt cagatagaac cttctcgagt gcaaggacac   180
caagtgcaaa caggctcaag aacagcctgg aaaggtctag tgctatgggg cttcaggtcg    240
aatgccaact gttttcaaga actgtgtgga ttttttctgcc tgtaacgaat tcagattcat   300
ttttcaaaac tcggggagag ttttccccct ttataatttt ttttttaaat ttattaaact   360
ttgtttcgtt ccccttgttt tgagaattgc agagtcatcc accctgtcac agtgccaggg   420
agctcaggga tgggcccagg ggcctggcgg ggctgaaggg gctggggaag cgagggctcc    480
aaagggaccc cagtgtggca ggagccaaag ccctaggtcc ctagaacgca gaggccaccg   540 ggaccccca gacggggtaa gcgggtgggt gtctggggcg cgaagccgca ctgcgcatgc     600
gccgaggtcc gctccggccg cgctgatcca agccgggttc tcgcgccgac ctggtcgtga   660
ttgacaagtc acacacgctg atccctccgc ggggccgcac agggtcacag cctttccct    720 ccccacaaag cccctactc tctgggcacc acacacgaac attccttgag cgtgaccttg    780
ttggctctag tcaggcgcct ccggtgcaga gactggaacg gccttgggaa gtagtcccta   840
accgcatttc gcggaggga tcgtcggag ggcgtggctt ctgaggatta tataaggcga    900
ctccgggcgg gtcttagcta gttccgtcgg agacccgagt tcagtcgccg cttctctgtg   960
aggactgctg ccgccgccgc tgtgaggag aagccgccgc gcttggcgta gctgagagac   1020
ggggaggggg cgcggacacg aggggcagcc cgcggcctgg acgttctgtt tccgtggccc   1080
```

```
gcgaggaagg cgactgtcct gaggcggagg acccagcggc aagatggcgg ccaagtggaa    1140
gcctgagggg ataggcgagc ggccctgagg cgctcgacgg ggttgggggg gaagcaggcc    1200
cgcgaggcag ctgcagccgg gaacgtgcgg ccaacccctt atttttttg acgggttgcg     1260 ggccgtaggt gcctccgaag tgagagccgt gggcgtttga ctgtcgggag aggtcggtcg    1320
gattttcatc cgttgctaaa gacggaagtg cgactgagac gggaaggggg gggagtcggt    1380
tggtggcggt tgaacctgga ctaaggcgca catgacgtcg cggtttctat ggctcataa     1440 tgggtggtga ggacatttcc ctgtttaaac ttaaacaagt tgtacaaaa aagcaggcta     1500 gatcttcaat attggccatt agccatatta ttcattggtt atatagcata aatcaatatt    1560
ggctattggc cattgcatac gttgtatcta tatcataata tgtacattta tattggctca   1620
tgtccaatat gaccgccatg ttggcattga ttattgacta gttattaata gtaatcaatt   1680
acggggtcat tagttcatag cccatatatg gagttccgcg ttacataact tacggtaaat   1740
ggcccgcctg gctgaccgcc caacgacccc cgcccattga cgtcaataat gacgtatgtt   1800
cccatagtaa cgccaatagg gactttccat tgacgtcaat gggtggagta tttacggtaa   1860
actgcccact tggcagtaca tcaagtgtat catatgccaa gtccgccccc tattgacgtc   1920
aatgacggta aatggcccgc ctggcattat gcccagtaca tgaccttacg gactttcct    1980 acttggcagt acatctacgt attagtcatc gctattacca tagtgatgcg gttttggcag   2040
tacaccaatg ggcgtggata gcggtttgac tcacggggat ttccaagtct ccaccccatt   2100
gacgtcaatg ggagtttgtt ttggcaccaa aatcaacggg actttccaaa atgtcgtaat   2160
aaccccgccc cgttgacgca aatgggcggt aggcgtgtac ggtgggaggt ctatataagc   2220
agagctcgtt tagtgaaccg tcagatcact agaagcttaa tacgactcac tatagggaga   2280
cccaagctgg ctagcgttta aacgggccct ctagtaacgg ccgccagtgt gctggaattc   2340
ggcttaactc tagaccatgg ggcgcgccgg ttcagcctcg actgtgcctt ctagttgcca   2400
gccatctgtt gtttgcccct ccccgtgcc ttccttgacc ctggaaggtg ccactcccac    2460
tgtcctttcc taataaaatg aggaaattgc atcgcattgt ctgagtaggt gtcattctat   2520
tctggggggt ggggtggggc aggacagcaa ggggaggat tgggaagaca atagcaggca    2580
tgctggggat gcggtgggct ctatggcttc tgaggcggaa agaaccagct ggatccatcc   2640
gttagatatc tgtggaatgt gtgtcagtta gggtgtggaa agtccccagg ctccccagca   2700
ggcagaagta tgcaaagcat gcatctcaat tagtcagcaa ccaggtgtgg aaagtcccca   2760
ggctccccag caggcagaag tatgcaaagc atgcatctca attagtcagc aaccatagtc   2820
ccgcccctaa ctccgcccat cccgcccta actccgccca gttccgccca ttctccggcc    2880
catggctgac taatttttt tatttatgca gaggccgagg ccgcctctgc ctctgagcta    2940
ttccagaagt agtgaggagg cttttttgga ggcctaggct tttgcaaaaa gctcccggga   3000
gcttgtatat ccattttcgg atctgatcaa gagacaggat gaggatcgtt tcacatgatt   3060
gaacaagatg gattgcacgc aggttctccg gccgcttggg tggagaggct attcggctat   3120
gactgggcac aacagacaat cggctgctct gatgccgccg tgttccggct gtcagcgcag   3180
gggcgcccgg ttcttttgt caagaccgac ctgtccggtg ccctgaatga actgcaggac   3240
gaggcagcgc ggctatcgtg gctggccacg acgggcgttc cttgcgcagc tgtgctcgac   3300
gttgtcactg aagcgggaag ggactggctg ctattgggcg aagtgccggg gcaggatctc   3360
ctgtcatctc accttgctcc tgccgagaaa gtatccatca tggctgatgc aatgcggcgg   3420
ctgcatacgc ttgatccggc tacctgccca ttcgaccacc aagcgaaaca tcgcatcgag   3480
```

| | | |
|---|---|---|
| cgagcacgta ctcggatgga agccggtctt gtcgatcagg atgatctgga cgaagagcat | 3540 | |
| caggggctcg cgccagccga actgttcgcc aggctcaagg cgcgcatgcc cgacggcgag | 3600 | |
| gatctcgtcg tgacacatgg cgatgcctgc ttgccgaata tcatggtgga aaatggccgc | 3660 | |
| ttttctggat tcatcgactg tggccggctg ggtgtggcgg accgctatca ggacatagcg | 3720 | |
| ttggctaccc gtgatattgc tgaagagctt ggcggcgaat gggctgaccg cttcctcgtg | 3780 | |
| ctttacggta tcgccgctcc cgattcgcag cgcatcgcct ctatcgcct tcttgacgag | 3840 | |
| ttcttctagg taccacgaga tttcgattcc accgccgcct tctatgaaag gttgggcttc | 3900 | |
| ggaatcgttt tccgggacgc cggctggatg atcctccagc gcgggatct catgctggag | 3960 | |
| ttcttcgccc accccaactt gtttattgca gcttataatg gttacaaata aagcaatagc | 4020 | |
| atcacaaatt tcacaaataa agcatttttt tcactgcatt ctagttgtgg tttgtccaaa | 4080 | |
| ctcatcaatg tatcttatca tgtctcaggt tgatgagcat attttacc | 4128 | |

<210> SEQ ID NO 66
<211> LENGTH: 2647
<212> TYPE: DNA
<213> ORGANISM: Artificial sequence
<220> FEATURE:
<223> OTHER INFORMATION: Heavy chain vector sequence without the coding
      sequence

<400> SEQUENCE: 66

| | | |
|---|---|---|
| tgcaggcggc cgctttcagg caaccagagc tacatagtga gatcctgtct caacaaaaat | 60 | |
| aaaataatct aaggcttcaa agggttcaat ctcttaggta gctaaatatg aacaaaattt | 120 | |
| gggaaatgtg accttttcct tagtgacagt cagatagaac cttctcgagt gcaaggacac | 180 | |
| caagtgcaaa caggctcaag aacagcctgg aaaggtctag tgctatgggg cttcaggtcg | 240 | |
| aatgccaact gttttcaaga actgtgtgga ttttctgcc tgtaacgaat tcagattcat | 300 | |
| ttttcaaaac tcggggagag ttttcccct ttataatttt tttttaaat ttattaaact | 360 | |
| ttgtttcgtt ccccttgttt tgagaattgc agagtcatcc accctgtcac agtgccaggg | 420 | |
| agctcaggga tgggcccagg ggcctggcgg ggctgaaggg gctggggaag cgagggctcc | 480 | |
| aaagggaccc cagtgtggca ggagccaaag ccctaggtcc ctagaacgca gaggccaccg | 540 | |
| ggaccccca gacggggtaa gcgggtgggt gtctggggcg cgaagccgca ctgcgcatgc | 600 | |
| gccgaggtcc gctccggccg cgctgatcca agccgggttc tcgcgccgac ctggtcgtga | 660 | |
| ttgacaagtc acacacgctg atcctccgc ggggccgcac agggtcacag cctttccct | 720 | |
| ccccacaaag ccccctactc tctgggcacc acacacgaac attccttgag cgtgaccttg | 780 | |
| ttggctctag tcaggcgcct ccggtgcaga gactggaacg gccttgggaa gtagtcccta | 840 | |
| accgcatttc gcggaggga tcgtcgggag ggcgtggctt ctgaggatta tataaggcga | 900 | |
| ctccgggcgg gtcttagcta gttccgtcgg agacccgagt tcagtcgccg cttctctgtg | 960 | |
| aggactgctg ccgccgccgc tggtgaggag aagccgccgc gcttggcgta gctgagagac | 1020 | |
| ggggagggg cgcggacacg aggggcagcc cgcggcctgg acgttctgtt ccgtggccc | 1080 | |
| gcgaggaagg cgactgtcct gaggcggagg acccagcggc aagatggcgg ccaagtggaa | 1140 | |
| gcctgagggg ataggcgagc ggccctgagg cgctcgacgg ggttgggggg gaagcaggcc | 1200 | |
| cgcgaggcag ctgcagccgg gaacgtgcgg ccaaccccctt attttttttg acgggttgcg | 1260 | |
| ggccgtaggt gcctccgaag tgagagccgt gggcgtttga ctgtcgggag aggtcggtcg | 1320 | |
| gattttcatc cgttgctaaa gacggaagtg cgactgagac gggaagggg gggagtcggt | 1380 | |

```
tggtggcggt tgaacctgga ctaaggcgca catgacgtcg cggtttctat gggctcataa    1440
tgggtggtga ggacatttcc ctgtttaaac ttaaacaagt tgtacaaaa aagcaggcta     1500 gatcttcaat attggccatt agccatatta ttcattggtt atatagcata aatcaatatt   1560
ggctattggc cattgcatac gttgtatcta tatcataata tgtacattta tattggctca   1620
tgtccaatat gaccgccatg ttggcattga ttattgacta gttattaata gtaatcaatt   1680
acggggtcat tagttcatag cccatatatg gagttccgcg ttacataact tacggtaaat   1740
ggcccgcctg gctgaccgcc caacgacccc cgcccattga cgtcaataat gacgtatgtt   1800
cccatagtaa cgccaatagg gactttccat tgacgtcaat gggtggagta tttacggtaa   1860
actgcccact tggcagtaca tcaagtgtat catatgccaa gtccgccccc tattgacgtc   1920
aatgacggta aatggcccgc ctggcattat gcccagtaca tgaccttacg ggactttcct   1980
acttggcagt acatctacgt attagtcatc gctattacca tagtgatgcg gttttggcag   2040
tacaccaatg ggcgtggata gcggtttgac tcacggggat ttccaagtct ccaccccatt   2100
gacgtcaatg ggagtttgtt ttggcaccaa aatcaacggg actttccaaa atgtcgtaat   2160
aaccccgccc cgttgacgca aatgggcggt aggcgtgtac ggtgggaggt ctatataagc   2220
agagctcgtt tagtgaaccg tcagatcact agaagcttaa tacgactcac tatagggaga   2280
cccaagctgg ctagcgttta aacgggccct ctagtaacgg ccgccagtgt gctggaattc   2340
ggcttaactc tagaccatgg ggcgcgccgg ttcagcctcg actgtgcctt ctagttgcca   2400
gccatctgtt gtttgcccct ccccgtgcc ttccttgacc ctggaaggtg ccactcccac    2460 tgtccttcc taataaaatg aggaaattgc atcgcattgt ctgagtaggt gtcattctat    2520 tctgggggt ggggtggggc aggacagcaa ggggagggat tgggaagaca atagcaggca    2580
tgctggggat gcggtgggct ctatggcttc tgaggcggaa agaaccagct ggatccatcc   2640
gttagat                                                            2647
```

<210> SEQ ID NO 67
<211> LENGTH: 235
<212> TYPE: PRT
<213> ORGANISM: Artificial sequence
<220> FEATURE:
<223> OTHER INFORMATION: HuMab1 protein light chain

<400> SEQUENCE: 67

```
Met Gly Trp Ser Cys Ile Ile Leu Phe Leu Val Ala Thr Ala Thr Gly
1               5                   10                  15

Val His Ser Ala Gln Asp Ile Gln Met Thr Gln Ser Pro Ser Ser Val
            20                  25                  30

Ser Ala Ser Val Gly Asp Arg Val Thr Ile Thr Cys Arg Ala Ser Gln
        35                  40                  45

Gly Ile Ser Ser Trp Leu Ala Trp Tyr Gln Gln Lys Pro Gly Lys Ala
    50                  55                  60

Pro Lys Leu Leu Ile Tyr Ala Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ala
            100                 105                 110

Asn Asn Phe Pro Leu Thr Phe Gly Gly Gly Thr Lys Val Glu Ile Lys
        115                 120                 125
```

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 68
<211> LENGTH: 474
<212> TYPE: PRT
<213> ORGANISM: Artificial sequence
<220> FEATURE:
<223> OTHER INFORMATION: HuMab1 protein heavy chain

<400> SEQUENCE: 68

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Tyr Ala Met Ser Trp Val Arg Gln Ala Pro Gly Lys Gly Leu
        50                  55                  60

Glu Trp Val Ser Ala Ile Ser Ala Ser Gly His Ser Thr Tyr Leu Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Thr Ala Val
                100                 105                 110

Tyr Tyr Cys Ala Lys Asp Arg Glu Val Thr Met Ile Val Val Leu Asn
            115                 120                 125

Gly Gly Phe Asp Tyr Trp Gly Gln Gly Thr Arg Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
        210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

```
Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 69
<211> LENGTH: 233
<212> TYPE: PRT
<213> ORGANISM: Artificial sequence
<220> FEATURE:
<223> OTHER INFORMATION: HuMab2 protein light chain

<400> SEQUENCE: 69

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140
```

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 70
<211> LENGTH: 470
<212> TYPE: PRT
<213> ORGANISM: Artificial sequence
<220> FEATURE:
<223> OTHER INFORMATION: HuMab2 protein heavy chain

<400> SEQUENCE: 70

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

Thr Leu Met Ile Ser Arg Thr Pro Glu Val Thr Cys Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 71
<211> LENGTH: 5428
<212> TYPE: DNA
<213> ORGANISM: Artificial sequence
<220> FEATURE:
<223> OTHER INFORMATION: pcDNA3.1(+) cloning vector

<400> SEQUENCE: 71
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900

```
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg ggggtgggg tggggcagga cagcaagggg    1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata cggttttt    1560
cgccctttga cgttggagtc cacgttcttt aatagtggac tcttgttcca aactggaaca   1620
acactcaacc ctatctcggt ctattctttt gatttataag gattttgcc gatttcggcc    1680
tattggttaa aaatgagct gatttaacaa aaatttaacg cgaattaatt ctgtggaatg    1740
tgtgtcagtt agggtgtgga aagtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgcccta actccgccca    1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccatttcg    2100
gatctgatca agagacagga tgaggatcgt ttcgcatgat tgaacaagat ggattgcacg   2160
caggttctcc ggccgcttgg gtggagaggc tattcggcta tgactgggca caacagacaa   2220
tcggctgctc tgatgccgcc gtgttccggc tgtcagcgca ggggcgcccg gttcttttg    2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
ccgattcgca gcgcatcgcc ttctatcgcc ttcttgacga gttcttctga gcgggactct   2940
ggggttcgaa atgaccgacc aagcgacgcc caacctgcca tcacgagatt tcgattccac   3000
cgccgccttc tatgaaaggt tgggcttcgg aatcgttttc cgggacgccg gctggatgat   3060
cctccagcgc ggggatctca tgctggagtt cttcgcccac cccaacttgt ttattgcagc   3120
ttataatggt tacaaataaa gcaatagcat cacaaatttc acaaataaag cattttttc    3180
actgcattct agttgtggtt tgtccaaact catcaatgta tcttatcatg tctgtatacc   3240
gtcgacctct agctagagct tggcgtaatc atggtcatag ctgtttcctg tgtgaaattg   3300
```

```
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca aacaaaccac    4200
cgctggtagc ggttttttgg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct tcggggcgaa aactctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc ttttcaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                      5428
```

<210> SEQ ID NO 72
<211> LENGTH: 519
<212> TYPE: PRT
<213> ORGANISM: Artificial sequence
<220> FEATURE:

<223> OTHER INFORMATION: SeAP protein

<400> SEQUENCE: 72

```
Met Leu Leu Leu Leu Leu Leu Gly Leu Arg Leu Gln Leu Ser Leu
1               5                   10                  15

Gly Ile Ile Pro Val Glu Glu Asn Pro Asp Phe Trp Asn Arg Glu
            20                  25                  30

Ala Ala Glu Ala Leu Gly Ala Ala Lys Lys Leu Gln Pro Ala Gln Thr
        35                  40                  45

Ala Ala Lys Asn Leu Ile Ile Phe Leu Gly Asp Gly Met Gly Val Ser
    50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
    210                 215                 220

Phe Arg Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
            260                 265                 270

Ala Ser Leu Asp Pro Ser Val Thr His Leu Met Gly Leu Phe Glu Pro
        275                 280                 285

Gly Asp Met Lys Tyr Glu Ile His Arg Asp Ser Thr Leu Asp Pro Ser
    290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
        355                 360                 365

Ser Leu Val Thr Ala Asp His Ser His Val Phe Ser Phe Gly Gly Tyr
    370                 375                 380

Pro Leu Arg Gly Ser Ser Ile Phe Gly Leu Ala Pro Gly Lys Ala Arg
385                 390                 395                 400
```

```
Asp Arg Lys Ala Tyr Thr Val Leu Leu Tyr Gly Asn Gly Pro Gly Tyr
            405                 410                 415
Val Leu Lys Asp Gly Ala Arg Pro Asp Val Thr Glu Ser Glu Ser Gly
        420                 425                 430
Ser Pro Glu Tyr Arg Gln Gln Ser Ala Val Pro Leu Asp Glu Glu Thr
    435                 440                 445
His Ala Gly Glu Asp Val Ala Val Phe Ala Arg Gly Pro Gln Ala His
450                 455                 460
Leu Val His Gly Val Gln Glu Gln Thr Phe Ile Ala His Val Met Ala
465                 470                 475                 480
Phe Ala Ala Cys Leu Glu Pro Tyr Thr Ala Cys Asp Leu Ala Pro Pro
                485                 490                 495
Ala Gly Thr Thr Asp Ala Ala His Pro Gly Tyr Ser Arg Val Gly Ala
            500                 505                 510
Ala Gly Arg Phe Glu Gln Thr
        515
```

```
<210> SEQ ID NO 73
<211> LENGTH: 2522
<212> TYPE: DNA
<213> ORGANISM: Artificial sequence
<220> FEATURE:
<223> OTHER INFORMATION: EEE1+CMV+TEE

<400> SEQUENCE: 73
tttcaggcaa ccagagctac atagtgagat cctgtctcaa caaaaataaa ataatctaag      60
gcttcaaagg gttcaatctc ttaggtagct aaatatgaac aaaatttggg aaatgtgacc     120
ttttccttag tgacagtcag atagaaacctt ctcgagtgca aggacaccaa gtgcaaacag     180
gctcaagaac agcctggaaa ggtctagtgc tatgggcttc aggtcgaat gccaactgtt      240
ttcaagaact gtgtggattt ttctgcctgt aacgaattca gattcatttt tcaaaactcg     300
gggagagttt tccccctta taattttttt tttaaattta ttaaactttg tttcgttccc     360
cttgttttga gaattgcaga gtcatccacc ctgtcacagt gccagggagc tcagggatgg     420
gcccaggggc ctggcggggc tgaaggggct ggggaagcga gggctccaaa gggaccccag     480
tgtggcagga gccaaagccc taggtcccta gaacgcagag gccaccggga ccccccagac     540
gggtaagcg gtgggtgtc tggggcgcga agccgcactg cgcatgcgcc gaggtccgct      600
ccggccgcgc tgatccaagc cgggttctcg cgccgacctg gtcgtgattg acaagtcaca     660
cacgctgatc cctccgcggg gccgcacagg gtcacagcct ttcccctccc cacaaagccc    720
cctactctct gggcaccaca cacgaacatt ccttgagcgt gaccttgttg gctctagtca    780
ggcgcctccg gtgcagagac tggaacggcc ttgggaagta gtccctaacc gcatttccgc   840
ggagggatcg tcgggagggc gtggcttctg aggattatat aaggcgactc cgggcgggtc    900
ttagctagtt ccgtcggaga cccgagttca gtcgccgctt ctctgtgagg actgctgccg    960
ccgccgctgg tgaggagaag ccgccgcgct tggcgtagct gagagacggg gaggggcgc   1020
ggacacgagg ggcagcccgc ggcctggacg ttctgtttcc gtggcccgcg aggaaggcga   1080
ctgtcctgag gcgaggacc cagcggcaag atggcggcca gtggaagcc tgagggata    1140
ggcgagcggc cctgaggcgc tcgacggggt tggggggaa gcaggcccgc gaggcagctg   1200
cagccgggaa cgtgcggcca acccttatt tttttgacg ggttgcgggc cgtaggtgcc    1260
tccgaagtga gagccgtggg cgtttgactg tcggagagg tcggtcggat tttcatccgt   1320
tgctaaagac ggaagtgcga ctgagacggg aagggggggg agtcggttgg tggcggttga   1380
```

```
acctggacta aggcgcacat gacgtcgcgg tttctatggg ctcataatgg gtggtgagga   1440
catttccctg tttaaactta aacaagtttg tacaaaaaag caggctagat cttcaatatt   1500
ggccattagc catattattc attggttata tagcataaat caatattggc tattggccat   1560
tgcatacgtt gtatctatat cataatatgt acatttatat tggctcatgt ccaatatgac   1620
cgccatgttg gcattgatta ttgactagtt attaatagta atcaattacg gggtcattag   1680
ttcatagccc atatatggag ttccgcgtta cataacttac ggtaaatggc ccgcctggct   1740
gaccgcccaa cgaccccgc ccattgacgt caataatgac gtatgttccc atagtaacgc    1800
caatagggac tttccattga cgtcaatggg tggagtattt acggtaaact gcccacttgg   1860
cagtacatca agtgtatcat atgccaagtc cgcccctat tgacgtcaat gacggtaaat    1920
ggcccgcctg gcattatgcc cagtacatga ccttacggga cttcctact tggcagtaca    1980 tctacgtatt agtcatcgct attaccatag tgatgcggtt ttggcagtac accaatgggc   2040
gtggatagcg gtttgactca cggggatttc caagtctcca ccccattgac gtcaatggga   2100
gtttgttttg gcaccaaaat caacgggact ttccaaaatg tcgtaataac cccgccccgt   2160
tgacgcaaat gggcggtagg cgtgtacggt gggaggtcta tataagcaga gctcgtttag   2220
tgaaccgtca gatcactaga agcttcaagc tctagcagga agaagaaaga agaagaagaa   2280
gaagaagaag aagaagcgtc tcctcttctt cttgtgagag taaaaaagaa aactcccaaa   2340 aaaagaaaa tcatcaaaaa aacaaatttc aaaaagagtt tttgtgtttg gggattaaag    2400
aagaaaaaaa acaacaggtg agtaagcgca gttgtcgtct cttgcggtgc cgttgctggt   2460
tctcacacct tttaggtctg ttctcgtctt ccgttctgac tctctctttt tcgttgcagg   2520
cc                                                                  2522
```

<210> SEQ ID NO 74
<211> LENGTH: 3321
<212> TYPE: DNA
<213> ORGANISM: Artificial sequence
<220> FEATURE:
<223> OTHER INFORMATION: EEE1-Xt+CMV+TEE

<400> SEQUENCE: 74

```
tggtgaccct gtctcaaaaa accctcaaaa agtgttggga ttagtggcat gcaccaccat     60
tcccaccaaa ggtttatttt taataatatg tgtgtgagtg tgtatcacta tgagtatatg    120
tcaatatgtg tcaatgtccc cagggacatt taaagagccc ctgaagctgg agtcataggc    180
cattatgaac tgcctgacat ggctaatggg aattgaactc agattttctg gaagttatac    240
ctgctcttac tgctgagcca tgtctctgaa gaccccaggg attttttttt tttttttgaga    300 caggtattt ctgtatagcc ctggctgtcc tgaaagcact ctctatatgt agaccaggct     360
tgcctggagc ttggatatgc acctgcttct gcctcaggaa tggtgggatt gaaggtgtgc    420
accaccacat ccgctaacat gcacaattct taatgggttt atatcttatt taatgaatga    480
aaggtttggg ggatggatgt agcttaatgg aaaatgactg aagatttcaa ttaaaaatct    540
ggggcttagc tgcgcggtgg gtggtgcctg cctttagtcc cagtactggg gaggcagagg    600
aaggaggatc tctgtgagtt cgaggccagc tggtctataa cgtgagttcc aggacagcca    660
gagatacaca gacaaaccct gtctcaccaa acaaaacaa caacaacaac aacaaatctg    720
ggacgtaggc ttggtgtggt ggcacacatt ttgattccag cacttggaag gaagaggcct   780
gcatggtcta catagcttgt ttcaggcaac cagagctaca tagtgagatc ctgtctcaac   840
```

```
aaaaataaaa taatctaagg cttcaaaggg ttcaatctct taggtagcta aatatgaaca    900
aaatttggga aatgtgacct tttccttagt gacagtcaga tagaaccttc tcgagtgcaa    960
ggacaccaag tgcaaacagg ctcaagaaca gcctggaaag gtctagtgct atgggcttc   1020 aggtcgaatg ccaactgttt tcaagaactg tgtggatttt tctgcctgta acgaattcag   1080
attcattttt caaaactcgg ggagagtttt cccccttttat aatttttttt ttaaatttat   1140
taaactttgt ttcgttcccc ttgttttgag aattgcagag tcatccaccc tgtcacagtg   1200
ccagggagct cagggatggg cccaggggcc tggcggggct gaaggggctg gggaagcgag   1260
ggctccaaag gaccccagt gtggcaggag ccaaagccct aggtccctag aacgcagagg   1320
ccaccgggac cccccagacg gggtaagcgg gtgggtgtct ggggcgcgaa gccgcactgc   1380
gcatgcgccg aggtccgctc cggccgcgct gatccaagcc gggttctcgc gccgacctgg   1440
tcgtgattga caagtcacac acgctgatcc ctccgcgggg ccgcacaggg tcacagcctt   1500
tcccctcccc acaaagcccc ctactctctg ggcaccacac acgaacattc cttgagcgtg   1560
accttgttgg ctctagtcag gcgcctccgg tgcagagact ggaacggcct tgggaagtag   1620
tccctaaccg catttccgcg gagggatcgt cgggagggcg tggcttctga ggattatata   1680
aggcgactcc gggcgggtct tagctagttc cgtcggagac ccgagttcag tcgccgcttc   1740
tctgtgagga ctgctgccgc cgccgctggt gaggagaagc cgccgcgctt ggcgtagctg   1800
agagacgggg aggggggcgcg gacacgaggg gcagcccgcg gcctggacgt tctgtttccg   1860
tggcccgcga ggaaggcgac tgtcctgagg cggaggaccc agcggcaaga tggcggccaa   1920
gtggaagcct gaggggatag gcgagcggcc ctgaggcgct cgacggggtt ggggggggaag   1980 caggcccgcg aggcagctgc agccgggaac gtgcggccaa cccccttattt tttttgacgg   2040 gttgcgggcc gtaggtgcct ccgaagtgag agccgtgggc gtttgactgt cgggagaggt   2100
cggtcggatt ttcatccgtt gctaaagacg gaagtgcgac tgagacggga aggggggga   2160 gtcggttggt ggcggttgaa cctggactaa ggcgcacatg acgtcgcggt ttctatgggc   2220
tcataatggg tggtgaggac atttccctgt ttaaacttaa acaagtttgt acaaaaaagc   2280
aggctagatc ttcaatattg gccattagcc atattattca ttggttatat agcataaatc   2340
aatattggct attggccatt gcatacgttg tatctatatc ataatatgta catttatatt   2400
ggctcatgtc caatatgacc gccatgttgg cattgattat tgactagtta ttaatagtaa   2460
tcaattacgg ggtcattagt tcatagccca tatatggagt tccgcgttac ataacttacg   2520
gtaaatggcc cgcctggctg accgcccaac gaccccgcc cattgacgtc aataatgacg   2580
tatgttccca tagtaacgcc aatagggact ttccattgac gtcaatgggt ggagtattta   2640
cggtaaactg cccacttggc agtacatcaa gtgtatcata tgccaagtcc gccccctatt   2700
gacgtcaatg acggtaaatg gcccgcctgg cattatgccc agtacatgac cttacgggac   2760
tttcctactt ggcagtacat ctacgtatta gtcatcgcta ttaccatagt gatgcggttt   2820
tggcagtaca ccaatgggcg tggatagcgg tttgactcac ggggatttcc aagtctccac   2880
cccattgacg tcaatgggag tttgttttgg caccaaaatc aacgggactt tccaaaatgt   2940
cgtaataacc ccgccccgtt gacgcaaatg ggcggtaggc gtgtacggtg gaggtctat   3000 ataagcagag ctcgtttagt gaaccgtcag atcactagaa gcttcaagct ctagcaggaa   3060
gaagaaagaa gaagaagaag aagaagaaga agaagcgtct cctcttcttc ttgtgagagt   3120 aaaaagaaa actcccaaaa aaaagaaaat catcaaaaaa acaaatttca aaagagtttt   3180
ttgtgtttgg ggattaaaga agaaaaaaaa caacaggtga gtaagcgcag ttgtcgtctc   3240
```

```
ttgcggtgcc gttgctggtt ctcacacctt ttaggtctgt tctcgtcttc cgttctgact    3300
ctctcttttt cgttgcaggc c                                              3321

<210> SEQ ID NO 75
<211> LENGTH: 2232
<212> TYPE: DNA
<213> ORGANISM: Artificial sequence
<220> FEATURE:
<223> OTHER INFORMATION: EEE1-80+CMV+TEE

<400> SEQUENCE: 75
tcaaaactcg gggagagttt tcccccttta taattttttt tttaaattta ttaaactttg      60
tttcgttccc cttgttttga gaattgcaga gtcatccacc ctgtcacagt gccagggagc     120
tcagggatgg gccagggggc ctggcggggc tgaaggggct ggggaagcga gggctccaaa     180
gggaccccag tgtggcagga gccaaagccc taggtcccta gaacgcagag gccaccggga     240 cccccccagac ggggtaagcg ggtggtgtgtc tggggcgcga agccgcactg cgcatgcgcc   300
gaggtccgct ccggccgcgc tgatccaagc cgggttctcg cgccgacctg gtcgtgattg     360
acaagtcaca cacgctgatc cctccgcggg gccgcacagg gtcacagcct ttcccctccc     420
cacaaagccc cctactctct gggcaccaca cacgaacatt ccttgagcgt gaccttgttg     480
gctctagtca ggcgcctccg gtgcagagac tggaacggcc ttgggaagta gtccctaacc     540
gcatttccgc ggagggatcg tcgggagggc gtggcttctg aggattatat aaggcgactc     600
cgggcgggtc ttagctagtt ccgtcggaga cccgagttca gtcgccgctt ctctgtgagg     660
actgctgccg ccgccgctgg tgaggagaag ccgccgcgct tggcgtagct gagagacggg     720 gaggggggcgc ggacacgagg ggcagcccgc ggcctgacg ttctgtttcc gtggcccgcg     780
aggaaggcga ctgtcctgag gcggaggacc cagcggcaag atggcggcca agtggaagcc     840 tgagggggata ggcgagcggc cctgaggcgc tcgacgggt tgggggggaa gcaggcccgc    900
gaggcagctg cagccgggaa cgtgcggcca acccctattt tttttgacg ggttgcgggc     960 cgtaggtgcc tccgaagtga gagccgtggg cgtttgactg tcgggagagg tcggtcggat   1020
tttcatccgt tgctaaagac ggaagtgcga ctgagacggg aaggggggggg agtcggttgg   1080 tgcggttga acctggacta aggcgcacat gacgtcgcgg tttctatggg ctcataatgg    1140
gtggtgagga catttccctg tttaaactta aacaagtttg tacaaaaaag caggctagat   1200
cttcaatatt ggccattagc catattattc attggttata tagcataaat caatattggc   1260
tattggccat tgcatacgtt gtatctatat cataatatgt acatttatat tggctcatgt   1320
ccaatatgac cgccatgttg gcattgatta ttgactagtt attaatagta atcaattacg   1380
gggtcattag ttcatagccc atatatggag ttccgcgtta cataacttac ggtaaatggc   1440
ccgcctggct gaccgcccaa cgaccccgc ccattgacgt caataatgac gtatgttccc    1500
atagtaacgc caatagggac tttccattga cgtcaatggg tggagtattt acggtaaact   1560
gcccacttgg cagtacatca agtgtatcat atgccaagtc cgccccctat tgacgtcaat   1620
gacggtaaat ggcccgcctg gcattatgcc cagtacatga ccttacggga ctttcctact   1680
tggcagtaca tctacgtatt agtcatcgct attaccatag tgatgcggtt ttggcagtac   1740
accaatgggc gtggatagcg gtttgactca cggggatttc caagtctcca ccccattgac   1800
gtcaatggga gtttgttttg gcaccaaaat caacgggact ttccaaaatg tcgtaataac   1860
cccgccccgt tgacgcaaat gggcggtagg cgtgtacggt gggaggtcta tataagcaga   1920
```

| | |
|---|---:|
| gctcgtttag tgaaccgtca gatcactaga agcttcaagc tctagcagga agaagaaaga | 1980 |
| agaagaagaa gaagaagaag aagaagcgtc tcctcttctt cttgtgagag taaaaaagaa | 2040 |
| aactcccaaa aaaagaaaa tcatcaaaaa aacaaatttc aaaagagtt tttgtgtttg | 2100 |
| gggattaaag aagaaaaaaa acaacaggtg agtaagcgca gttgtcgtct cttgcggtgc | 2160 |
| cgttgctggt tctcacacct tttaggtctg ttctcgtctt ccgttctgac tctctcttt | 2220 |
| tcgttgcagg cc | 2232 |

```
<210> SEQ ID NO 76
<211> LENGTH: 1942
<212> TYPE: DNA
<213> ORGANISM: Artificial sequence
<220> FEATURE:
<223> OTHER INFORMATION: EEE1-60+CMV+TEE

<400> SEQUENCE: 76
```

| | |
|---|---:|
| cgcatgcgcc gaggtccgct ccggccgcgc tgatccaagc cgggttctcg cgccgacctg | 60 |
| gtcgtgattg acaagtcaca cacgctgatc cctccgcggg gccgcacagg gtcacagcct | 120 |
| ttcccctccc cacaaagccc cctactctct gggcaccaca cacgaacatt ccttgagcgt | 180 |
| gaccttgttg gctctagtca ggcgcctccg gtgcagagac tggaacggcc ttgggaagta | 240 |
| gtccctaacc gcatttccgc ggagggatcg tcgggagggc gtggcttctg aggattatat | 300 |
| aaggcgactc cgggcgggtc ttagctagtt ccgtcggaga cccagttca gtcgccgctt | 360 |
| ctctgtgagg actgctgccg ccgccgctgg tgaggagaag ccgccgcgct ggcgtagct | 420 |
| gagagacggg gaggggcgc ggacacgagg ggcagcccgc ggcctggacg ttctgtttcc | 480 |
| gtggcccgcg aggaaggcga ctgtcctgag gcggaggacc cagcggcaag atggcggcca | 540 |
| agtggaagcc tgaggggata ggcgagcggc cctgaggcgc tcgacggggt tgggggggaa | 600 |
| gcaggcccgc gaggcagctg cagccgggaa cgtgcggcca acccttatt tttttgacg | 660 |
| ggttgcggc cgtaggtgcc tccgaagtga gagccgtggg cgtttgactg tcgggagagg | 720 |
| tcggtcggat tttcatccgt tgctaaagac ggaagtgcga ctgagacggg aagggggggg | 780 |
| agtcggttgg tggcggttga acctggacta aggcgcacat gacgtcgcgg tttctatggg | 840 |
| ctcataatgg gtggtgagga catttccctg tttaaactta aacaagtttg tacaaaaaag | 900 |
| caggctagat cttcaatatt ggccattagc catattattc attggttata agcataaat | 960 |
| caatattggc tattggccat tgcatacgtt gtatctatat cataatatgt acatttatat | 1020 |
| tggctcatgt ccaatatgac cgccatgttg cattgatta ttgactagtt attaatagta | 1080 |
| atcaattacg gggtcattag ttcatagccc atatatggag ttccgcgtta cataacttac | 1140 |
| ggtaaatggc ccgcctggct gaccgcccaa cgacccccgc ccattgacgt caataatgac | 1200 |
| gtatgttccc atagtaacgc caatagggac tttccattga cgtcaatggg tggagtattt | 1260 |
| acggtaaact gcccacttgg cagtacatca agtgtatcat atgccaagtc cgcccctat | 1320 |
| tgacgtcaat gacggtaaat ggcccgcctg gcattatgcc cagtacatga ccttacggga | 1380 |
| ctttcctact tggcagtaca tctacgtatt agtcatcgct attaccatag tgatgcggtt | 1440 |
| ttggcagtac accaatgggc gtggatagcg gtttgactca cggggatttc caagtctcca | 1500 |
| ccccattgac gtcaatggga gtttgttttg gcaccaaaat caacgggact ttccaaaatg | 1560 |
| tcgtaataac cccgccccgt tgacgcaaat gggcggtagg cgtgtacggt gggaggtcta | 1620 |
| tataagcaga gctcgtttag tgaaccgtca gatcactaga agcttcaagc tctagcagga | 1680 |
| agaagaaaga agaagaagaa gaagaagaag aagaagcgtc tcctcttctt cttgtgagag | 1740 |

```
taaaaaagaa aactcccaaa aaaaagaaaa tcatcaaaaa aacaaatttc aaaaagagtt   1800
tttgtgtttg gggattaaag aagaaaaaaa acaacaggtg agtaagcgca gttgtcgtct   1860
cttgcggtgc cgttgctggt tctcacacct tttaggtctg ttctcgtctt ccgttctgac   1920
tctctctttt tcgttgcagg cc                                           1942

<210> SEQ ID NO 77
<211> LENGTH: 9513
<212> TYPE: DNA
<213> ORGANISM: Artificial sequence
<220> FEATURE:
<223> OTHER INFORMATION: pPNic384

<400> SEQUENCE: 77
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcgcca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aaccctact tgacagcaat    780 atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaagga tccaaacgat gagatttcct    960
tcaattttta ctgcagtttt attcgcggcc tcctcggcct tagctgctcc agtcaacact   1020
acaacagaag atgaaacggc acaaattccg gctgaagctg tcatcggtta ctcagattta   1080 gaagggggatt tcgatgttgc tgttttgcca ttttccaaca gcacaaataa cgggttattg   1140
tttataaata ctactattgc cagcattgct gctaaagaag aaggggtatc tctcgagaaa   1200
agagaggctg aagcttacgt agaattcgag ggtgctgtct tgcctagatc cgctaaagaa   1260
ttgagatgtc agtgtatcaa gacttactcc aagccattcc acccaaagtt catcaaagag   1320
ttgagagtta tcgagtccgg tccacactgt gctaacactg agatcatcgt taagttgtcc   1380
gacggtagag agttgtgttt ggacccaaaa gagaactggg ttcagagagt tgttgagaag   1440
ttcttgaaga gagctgagaa ctcctagtaa gcggccgcga attaattcgc cttagacatg   1500
actgttcctc agttcaagtt gggcacttac gagaagaccg tcttgctag attctaatca   1560 agaggatgtc agaatgccat ttgcctgaga gatgcaggct tcattttga tacttttta    1620 tttgtaacct atatagtata ggatttttt tgtcatttg tttcttctcg tacgagcttg     1680
ctcctgatca gcctatctcg cagctgatga atatcttgtg gtaggggttt gggaaaatca   1740
ttcgagtttg atgttttct tggtatttcc cactcctctt cagagtacag aagattaagt   1800
```

-continued

```
gagaagttcg tttgtgcaag cttatcgata agctttaatg cggtagttta tcacagttaa    1860
attgctaacg cagtcaggca ccgtgtatga aatctaacaa tgcgctcatc gtcatcctcg    1920
gcaccgtcac cctggatgct gtaggcatag gcttggttat gccggtactg ccgggcctct    1980
tgcgggatat cgtccattcc gacagcatcg ccagtcacta tggcgtgctg ctagcgctat    2040
atgcgttgat gcaatttcta tgcgcacccg ttctcggagc actgtccgac cgctttggcc    2100
gccgcccagt cctgctcgct cgctacttg  gagccactat cgactacgcg atcatggcga    2160
ccacacccgt cctgtggatc tatcgaatct aaatgtaagt taaaatctct aaataattaa    2220
ataagtccca gtttctccat acgaacctta acagcattgc ggtgagcatc tagaccttca    2280
acagcagcca gatccatcac tgcttggcca atatgtttca gtccctcagg agttacgtct    2340
tgtgaagtga tgaacttctg gaaggttgca gtgttaactc cgctgtattg acggcatat     2400
ccgtacgttg gcaaagtgtg gttggtaccg gaggagtaat ctccacaact ctctggagag    2460
taggcaccaa caaacacaga tccagcgtgt tgtacttgat caacataaga agaagcattc    2520
tcgatttgca ggatcaagtg ttcaggagcg tactgattgg acatttccaa agcctgctcg    2580
taggttgcaa ccgatagggt tgtagagtgt gcaatacact tgcgtacaat ttcaaccctt    2640
ggcaactgca cagcttggtt gtgaacagca tcttcaattc tggcaagctc cttgtctgtc    2700
atatcgacag ccaacagaat cacctgggaa tcaataccat gttcagcttg agacagaagg    2760
tctgaggcaa cgaaatctgg atcagcgtat ttatcagcaa taactagaac ttcagaaggc    2820
ccagcaggca tgtcaatact acacagggct gatgtgtcat tttgaaccat catcttggca    2880
gcagtaacga actggtttcc tggaccaaat attttgtcac acttaggaac agtttctgtt    2940
ccgtaagcca tagcagctac tgcctgggcg cctcctgcta gcacgataca cttagcacca    3000
accttgtggg caacgtagat gacttctggg gtaagggtac catccttctt aggtggagat    3060
gcaaaaacaa tttctttgca accagcaact ttggcaggaa cacccagcat cagggaagtg    3120
gaaggcagaa ttgcggttcc accaggaata tagaggccaa ctttctcaat aggtcttgca    3180
aaacgagagc agactacacc agggcaagtc tcaacttgca acgtctccgt tagttgagct    3240
tcatggaatt tcctgacgtt atctatagag agatcaatgg ctctcttaac gttatctggc    3300
aattgcataa gttcctctgg gaaaggagct tctaacacag gtgtcttcaa agcgactcca    3360
tcaaacttgg cagttagttc taaaagggct ttgtcaccat tttgacgaac attgtcgaca    3420
attggtttga ctaattccat aatctgttcc gttttctgga taggacgacg aagggcatct    3480
tcaatttctt gtgaggaggc cttagaaacg tcaattttgc acaattcaat acgaccttca    3540
gaagggactt ctttaggttt ggattcttct ttaggttgtt ccttggtgta tcctggcttg    3600
gcatctcctt tccttctagt gacctttagg gacttcatat ccaggtttct ctccacctcg    3660
tccaacgtca caccgtactt ggcacatcta actaatgcaa ataaaataa gtcagcacat    3720
tcccaggcta tatcttcctt ggatttagct tctgcaagtt catcagcttc cтcccтaаттт   3780
ttagcgttca acaaaacttc gtcgtcaaat aaccgtttgg tataagaacc ttctggagca    3840
ttgctcttac gatcccacaa ggtggcttcc atggctctaa gaccctttga ttggccaaaa    3900
caggaagtgc gttccaagtg acagaaacca acacctgttt gttcaaccac aaatttcaag    3960
cagtctccat cacaatccaa ttcgataccc agcaactttt gagttgctcc agatgtagca    4020
cctttatacc acaaaccgtg acgacgagat tggtagactc cagtttgtgt ccttatagcc    4080
tccggaatag acttttgga cgagtacacc aggcccaacg agтaатыgа agaгтcagcc     4140
accaaagtag tgaatagacc atcggggcgg tcagtagtca aagacgccaa caaaatttca    4200
```

```
ctgacaggga acttttgac atcttcagaa agttcgtatt cagtagtcaa ttgccgagca     4260
tcaataatgg ggattatacc agaagcaaca gtggaagtca catctaccaa ctttgcggtc    4320
tcagaaaaag cataaacagt tctactaccg ccattagtga aacttttcaa atcgcccagt    4380
ggagaagaaa aaggcacagc gatactagca ttagcgggca aggatgcaac tttatcaacc    4440
agggtcctat agataaccct agcgcctggg atcatccttt ggacaactct ttctgccaaa    4500
tctaggtcca aaatcacttc attgatacca ttattgtaca acttgagcaa gttgtcgatc    4560
agctcctcaa attggtcctc tgtaacggat gactcaactt gcacattaac ttgaagctca    4620
gtcgattgag tgaacttgat caggttgtgc agctggtcag cagcataggg aaacacggct    4680
tttcctacca aactcaagga attatcaaac tctgcaacac ttgcgtatgc aggtagcaag    4740
ggaaatgtca tacttgaagt cggacagtga gtgtagtctt gagaaattct gaagccgtat    4800
ttttattatc agtgagtcag tcatcaggag atcctctacg ccggacgcat cgtggccgac    4860
ctgcaggggg gggggggggcg ctgaggtctg cctcgtgaag aaggtgttgc tgactcatac   4920
caggcctgaa tcgccccatc atccagccag aaagtgaggg agccacggtt gatgagagct    4980
ttgttgtagg tggaccagtt ggtgattttg aacttttgct ttgccacgga acggtctgcg    5040
ttgtcgggaa gatgcgtgat ctgatccttc aactcagcaa aagttcgatt tattcaacaa    5100
agccgccgtc ccgtcaagtc agcgtaatgc tctgccagtg ttacaaccaa ttaaccaatt    5160
ctgattagaa aaactcatcg agcatcaaat gaaactgcaa tttattcata tcaggattat    5220
caataccata tttttgaaaa agccgtttct gtaatgaagg agaaaactca ccgaggcagt    5280
tccataggat ggcaagatcc tggtatcggt ctgcgattcc gactcgtcca acatcaatac    5340
aacctattaa tttcccctcg tcaaaaataa ggttatcaag tgagaaatca ccatgagtga    5400
cgactgaatc cggtgagaat ggcaaaagct tatgcatttc tttccagact tgttcaacag    5460
gccagccatt acgctcgtca tcaaaatcac tcgcatcaac caaaccgtta ttcattcgtg    5520
attgcgcctg agcgagacga atacgcgat cgctgttaaa aggacaatta caaacaggaa    5580
tcgaatgcaa ccggcgcagg aacactgcca gcgcatcaac aatatttca cctgaatcag    5640
gatattcttc taatacctgg aatgctgttt tcccggggat cgcagtggtg agtaaccatg    5700
catcatcagg agtacggata aaatgcttga tggtcggaag aggcataaat tccgtcagcc    5760
agtttagtct gaccatctca tctgtaacat cattggcaac gctacctttg ccatgtttca    5820
gaaacaactc tggcgcatcg ggcttccccat acaatcgata gattgtcgca cctgattgcc    5880
cgacattatc gcgagcccat ttatacccat ataaatcagc atccatgttg gaatttaatc    5940
gcggcctcga gcaagacgtt tcccgttgaa tatggctcat aacaccccctt gtattactgt    6000
ttatgtaagc agacagtttt attgttcatg atgatatatt tttatcttgt gcaatgtaac    6060
atcagagatt ttgagacaca acgtggcttt cccccccccc cctgcaggtc ggcatcaccg    6120
gcgccacagg tgcggttgct ggcgcctata tcgccgacat caccgatggg gaagatcggg    6180
ctcgccactt cgggctcatg agcgcttgtt tcggcgtggg tatggtggca ggccccgtgg    6240
ccggggact gttgggcgcc atctccttgc atgcaccatt ccttgcggcg gcggtgctca    6300
acggcctcaa cctactactg ggctgcttcc taatgcagga gtcgcataag ggagagcgtc    6360
gagtatctat gattggaagt atgggaatgg tgatacccgc attcttcagt gtcttgaggt    6420
ctcctatcag attatgccca actaaagcaa ccggaggagg agatttcatg gtaaatttct    6480
ctgactttg gtcatcagta gactcgaact gtgagactat ctcggttatg acagcagaaa    6540
```

```
tgtccttctt ggagacagta aatgaagtcc caccaataaa gaaatccttg ttatcaggaa    6600
caaacttctt gtttcgaact ttttcggtgc cttgaactat aaaatgtaga gtggatatgt    6660
cgggtaggaa tggagcgggc aaatgcttac cttctggacc ttcaagaggt atgtagggtt    6720
tgtagatact gatgccaact tcagtgacaa cgttgctatt tcgttcaaac cattccgaat    6780
ccagagaaat caaagttgtt tgtctactat tgatccaagc cagtgcggtc ttgaaactga    6840
caatagtgtg ctcgtgtttt gaggtcatct ttgtatgaat aaatctagtc tttgatctaa    6900
ataatcttga cgagccaagg cgataaatac ccaaatctaa aactctttta aaacgttaaa    6960
aggacaagta tgtctgcctg tattaaaccc caaatcagct cgtagtctga tcctcatcaa    7020 cttgagggc actatcttgt tttagagaaa tttgcggaga tgcgatatcg agaaaaggt     7080 acgctgattt taaacgtgaa atttatctca agatctctgc ctcgcgcgtt tcggtgatga    7140
cggtgaaaac ctctgacaca tgcagctccc ggagacggtc acagcttgtc tgtaagcgga    7200
tgccgggagc agacaagccc gtcagggcgc gtcagcgggt gttggcgggt gtcggggcgc    7260
agccatgacc cagtcacgta gcgatagcgg agtgtatact ggcttaacta tgcggcatca    7320
gagcagattg tactgagagt gcaccatatg cggtgtgaaa taccgcacag atgcgtaagg    7380
agaaaatacc gcatcaggcg ctcttccgct tcctcgctca ctgactcgct gcgctcggtc    7440
gttcggctgc ggcgagcggt atcagctcac tcaaaggcgg taatacggtt atccacagaa    7500 tcagggggata acgcaggaaa gaacatgtga gcaaaaggcc agcaaaaggc caggaaccgt    7560
aaaaaggccg cgttgctggc gtttttccat aggctccgcc cccctgacga gcatcacaaa    7620
aatcgacgct caagtcagag gtggcgaaac ccgacaggac tataaagata ccaggcgttt    7680
ccccctggaa gctccctcgt gcgctctcct gttccgaccc tgccgcttac cggatacctg    7740
tccgcctttc tcccttcggg aagcgtggcg ctttctcaat gctcacgctg taggtatctc    7800
agttcggtgt aggtcgttcg ctccaagctg ggctgtgtgc acgaaccccc cgttcagccc    7860
gaccgctgcg ccttatccgg taactatcgt cttgagtcca acccggtaag acacgactta    7920
tcgccactgg cagcagccac tggtaacagg attagcagag cgaggtatgt aggcggtgct    7980
acagagttct tgaagtggtg gcctaactac ggctacacta aaggacagt atttggtatc     8040 tgcgctctgc tgaagccagt taccttcgga aaaagagttg gtagctcttg atccggcaaa    8100
caaaccaccg ctggtagcgg tggtttttt gtttgcaagc agcagattac gcgcagaaaa     8160
aaaggatctc aagaagatcc tttgatcttt tctacggggt ctgacgctca gtggaacgaa    8220
aactcacgtt aagggatttt ggtcatgaga ttatcaaaaa ggatcttcac ctagatcctt    8280
ttaaattaaa aatgaagttt taaatcaatc taaagtatat atgagtaaac ttggtctgac    8340
agttaccaat gcttaatcag tgaggcacct atctcagcga tctgtctatt tcgttcatcc    8400
atagttgcct gactccccgt cgtgtagata actacgatac gggagggctt accatctggc    8460
cccagtgctg caatgatacc gcgagaccca cgctcaccgg ctccagattt atcagcaata    8520
aaccagccag ccggaagggc cgagcgcaga agtggtcctg caactttatc cgcctccatc    8580
cagtctatta attgttgccg ggaagctaga gtaagtagtt cgccagttaa tagtttgcgc    8640
aacgttgttg ccattgctgc aggcatcgtg gtgtcacgct cgtcgtttgg tatggcttca    8700
ttcagctccg gttcccaacg atcaaggcga gttacatgat ccccatgtt gtgcaaaaaa     8760 gcggttagct ccttcggtcc tccgatcgtt gtcagaagta agttggccgc agtgttatca    8820
ctcatggtta tggcagcact gcataattct cttactgtca tgccatccgt aagatgcttt    8880
tctgtgactg gtgagtactc aaccaagtca ttctgagaat agtgtatgcg gcgaccgagt    8940
```

```
tgctcttgcc cggcgtcaac acgggataat accgcgccac atagcagaac tttaaaagtg    9000
ctcatcattg gaaaacgttc ttcggggcga aaactctcaa ggatcttacc gctgttgaga    9060
tccagttcga tgtaacccac tcgtgcaccc aactgatctt cagcatcttt tactttcacc    9120
agcgtttctg ggtgagcaaa aacaggaagg caaaatgccg caaaaagggg aataagggcg    9180
acacggaaat gttgaatact catactcttc cttttcaat attattgaag catttatcag     9240
ggttattgtc tcatgagcgg atacatattt gaatgtattt agaaaataa acaaataggg     9300 gttccgcgca catttccccg aaaagtgcca cctgacgtct aagaaaccat tattatcatg    9360
acattaacct ataaaaatag gcgtatcacg aggccctttc gtcttcaaga attaattctc    9420
atgtttgaca gcttatcatc gataagctga ctcatgttgg tattgtgaaa tagacgcaga    9480
tcgggaacac tgaaaaataa cagttattat tcg                                 9513
```

<210> SEQ ID NO 78
<211> LENGTH: 1720
<212> TYPE: DNA
<213> ORGANISM: Artificial sequence
<220> FEATURE:
<223> OTHER INFORMATION: pPNic602 insert

<400> SEQUENCE: 78

```
cctgacgtct aagaaaccat tattatcatg acattaacct ataaaaatag gcgtatcacg      60
aggccctttc gtcttcaaga attaattctc atgtttgaca gcttatcatc gataagctga     120
ctcatgttgg tattgtgaaa tagacgcaga tcgggaacac tgaaaaataa cagttattat    180
tcgtttcagg caaccagagc tacatagtga gatcctgtct caacaaaaat aaaataatct    240
aaggcttcaa agggttcaat ctcttaggta gctaaatatg aacaaaattt gggaaatgtg    300 acctttttcct tagtgacagt cagatagaac cttctcgagt gcaaggacac caagtgcaaa    360
caggctcaag aacagcctgg aaaggtctag tgctatgggg cttcaggtcg aatgccaact    420
gttttcaaga actgtgtgga ttttttctgcc tgtaacgaat tcagattcat ttttcaaaac     480
tcggggagag ttttccccct ttataatttt ttttttaaat ttattaaact ttgtttcgtt    540
ccccttgttt tgagaattgc agagtcatcc accctgtcac agtgccaggg agctcaggga    600
tgggcccagg ggcctggcgg ggctgaaggg gctggggaag cgagggctcc aaagggaccc    660
cagtgtggca ggagccaaag ccctaggtcc ctagaacgca gaggccaccg ggaccccca     720 gacggggtaa gcgggtgggt gtctgggcg cgaagccgca ctgcgcatgc gccgaggtcc      780
gctccggccc cgctgatcca agccgggttc tcgcgccgac ctggtcgtga ttgacaagtc    840
acacacgctg atccctccgc ggggccgcac agggtcacag cctttcccct ccccacaaag    900 cccctactc tctgggcacc acacgaac attccttgag cgtgaccttg ttggctctag      960
tcaggcgcct ccggtgcaga gactggaacg gccttgggaa gtagtcccta accgcatttc    1020
cgcggaggga tcgtcgggag ggcgtggctt ctgaggatta tataaggcga ctccgggcgg    1080
gtcttagcta gttccgtcgg agacccgagt tcagtcgccg cttctctgtg aggactgctg    1140
ccgccgccgc tggtgaggag aagccgccgc gcttggcgta gctgagagac ggggaggggg    1200
cgcggacacg aggggcagcc cgcggcctgg acgttctgtt tccgtggccc gcgaggaagg    1260
cgactgtcct gaggcggagg acccagcggc aagatggcgg ccaagtggaa gcctgagggg    1320
ataggcgagc ggccctgagg cgctcgacgg ggttgggggg gaagcaggcc cgcgaggcag    1380
ctgcagccgg gaacgtgcgg ccaaccccctt attttttttg acgggttgcg ggccgtaggt    1440
```

```
gcctccgaag tgagagccgt gggcgtttga ctgtcgggag aggtcggtcg gattttcatc    1500
cgttgctaaa gacggaagtg cgactgagac gggaaggggg gggagtcggt tggtggcggt    1560
tgaacctgga ctaaggcgca catgacgacg cggtttctat gggctcataa tgggtggtga    1620
ggacatttcc ctagatctaa catccaaaga cgaaaggttg aatgaaacct ttttgccatc    1680
cgacatccac aggtccattc tcacacataa gtgccaaacg                          1720

<210> SEQ ID NO 79
<211> LENGTH: 455
<212> TYPE: DNA
<213> ORGANISM: Artificial sequence
<220> FEATURE:
<223> OTHER INFORMATION: EF1a promoter

<400> SEQUENCE: 79
ggatccttgg agctaagcca gcaatggtag agggaagatt ctgcacgtcc cttccaggcg     60
gcctccccgt caccaccccc cccaacccgc cccgaccgga gctgagagta attcatacaa    120
aaggactcgc ccctgccttg gggaatccca ggaccgtcg ttaaactccc actaacgtag     180
aacccagaga tcgctgcgtt cccgcccccct cacccgcccg ctctcgtcat cactgaggtg    240
gagaagagca tgcgtgaggc tccggtgccc gtcagtgggc agagcgcaca tcgcccacag    300
tccccgagaa gttgggggga ggggtcggca attgaaccgg tgcctagaga aggtggcgcg    360
gggtaaactg ggaaagtgat gtcgtgtact ggctccgcct ttttcccgag ggtgggggag    420
aaccgtatat aagtgcagta gtcgccgtga acgtt                               455

<210> SEQ ID NO 80
<211> LENGTH: 2250
<212> TYPE: DNA
<213> ORGANISM: Artificial sequence
<220> FEATURE:
<223> OTHER INFORMATION: EEE1-A1

<400> SEQUENCE: 80
tgcagtgcca gacactacat agcctgatat actctagtgt taactgagaa ggagcaccat     60
tcccaccata ccttaaatat aatttaaaag agagagtgtg agaaactcaa agtgaacaag    120
actaaaagag actaagacac aaggcagaat aatacactcc ctcatggtgc tgactttgcc    180
caatttcatc aggcagtctt gggttaagcc taatcatcac tgttatacag catgattttg    240
gtccacattc aggtcaccca agacacagta cagggctggg ttttatatat tgatatcaca    300
gaggaaatat gtcttttggc ctgggtctgc agtatggagt gtgttttctt tgtgcagggt    360
aggcagcacc atgcttttcc tcctccttct gcctcagcat tggagggtta gtaggagagg    420
agctctagaa ccggttagaa ggagattaca taatcctttt ttatcctatt atatgaatga    480
aagatttggc ctatgttctt ggcttttggg ataatgactt acaatactac ttatggttgt    540
ggcccttacc agcgcggtgg gtggtgcgct gcttttagtc ctgatattgg ggaggcagag    600
gaaggaggat cactctcact acgtgggcac ctggtgtttt acgagactac cacctctggc    660
tgtgttacag tgaatagcac agaccctacc aatgcatata acaacaacta gatctattgt    720
gccacgaagg gtagctctcc agcctctctt atagttagga cctcatggaa ggaagagggc    780
aggaagctgt tctttggtag atacacctaa ctagagttca ttagtgagtg catgcaccta    840
atataaatat ttgatctaag gagcataggc tactaatctc ttaggtggtt attttcactt    900
ctatatttgg gaaagagtcc tatacccctag ctaaagttac aaagaacctt ctcgactcct    960
aggtctggaa gtgcaaaagg gtgaaagaac agctgctatg ctgttgaggt ttggcccctt   1020
```

```
cccctcgtaa ggctagtcta tactacatca gagagcaata tacaggcaga atcgtaatga   1080
catacttata cctatacacg ggcacactat accccataaa attatacttt agagcaataa   1140
attatcatag atacgatggg catctatagg taattctatg accatccacc ctgcatctgt   1200
ggctgcctgg tgaggcaagc ccccaggggg cagccgggcc agtagcccct ggggtaccgt   1260
ggggtgctat gcctccccac tctggaggt ggctatgggg ttgctgcttt gtacggacag    1320
ggctccggga ccccctgtc ggccttaccg gcagggagac aggcccgcgt agccggagtc    1380
cggaagcgcc gtggtgcggt gcgcccgcgc tgatcctacc cgctatgtcg cgccgtcctg   1440
gacgagttag tctactgaga gacgctgatc cctccgcggg gcccggagac actgagaccc   1500
tatgcccacc ctagattacc cctcaatctc tgggcaccac acacgaacat tccttgagcg   1560
tgaccttgtt ggctctagtc aggcgcctcc ggtgcagaga ctggaacggc cttgggaagt   1620
agtccctaac cgcatttccg cggagggatc gtcgggaggg cgtggcttct gaggattata   1680
taaggcgact ccggggcggt cttagctagt tccgtcggag acccgagttc agtcgccgct   1740
tctctgtgag gactgctgcc gccgccgctg gtgaggagaa gccgccgcgc ttggcgtagc   1800
tgagagacgg ggaggggggcg cggacacgag gggcagcccg cggcctggac gttctgtttc   1860
cgtggcccgc gaggaaggcg actgtcctga ggcggaggac ccagcggcaa gatggcggcc   1920
aagtggaagc ctgaggggat aggcgagcgg ccctgaggcg ctcgacgggg ttgggggggga  1980 agcaggcccg cgaggcagct gcagccggga acgtgcggcc aaccccttat ttttttgac   2040 gggttgcggg ccgtaggtgc ctccgaagtg agagccgtgg gcgtttgact gtcgggagag   2100
gtcggtcgga tttttcatccg ttgctaaaga cggaagtgcg actgagacgg aaggggggg   2160 gagtcggttg gtggcggttg aacctggact aaggcgcaca tgacgtcgcg gtttctatgg   2220
gctcataatg ggtggtgagg acatttccct                                    2250
```

<210> SEQ ID NO 81
<211> LENGTH: 1449
<212> TYPE: DNA
<213> ORGANISM: Artificial sequence
<220> FEATURE:
<223> OTHER INFORMATION: EEE1-A2

<400> SEQUENCE: 81

```
tttcaggcaa ccagagctac atagtgagat cctgtctcaa caaaaataaa ataatctaag    60
gcttcaaagg gttcaatctc ttaggtagct aaatatgaac aaaatttggg aaatgtgacc   120
ttttccttag tgacagtcag atagaacctt ctcgagtgca aggacaccaa gtgcaaacag   180
gctcaagaac agcctggaaa ggtctagtgc tatgggctt caggtcgaat gccaactgtt    240
ttcaagaact gtgtggatt ttctgcctgt aacgaattca gattcatttt tcaaaactcg    300
gggagagttt tccccctta taatttttttt tttaaattta ttaaactttg tttcgttccc   360
cttgttttga gaattgcaga gtcatccacc ctgtcacagt gccagggagc tcagggatgg   420
gcccaggggc ctggcgggc tgaagggct ggggaagcga gggctccaaa gggaccccag    480
tgtggcagga gccaaagccc taggtcccta gaacgcagag gccaccggga ccccccagac   540
ggggtaagcg ggtgggtgtc tggggcgcga agccgcactg cgcatgcgcc gaggtccgct   600
ccggccgcgc tgatccaagc cgggttctcg cgccgacctg gtcgtgattg acaagtcaca   660
cacgctgatc cctccgcggg gccgcacagg gtcacagcct ttcccctccc cacaaagccc   720
cctactgtct ggccatctct ctcgtagaat gcatcaccga gtgctagatg ccacaactga   780
```

| | |
|---|---|
| cccgcctccg ctcctgtgtc agcataggcc ttgggaagta gtcctttagc ggaataccgc | 840 |
| gcaccgttcg acgtgagggc gtggctattg aggattatat aaggcgtcac cgcccggctg | 900 |
| taacctagtt ccgtcgcaca gccgagagta cccgccgctt ctcagagtgc agtccaggcg | 960 |
| ccgccgctgg tgaggagaag ccgccgcgct tggcgtagct gagagacggg gaggggcgc | 1020 |
| ggacacgagg ggcagcccgc ggcctggacg ttctgtttcc gtggcccgcg aggaaggcga | 1080 |
| ctgtcctgag gcgaggacc cagcggcaag atggcggcca agtggaagcc tgaggggata | 1140 |
| ggcgagcggc cctgaggcgc tcgacggggt tggggggggaa gcaggcccgc gaggcagctg | 1200 |
| cagccgggaa cgtgcggcca acccttatt tttttgacg ggttgcgggc cgtaggtgcc | 1260 |
| tccgaagtga gagccgtggg cgtttgactg tcggagagg tcggtcggat tttcatccgt | 1320 |
| tgctaaagac ggaagtgcga ctgagacggg aagggggggg agtcggttgg tggcggttga | 1380 |
| acctggacta aggcgcacat gacgtcgcgg tttctatggg ctcataatgg gtggtgagga | 1440 |
| catttccct | 1449 |

<210> SEQ ID NO 82
<211> LENGTH: 1449
<212> TYPE: DNA
<213> ORGANISM: Artificial sequence
<220> FEATURE:
<223> OTHER INFORMATION: EEE1-A3

<400> SEQUENCE: 82

| | |
|---|---|
| tttcaggcaa ccagagctac atagtgagat cctgtctcaa caaaaataaa ataatctaag | 60 |
| gcttcaaagg gttcaatctc ttaggtagct aaatatgaac aaaatttggg aaatgtgacc | 120 |
| ttttccttag tgacagtcag atagaaacctt ctcgagtgca aggacaccaa gtgcaaacag | 180 |
| gctcaagaac agcctggaaa ggtctagtgc tatgggctt caggtcgaat gccaactgtt | 240 |
| ttcaagaact gtgtggattt ttctgcctgt aacgaattca gattcatttt tcaaaactcg | 300 |
| gggagagttt tccccccttta taattttttt tttaaattta ttaaactttg tttcgttccc | 360 |
| cttgttttga gaattgcaga gtcatccacc ctgtcacagt gccagggagc tcaggatgg | 420 |
| gcccaggggc ctggcgggc tgaaggggct ggggaagcga gggctccaaa gggaccccag | 480 |
| tgtggcagga gccaaagccc taggtcccta gaacgcagag gccaccggga cccccagac | 540 |
| ggggtaagcg ggtgggtgtc tggggcgcga agccgcactg cgcatgcgcc gaggtccgct | 600 |
| ccggccgcgc tgatccaagc cgggttctcg cgccgacctg gtcgtgattg acaagtcaca | 660 |
| cacgctgatc cctccgcggg gccgcacagg gtcacagcct ttcccctccc cacaaagccc | 720 |
| cctactctct gggcaccaca cacgaacatt ccttgagcgt gaccttgttg gctctagtca | 780 |
| ggcgcctccg gtgcagagac tggaacggcc ttgggaagta gtccctaacc gcatttccgc | 840 |
| ggagggatcg tcgggagggc gtggcttctg aggattatat aaggcgactc cgggcgggtc | 900 |
| ttagctagtt ccgtcggaga cccgagttca gtcgccgctt ctctgtgagg actgctgccg | 960 |
| ccgccgctgg tgaggtcaat ccgccgcggt agccgattgt ctctctcggg gagggccgc | 1020 |
| gctgtcgtcc cctggggcgc ggggacctcg aagacaaagc gacctgcgcg aggaaggcga | 1080 |
| ctgtcctgag gcgaggtgc ctccggcaag atggcgctgt tcacctttgg actccccatt | 1140 |
| cccgtccggg ggactcccgg acgtcgccca acccccccctt cgtccggcgc gtccctccac | 1200 |
| tgctcgcctt cgaccgccct tggggaattt ttttttctcg ggttgcgggc cgatccaccc | 1260 |
| agcgttcact ctcccgtggg cgtttgtgac acgcctctcc acgtcgcta aaagtagcgt | 1320 |
| tgctaaagac gcttcaccgt gactgacggg aaggggggggg agtcgcaacc accccggttct | 1380 |

| tggacctgaa aggcggtgta ctcgtcgcgc aaagataccc gactggggtt ttggtgagga | 1440 |
| catttccct | 1449 |

<210> SEQ ID NO 83
<211> LENGTH: 1449
<212> TYPE: DNA
<213> ORGANISM: Artificial sequence
<220> FEATURE:
<223> OTHER INFORMATION: EEE1-B1

<400> SEQUENCE: 83

| tttcaggcaa ccagagctac atagtgagat cctgtctcaa caaaaataaa ataatctaag | 60 |
| gcttcaaagg gttcaatctc ttaggtagct aaatatgaac aaaatttggg aaatgtgacc | 120 |
| ttttccttag tgacagtcag ataactgcat tccgagtgca aggacaccaa gtgcaaacag | 180 |
| gctcaagaac agcctggaaa ggtctagtgc tatggggctt caggtcgaat gccaactgtt | 240 |
| ttcaagaact gtgtggattt ttctgcctgt aacgaattca gattcatttt tcaaaactcg | 300 |
| gggagagttt tcccccttta aatttttttt tttaaattta ttaaactttg tttcgttccc | 360 |
| cttgttttga gaattgcaga gtcatccacc ctgtcacagt gccagggagc tcagggatgg | 420 |
| gcccaggggc ctggcggggc tgaaggggct ggggaagcga gggctccaaa gggaccccag | 480 |
| tgtggcagga gccaaagccc taggtcccta gaacgcagag gccaccggga ccccccagac | 540 |
| ggggtaagcg ggtgggtgtc tggggcgcga agccgcactg cgcatgcgcc gaggtccgct | 600 |
| ccggccgcgc ttgcacaagc cgggttctcg cgccgacctg gtcgtgattg acaagtcaca | 660 |
| cacgcttgca cctccgcggg gccgcacagg gtcacagcct ttcccctccc cacaaagccc | 720 |
| cctactctct gggcaccaca cacgaacatt ccttgagcgt gaccttgttg gctctagtca | 780 |
| ggcgcctccg gtgcagagac tggaacggcc ttgggctgag atacctaacc gcatttccgc | 840 |
| ggagggatcg tcgggagggc gtggcttctg aggattatat aaggcgactc cgggcgggtc | 900 |
| ttagctagtt ccgtcggaga cccgagttca gtcgccgctt ctctgtgagg actgctgccg | 960 |
| ccgccgctgg tgaggagaag ccgccgcgct tggcgtagct gagagacggg gaggggcgc | 1020 |
| ggacacgagg ggcagcccgc ggcctggacg ttctgtttcc gtggcccgcg aggaaggcga | 1080 |
| ctgtcctgag gcggaggacc cagcgtagag caggcggcca agtggaagcc tgagggata | 1140 |
| ggcgagcggc cctgaggcgc tcgacggggt tggggggaa gcaggcccgc gaggcagctg | 1200 |
| cagccgggaa cgtgcggcca acccttatt ttttttgacg ggttgcgggc cgtaggtgcc | 1260 |
| tccgaagtga gagccgtggg cgtttgactg tcgggagagg tcggtcggat tttcatccgt | 1320 |
| tgctaaagac ggaagtgcga ctgagacggg aaggggggggg agtcggttgg tggcggttga | 1380 |
| acctggacta aggcgcacat gacgtcgcgg tttctatggg ctcataatgg gagggtgtga | 1440 |
| catttccct | 1449 |

<210> SEQ ID NO 84
<211> LENGTH: 1449
<212> TYPE: DNA
<213> ORGANISM: Artificial sequence
<220> FEATURE:
<223> OTHER INFORMATION: EEE1-B2

<400> SEQUENCE: 84

| tttcaggcaa ccagagctac atagtgagat cctgtctcaa caaaaataaa ataatctaag | 60 |
| gcttcaaagg gttcaatctc ttaggtagct aaatatgaac aaaatttggg aaatgtgacc | 120 |

| | |
|---|---|
| ttttccttag tgacagtcag atagaacctt ctcgagtgca aggacaccaa gtgcaaacag | 180 |
| gctcaagaac agcctggaaa ggtctagtgc tatggggctt caggtccaat gccaactgtt | 240 |
| ttcaagaact gtgtggattt ttctgcctgt aaccaattca gattcatttt tcaaaactgg | 300 |
| gggagagttt tcccccttta aattttttt tttaaattta ttaaactttg tttccttccc | 360 |
| cttgttttga gaattgcaga gtcatccacc ctgtcacagt gccagggagc tcagggatgg | 420 |
| gcccaggggc ctgggggggc tgaaggggct ggggaagcca ggctccaaa ggaccccag | 480 |
| tgtggcagga gccaaagccc taggtcccta gaacccagag gccaccggga cccccagac | 540 |
| ggggtaaggg ggtgggtgtc tggggcccca agcccactg cccatgggcc caggtccct | 600 |
| ccggccgcgc tgatccaagc cgggttctgg ccccacctg gtggtgattg acaagtcaca | 660 |
| cacgctgatc cctccgcggg gccgcacagg gtcacagcct ttcccctccc cacaaagccc | 720 |
| cctactctct gggcaccaca caggaacatt ccttgagcct gaccttgttg gctctagtca | 780 |
| ggggcctccg gtgcagagac tggaacggcc ttgggaagta gtccctaacc gcatttcccc | 840 |
| ggagggatcg tcgggagggc gtggcttctg aggattatat aaggccactc ctgggggtc | 900 |
| ttagctagtt ccctgggaga ccccagttca gtccccctt ctctgtgagg actgctgccc | 960 |
| ccgccgctgg tgaggagaag cccctcgct tggcgtagct gagagacggg gaggggcgc | 1020 |
| ggacacgagg ggcagccccc tgcctggacc ttctgtttcc gtggcccgcg aggaaggcga | 1080 |
| ctgtcctgag gcggaggacc cagcggcaag atggcggcca gtggaagcc tgaggggata | 1140 |
| ggccaggggc cctgaggccc tccagggggt tgggggggaa gcaggcccgc caggcagctg | 1200 |
| cagctgggaa cctgcggcca acccttatt tttttgacg ggttggggc cgtaggtgcc | 1260 |
| tccgaagtga gagccgtggg cgtttgactg tcgggagagg tcggtcggat tttcatccgt | 1320 |
| tgctaaagac ggaagtgcga ctgagacggg aagggggggg agtcggttgg tggggttga | 1380 |
| acctggacta aggcccacat gacgtccctg tttctatggg ctcataatgg gtggtgagga | 1440 |
| catttccct | 1449 |

<210> SEQ ID NO 85
<211> LENGTH: 1449
<212> TYPE: DNA
<213> ORGANISM: Artificial sequence
<220> FEATURE:
<223> OTHER INFORMATION: EEE1-B3

<400> SEQUENCE: 85

| | |
|---|---|
| tttcaggcaa ccagagctac atagtgagat cctgtctcaa caaaaataaa ataatctaag | 60 |
| gcttcaaagg gttcaatctc ttaggtagct aaatatgaac aaaatttggg aaatgtgacc | 120 |
| ttttccttag tgacagtcag atagaacctt ctcgagtgca aggacaccaa gtgcaaacag | 180 |
| gctcaagaac agcctggaaa ggtctagtgc tatggggctt caggtcgaat gccaactgtt | 240 |
| ttcaagaact gtgtggattt ttctgcctgt aacgaattca gattcatttt tcaaaactcg | 300 |
| gggagagttt tcccccttta aattttttt tttaaattta ttaaactttg tttcgttccc | 360 |
| cttgttttga gaattgcaga gtcatccacc ctgtcacagt gccagggagc tcagggatgg | 420 |
| gcccaggggc ctggcgggc tgaaggggct ggggaagcga ggctccaaa ggaccccag | 480 |
| tgtggcagga gccaaagccc taggtcccta gaacgcagag gccaccggga cccccagac | 540 |
| ggggtaagcg ggtgggtgtc tggggcgcca agcccactg cccatgcgcc gaggtccct | 600 |
| cctgccgcgc tgatccaagc cgggttctcg cgccgacctg gtcgtgattg acaagtcaca | 660 |
| cacgctgatc cctccgcggg gccgcacagg gtcacagcct ttcccctccc cacaaagccc | 720 |

```
cctactctct gggcaccaca cacgaacatt ccttgagcgt gaccttgttg gctctagtca    780
ggcgcctccg gtgcagagac tggaacggcc ttgggaagta gtccctaacc gcatttccgc    840
ggagggatcg tcgggagggc gtggcttctg aggattatat aaggcgactc cggcgggtc     900
ttagctagtt ccgtcggaga cccgagttca gtcgccgctt ctctgtgagg actgctgccg    960
ccgccgctgg tgaggagaag ccgccgcgct tggcgtagct gagagacggg gaggggcgc    1020
ggacacgagg ggcagcccgc ggcctggacg ttctgtttcc gtggcccgcg aggaaggcga   1080
ctgtcctgag gcggaggacc cagcggcaag atggcggcca gtggaagcc tgaggggata    1140
ggcgagcggc cctgaggcgc tcgacggggt tgggggggaa gcaggcccgc gaggcagctg   1200
cagccgggaa cgtgcggcca acccttatt tttttgacg ggttgcgggc cgtaggtgcc    1260
tccgaagtga gagccgtggg cgtttgactg tcggagagg tcggtcggat tttcatccgt    1320
tgctaaagac ggaagtgcga ctgagacggg aagggggggg agtcggttgg tggcggttga   1380
acctggacta aggcgcacat gacgtcgcgg tttctatggg ctcataatgg gtggtgagga   1440
catttccct                                                            1449

<210> SEQ ID NO 86
<211> LENGTH: 1449
<212> TYPE: DNA
<213> ORGANISM: Artificial sequence
<220> FEATURE:
<223> OTHER INFORMATION: EEE1-B4

<400> SEQUENCE: 86
tttcaggcaa ccagagctac atagtgagat cctgtctcaa caaaaataaa ataatctaag     60
gcttcaaagg gttcaatctc ttaggtagct aaatatgaac aaaatttggg aaatgtgacc    120
ttttccttag tgacagtcag atagaacctt ctcgagtgca aggacaccaa gtgcaaacag    180
gctcaagaac agcctggaaa ggtctagtgc tatgggcctt caggtccaat gccaactgtt    240
ttcaagaact gtgtggattt ttctgcctgt aaggaattca gattcatttt tcaaaactcg    300
gggagagttt tcccccttta taattttttt tttaaattta ttaaactttg tttccttccc    360
cttgttttga gaattgcaga gtcatccacc ctgtcacagt gccagggagc tcaggatgg    420
gcccaggggc ctggggggc tgaaggggct ggggaaggga gggctccaaa gggaccccag   480
tgtggcagga gccaaagccc taggtcccta gaacccagag gccaccggga ccccccagag   540
ggggtaagcg ggtgggtgtc tggggcccga agccccactg cgcatgcccc gaggtcccct   600
ccggcccccgc tgatccaagc ctggttctcg ccccgacctg gtcgtgattg acaagtcaca   660
cacgctgatc cctccgcggg gccccacagg gtcacagcct ttcccctccc cacaaagccc   720
cctactctct gggcaccaca caccaacatt ccttgagcgt gaccttgttg gctctagtca   780
ggggcctccg gtgcagagac tggaagggcc ttgggaagta gtccctaacc gcatttcccc   840
ggagggatcc tcgggagggg gtggcttctg aggattatat aaggccactc cggcgggtc    900
ttagctagtt ccctcggaga cccagttca gtcgcccctt ctctgtgagg actgctgccg   960
ccccccgctgg tgaggagaag ccccgcccct tgggtagct gagagacggg gaggggccc   1020
ggacaggagg ggcagcccgg ggcctggacg ttctgtttcc ctggcccgcg aggaaggcca   1080
ctgtcctgag gggaggacc cagcggcaag atggcggcca gtggaagcc tgaggggata    1140
ggcgaggggc cctgaggcgc tccacggggt tgggggggaa gcaggccccc gaggcagctg   1200
cagcctggaa cgtgggggcca acccttatt tttttgacg ggttgggggc cgtaggtgcc   1260
```

| | |
|---|---|
| tcccaagtga gagccctggg cctttgactg tcgggagagg tcggtcggat tttcatccct | 1320 |
| tgctaaagag ggaagtggga ctgagacggg aaggggggggg agtgggttgg tggcggttga | 1380 |
| acctggacta aggggcacat gacgtcccgg tttctatggg ctcataatgg gtggtgagga | 1440 |
| catttccct | 1449 |

<210> SEQ ID NO 87
<211> LENGTH: 1449
<212> TYPE: DNA
<213> ORGANISM: Artificial sequence
<220> FEATURE:
<223> OTHER INFORMATION: EEE1-B5

<400> SEQUENCE: 87

| | |
|---|---|
| tttcaggcaa ccagagctac atagtgagat cctgtctcaa caaaaataaa ataatctaag | 60 |
| gcttcaaagg gttcaatctc ttaggtagct aaatatgaac aaaagtatta ggatgtgacc | 120 |
| ttttccttag tgacagtcag atagaacctt ctcgagtgca aggacaccaa gtgcaaacag | 180 |
| gctcaagaac agcctggaaa ggtctagtgc tatgggctt caggtcgaat gccaactgtt | 240 |
| ttcaagaact gtgtggattt ttctgcctgt aacgaattca gattcatttt tcaaaactcg | 300 |
| gggagagttt tccccttta taattttttt tttaaattta ttaaactttg tttcgttccc | 360 |
| cttgttttga gaattgcaga gtcatccacc ctgtcacagt gccagggagc tcagggatgg | 420 |
| gcccaggggc ctggcggggc tgaaggggct gggaagcga gggctccaaa gggaccccag | 480 |
| tgtggcagga gccaaagccc taggtcccta gaacgcagag gccaccgccc aggcccagac | 540 |
| gggggtaagcg ggtgggtgtc tggggcgcga agccgcactg cgcatgcgcc gaggtccgct | 600 |
| ccggccgcgc tgatccaagc cgggttctcg cgccgacctg gtcgtgattg acaagtcaca | 660 |
| cacgctgatc cctccgcggg gccgcacagg gtcacagcct tcccctccc cacaaagccc | 720 |
| cctactctct gggcaccaca cacgaacatt ccttgagcgt gaccttgttg gctctagtca | 780 |
| ggcgcctccg gtgcagagac tggaacggcc tggtatggaa gtccctaacc gcatttccgc | 840 |
| ggagggatcg tcggggagcc ggggtttctg aggattatat aaggcgactc cgggcgggtc | 900 |
| ttagctagtt ccgtcggaga cccgagttca gtcgccgctt ctctgtgagg actgctgccg | 960 |
| ccgccgctgg tgaggagaag ccgccgcgct tggcgtagct gagagacgga gggggggcgc | 1020 |
| ggacacgagg ggcagcccgc ggcctggacg ttctgttttcc gtggcccgcg ggaggcacgt | 1080 |
| gaggataggc acggtgcacc cagcggcaag atggcggcca agtggaagcc tgagggggata | 1140 |
| ggcgagcggc cctgaggcgc tcgacggggt tgggggggaa gcaggcccgc gaggcagctg | 1200 |
| cagccgggaa cgtgcggcca acccctttatt tttttttgacg ggttgcgggc cgtaggtgcc | 1260 |
| tccgaagtga gagccgtgtg cgtgtgactg tcgggagagg tcggtcggat tttcatccga | 1320 |
| tagttacaga cggaagtgcg actgaggcgg ggaggaggag agtcggttgg tggcggttga | 1380 |
| acctggacta aggcgcacat gacgtcgcgg tttctatggg ctcataatgg gtggtgaggt | 1440 |
| cattcacct | 1449 |

<210> SEQ ID NO 88
<211> LENGTH: 2617
<212> TYPE: DNA
<213> ORGANISM: Artificial sequence
<220> FEATURE:
<223> OTHER INFORMATION: Transcription regulating sequence

<400> SEQUENCE: 88

| | |
|---|---|
| tttcaggcaa ccagagctac atagtgagat cctgtctcaa caaaaataaa ataatctaag | 60 |

| | |
|---|---|
| gcttcaaagg gttcaatctc ttaggtagct aaatatgaac aaaatttggg aaatgtgacc | 120 |
| ttttccttag tgacagtcag atagaacctt ctcgagtgca aggacaccaa gtgcaaacag | 180 |
| gctcaagaac agcctggaaa ggtctagtgc tatgggcttc aggtcgaat gccaactgtt | 240 |
| ttcaagaact gtgtggattt ttctgcctgt aacgaattca gattcatttt tcaaaactcg | 300 |
| gggagagttt tcccccttta taattttttt tttaaattta ttaaactttg tttcgttccc | 360 |
| cttgttttga gaattgcaga gtcatccacc ctgtcacagt gccagggagc tcagggatgg | 420 |
| gcccaggggc ctggcggggc tgaaggggct ggggaagcga gggctccaaa gggaccccag | 480 |
| tgtggcagga gccaaagccc taggtcccta aacgcagag gccaccggga ccccccagac | 540 |
| ggggtaagcg ggtgggtgtc tggggcgcga agccgcactg cgcatgcgcc gaggtccgct | 600 |
| ccggccgcgc tgatccaagc cgggttctcg cgccgacctg gtcgtgattg acaagtcaca | 660 |
| cacgctgatc cctccgcggg gccgcacagg gtcacagcct ttcccctccc cacaaagccc | 720 |
| cctactctct gggcaccaca cacgaacatt ccttgagcgt gaccttgttg gctctagtca | 780 |
| ggcgcctccg gtgcagagac tggaacggcc ttgggaagta gtccctaacc gcatttccgc | 840 |
| ggagggatcg tcgggagggc gtggcttctg aggattatat aaggcgactc cgggcgggtc | 900 |
| ttagctagtt ccgtcggaga cccgagttca gtcgccgctt ctctgtgagg actgctgccg | 960 |
| ccgccgctgg tgaggagaag ccgccgcgct tggcgtagct gagagacggg gaggggcgc | 1020 |
| ggacacgagg ggcagcccgc ggcctggacg ttctgtttcc gtggcccgcg aggaaggcga | 1080 |
| ctgtcctgag gcggaggacc cagcggcaag atggcggcca agtggaagcc tgagggata | 1140 |
| ggcgagcggc cctgaggcgc tcgacggggt tggggggaa gcaggcccgc gaggcagctg | 1200 |
| cagccgggaa cgtgcggcca acccttatt tttttgacg ggttgcgggc cgtaggtgcc | 1260 |
| tccgaagtga gagccgtggg cgtttgactg tcggagagg tcggtcggat tttcatccgt | 1320 |
| tgctaaagac ggaagtgcga ctgagacggg aaggggggg agtcggttgg tggcggttga | 1380 |
| acctggacta aggcgcacat gacgtcgcgg tttctatggg ctcataatgg gtggtgagga | 1440 |
| catttccctg actatagctt tccctcagtt gtaggacagg gtttgggcct cggcctcggg | 1500 |
| ttaggctctc cagagtgggc aggaaccgga aatccagagg ggggaaaagt gagcctaaat | 1560 |
| tgagttttgt ttcttgtcct atatggttta gagagagact cgctgcaaaa ccgtggctgg | 1620 |
| cctggaactc tagaccagaa ccctggcctt tgccgaccca catgattaga ttcaaggcct | 1680 |
| gtgccaccag cccaggcttt attattatgg tctgggattt ctgcgatttc atccctggtg | 1740 |
| ttttgggatg atgacttgtg ggtcttccct cctccccctt actgtttctg tccatggcgt | 1800 |
| gtgttctaac ccaagtttgt tcttttgggg gggtgggagg gttgcgataa aatgggatct | 1860 |
| atctctgccc tcccaacttg agatctgcct gtcagaagtc tcagtgctga gaataaaggt | 1920 |
| gtgcattggc tcagacctcg atttttttttt tttttattat tttgtaggaa gtctgtagtc | 1980 |
| cttacttgat acataagacc agacaggatc tgatttcctg cctatgaatg gtagatcctc | 2040 |
| tcagtgactg cagtgtgaat ggggaccacg cttttctcca aactatgcag atagccatga | 2100 |
| aagccatgaa atgactttca gccactggta ctgcaatatc cactcaccat ttattatatg | 2160 |
| gaccaggttc accatgccta ggtggctttg cttttgagac acggtttctc tgtgtagcct | 2220 |
| tggttatgtt ttttgttg ttttttaat tatttttggt ttttcgagac agggtttctc | 2280 |
| tgtgtagctt tggagcctat cctggcactt gctccggaga ccaggctggc tccaactca | 2340 |
| gatctgcctg cctctgcctc ccgactgctg ggattaaagt aaagccattc tgcaaccctg | 2400 |

```
ataccactc  aataggtttc  ttatttgaaa  tgtggtttta  tgatttttat  ttctggattt   2460
agaaaagaaa  tcttcagaca  gaagtcttca  gacagaaact  agctgtagtt  tggctgtgtg   2520
aactaaattg  gcatccattt  cacagcaatc  caactgttag  taccatacca  cgaatatttg   2580
tcattcctga  cctgtttttt  gtttgtgtgt  gtgacag                              2617
```

CONSTRUCT AND SEQUENCE FOR ENHANCED GENE EXPRESSION

CROSS REFERENCE TO RELATED APPLICATIONS

This application is a national stage application under 35 U.S.C. § 371 of International Application No. PCT/NL2014/050907, filed on Dec. 24, 2014. This invention relates to and claims the benefit of priority to European Patent Application No. 13199873.4, filed on Dec. 31, 2013, and to European Patent Application No. 13199875.9, also filed on Dec. 31, 2013, the disclosures of each of which are explicitly herein incorporated by reference in their entirety.

FIELD OF THE INVENTION

The invention relates to a method for transcription and expression using a nucleic acid construct which is characterized by the presence of a promoter followed by an intronic promoter. The invention further relates to said nucleic acid construct, an expression vector and a cell comprising said construct, and its use.

The invention also relates to methods for transcription and optionally expression using a nucleotide sequence. The invention further relates to said nucleotide sequence and a construct, expression vector and cell comprising said nucleotide sequence, and its use.

BACKGROUND OF THE INVENTION

There is still a need in the art for alternative and preferably improved methods for regulating the transcription of a transcript and optionally regulating the expression of a protein or polypeptide of interest in host cells.

SUMMARY OF THE INVENTION

The present invention relates to a method for transcription and optionally purifying the produced transcript comprising the steps of:
a) providing a nucleic acid construct comprising a first promoter, a second promoter, and a nucleotide sequence of interest, wherein said first and said second promoters are operably linked to said nucleotide sequence of interest, and wherein said second promoter is flanked by a first intronic sequence located upstream of said promoter and a second intronic sequence located downstream of said promoter; and,
b) contacting a cell with said nucleic acid construct to obtain a transformed cell; and,
c) allowing said transformed cell to produce a transcript of the nucleotide sequence of interest; and optionally,
d) purifying said produced transcript.

The present invention further relates to a method for expressing and optionally purifying a protein or polypeptide of interest comprising the step of:
a) providing a nucleic acid construct comprising a first promoter, a second promoter and a nucleotide sequence encoding a protein or polypeptide of interest, wherein said first and said second promoters are operably linked to said nucleotide sequence encoding a protein or polypeptide of interest, and wherein said second promoter is flanked by a first intronic sequence located upstream of said promoter and a second intronic sequence located downstream of said promoter; and,
b) contacting a cell with said nucleic acid construct to obtain a transformed cell; and,
c) allowing said transformed cell to express the protein or polypeptide of interest; and optionally, purifying said protein or polypeptide of interest.

Preferably, said first intronic sequence comprises at least a donor splice site and said second intronic sequence comprises at least an acceptor splice site. Moreover, the nucleic acid construct of step a) of the method of the invention comprises the following nucleotide sequences indicated here in their relative positions in the 5' to 3' direction: (i) a first promoter (ii) a first intronic sequence comprising at least a donor splice site, (iii) a second promoter, (iv) a second intronic sequence comprising at least an acceptor splice site; and (v) a nucleotide sequence encoding a protein or polypeptide of interest, wherein preferably said first promoter, said first intronic sequence comprising at least a donor splice site, said second promoter, and said second intronic sequence comprising at least an acceptor splice site are all operably linked to said nucleotide sequence encoding a protein or polypeptide of interest.

Preferably, said first promoter has at least 50% identity to nucleotides 1-969 of SEQ ID NO: 1 or nucleotides 1-614 of SEQ ID NO: 2 over its whole length. An overview of all SEQ ID NOs is given in Table 1. Preferably, a nucleotide sequence comprising both said first promoter and said first intronic sequence comprising at least a donor splice site has at least 50% identity to SEQ ID NO: 1 or 2 over its whole length. Preferably, said second promoter has at least 50% sequence identity with SEQ ID NO: 57 or SEQ ID NO: 58 over its whole length.

The present invention further relates to a nucleic acid construct comprising a first promoter and a second promoter, wherein said first and said second promoters are configured to be both operably linked to an optional nucleotide sequence of interest, and wherein said second promoter is flanked by a first intronic sequence located upstream of said promoter and a second intronic sequence located downstream of said promoter. Preferably, said first intronic sequence comprises at least a donor splice site and preferably said second intronic sequence comprises at least an acceptor splice site. Moreover, preferably a nucleic acid construct of the invention comprises the following nucleotide sequences indicated here in their relative positions in the 5' to 3' direction: (i) a first promoter (ii) a first intronic sequence comprising at least a donor splice site, (iii) a second promoter, (iv) a second intronic sequence comprising at least an acceptor splice site; and optionally (v) a nucleotide sequence of interest, wherein preferably said first promoter, said first intronic sequence comprising at least a donor splice site, said second promoter, and said second intronic sequence comprising at least an acceptor splice site are all configured to be operably linked to said optional nucleotide sequence of interest.

Preferably, said first promoter has at least 50% identity to nucleotides 1-969 of SEQ ID NO: 1 or nucleotides 1-614 of SEQ ID NO: 2 over its whole length. Preferably, a nucleotide sequence comprising both said first promoter and said first intronic sequence comprising at least a donor splice site has at least 50% identity to SEQ ID NO: 1 or 2 over its whole length. Preferably, said second promoter has at least 50% sequence identity with SEQ ID NO: 57 or SEQ ID NO: 58 over its whole length.

Preferably, said nucleic acid construct is an isolated construct. Preferably, said nucleic acid construct is a recombinant nucleic acid construct. Preferably, said optional nucleotide sequence of interest is a nucleotide sequence encoding a protein or polypeptide of interest. Preferably, said protein or polypeptide of interest is a heterologous protein or polypeptide.

The present invention further relates to an expression vector comprising a nucleic acid construct or recombinant nucleic acid construct as defined herein.

The present invention further relates to a cell comprising a nucleic acid construct or recombinant nucleic acid construct as defined herein, and/or an expression vector as defined herein.

The present invention also relates to a use of a nucleic acid construct or recombinant nucleic acid construct as defined herein, and/or an expression vector as defined herein and/or a cell as defined herein for the transcription of a nucleotide sequence of interest.

The present invention further relates to a use of a nucleic acid construct or recombinant nucleic acid construct as defined herein, and/or an expression vector as defined herein and/or a cell as defined herein for the expression of a protein or polypeptide of interest.

The present invention further relates to a method for transcription and optionally purifying the produced transcript comprising the step of:
  a) providing a nucleic acid construct comprising an expression enhancing element, a heterologous promoter and a nucleotide sequence of interest of the invention, wherein said expression enhancing element and said heterologous promoter are operably linked to said nucleotide sequence of interest; and,
  b) contacting a cell with said nucleic acid construct to obtain a transformed cell; and,
  c) allowing said transformed cell to produce a transcript of the nucleotide sequence of interest; and optionally,
  d) purifying said produced transcript.

The present invention further relates to a method for expressing and optionally purifying a protein or polypeptide of interest comprising the step of:
  a) providing a nucleic acid construct comprising an expression enhancing element, a heterologous promoter and a nucleotide sequence encoding a protein or polypeptide of interest, wherein said expression enhancing element and said heterologous promoter are operably linked to said nucleotide sequence encoding a protein or polypeptide of interest; and,
  b) contacting a cell with said nucleic acid construct to obtain a transformed cell; and,
  c) allowing said transformed cell to express the protein or polypeptide of interest; and optionally,
  d) purifying said protein or polypeptide of interest.

Preferably, said nucleic acid construct of said method for transcription and/or expression and optionally purifying a transcript and/or protein or polypeptide of interest further comprises an additional expression regulating element operably linked to said nucleotide sequence of interest and/or said nucleotide sequence encoding a protein or polypeptide of interest. Preferably, said additional expression regulating element comprises an intronic sequence. A preferred additional expression regulating element comprises or is an additional expression enhancing element. More preferably, said additional expression regulating element further comprises a translation enhancing element.

The present invention further relates to a nucleic acid molecule that is represented by a nucleotide sequence comprising an expression enhancing element of the invention, i.e. a nucleotide sequence that has at least 50% identity to SEQ ID NO: 1 or 2 over its whole length. An overview of all SEQ ID NOs is given in Table 1. Preferably, said nucleic acid molecule is an isolated nucleic acid molecule. Preferably, said nucleic acid molecule or isolated nucleic acid molecule is represented by a nucleotide sequence that has at least 50% sequence identity to SEQ ID NO: 1 or 2 over its whole length. Preferably, said nucleic acid molecule or isolated nucleic acid molecule is represented by a nucleotide sequence comprising a sequence derived from the *Cricetulus griseus* gene for polyubiquitin of at most 8000 nucleotides.

The present invention further relates to a nucleic acid construct comprising a nucleic acid molecule of the invention. Preferably, said nucleic acid construct is represented by a nucleotide sequence that further comprises a heterologous promoter, wherein preferably said expression enhancing element and said heterologous promoter are configured to be both operably linked to an optional nucleotide sequence of interest. Preferably, said nucleic acid construct further comprises an additional expression regulating element, wherein preferably said expression enhancing element, said heterologous promoter and said additional expression regulating element are configured to be all operably linked to said optional nucleotide sequence of interest. Preferably, said additional expression regulating element further comprises a translation enhancing element. Preferably, said additional expression regulating element comprises an intronic sequence. Preferably, said optional nucleotide sequence of interest is a nucleotide sequence encoding a protein or polypeptide of interest. Preferably, said protein or polypeptide of interest is a heterologous protein or polypeptide.

Preferably, said nucleic acid construct is a recombinant and/or isolated nucleic acid construct.

The present invention further relates to an expression vector comprising a nucleic acid molecule or an isolated nucleic acid molecule as defined herein, and/or a nucleic acid construct or a recombinant and/or isolated nucleic acid construct as defined herein.

The present invention further relates to a cell comprising a nucleic acid molecule or an isolated nucleic acid molecule as defined herein, and/or a nucleic acid construct or recombinant nucleic acid construct as defined herein, and/or an expression vector as defined herein.

The present invention also relates to a use of a nucleic acid molecule or an isolated nucleic acid molecule as defined herein, and/or a nucleic acid construct or a recombinant and/or isolated nucleic acid construct as defined herein, and/or an expression vector as defined herein and/or a cell as defined herein for the transcription of a nucleotide sequence of interest.

The present invention further relates to a use of a nucleic acid molecule or an isolated nucleic acid molecule as defined herein, and/or a nucleic acid construct or a recombinant and/or isolated nucleic acid construct as defined herein, and/or an expression vector as defined herein and/or a cell as defined herein for the expression of a protein or polypeptide of interest.

The present invention further relates to a method for transcription and optionally purifying a produced transcript comprising the step of:
  a) providing a nucleic acid construct comprising a nucleotide sequence that has at least 50% identity to SEQ ID NO:88 over its whole length and which is operably linked to a nucleotide sequence of interest and,
  b) contacting a cell with said nucleic acid construct to obtain a transformed cell; and,
  c) allowing said transformed cell to produce a transcript of the nucleotide sequence of interest; and optionally,
  d) purifying said produced transcript.

The present invention further relates to a method for expressing and optionally purifying a protein or polypeptide of interest comprising the step of:
  a) providing a nucleic acid construct comprising a nucleotide sequence that has at least 50% identity to SEQ ID NO:88 over its whole length and which is operably linked to a nucleotide sequence of interest and contacting a cell with said nucleic acid construct to obtain a transformed cell, and,
  b) allowing said transformed cell to express the protein or polypeptide of interest; and optionally,
  c) purifying said protein or polypeptide of interest.

Preferably, said nucleic acid construct of said method for transcription and/or expression and optionally purifying a transcript and/or protein or polypeptide of interest further comprises an additional expression regulating element operably linked to said nucleotide sequence of interest and/or said nucleotide sequence encoding a protein or polypeptide of interest. Preferably, said additional expression regulating element comprises an intronic sequence. Preferably, said additional expression regulating element further comprises a translation enhancing element.

The present invention further relates to a nucleic acid molecule that is represented by a nucleotide sequence that has at least 50% identity to SEQ ID NO: 88 over its whole length. Preferably, said nucleic acid molecule is an isolated nucleic acid molecule. The present invention further relates to a nucleic acid construct comprising a nucleic acid molecule of the invention. Preferably, said nucleic acid construct is represented by a nucleotide sequence that further comprises an optional nucleotide sequence of interest. Preferably, said nucleic acid construct further comprises an additional expression regulating element, wherein preferably said expression enhancing element is configured to be operably linked to said optional nucleotide sequence of interest. Preferably, said additional expression regulating element further comprises a translation enhancing element. Preferably, said additional expression regulating element comprises an intronic sequence. Preferably, said optional nucleotide sequence of interest is a nucleotide sequence encoding a protein or polypeptide of interest. Preferably, said protein or polypeptide of interest is a heterologous protein or polypeptide.

Preferably, said nucleic acid construct is a recombinant and/or isolated nucleic acid construct.

The present invention further relates to an expression vector comprising a nucleic acid molecule or an isolated nucleic acid molecule as defined herein, and/or a nucleic acid construct or a recombinant and/or isolated nucleic acid construct as defined herein.

The present invention further relates to a cell comprising a nucleic acid molecule or an isolated nucleic acid molecule as defined herein, and/or a nucleic acid construct or recombinant nucleic acid construct as defined herein, and/or an expression vector as defined herein.

The present invention also relates to a use of a nucleic acid molecule or an isolated nucleic acid molecule as defined herein, and/or a nucleic acid construct or a recombinant and/or isolated nucleic acid construct as defined herein, and/or an expression vector as defined herein and/or a cell as defined herein for the transcription of a nucleotide sequence of interest.

The present invention further relates to a use of a nucleic acid molecule or an isolated nucleic acid molecule as defined herein, and/or a nucleic acid construct or a recombinant and/or isolated nucleic acid construct as defined herein, and/or an expression vector as defined herein and/or a cell as defined herein for the expression of a protein or polypeptide of interest.

DESCRIPTION OF THE INVENTION

The inventors identified an expression construct for increasing the expression of a protein or polypeptide of interest. The expression construct of the invention is characterized by two promoters operably linked to a coding sequence of a protein or polypeptide of interest. An expression construct of the invention typically comprises a first promoter followed by a second promoter, a coding sequence of the protein or polypeptide of interest and a polyadenylation sequence, wherein said second promoter is flanked by intronic sequences. Said promoter being flanked by intronic sequences is denominated herein as an intronic promoter. Additional expression regulating sequences may be inserted upstream and downstream of said first and/or second promoter and/or downstream of the polyadenylation sequence. The inventors surprisingly found that an expression construct of the invention comprising a promoter followed by an intronic promoter operably linked to a coding sequence of a protein or polypeptide of interest, results in a significant increase in expression of said protein or polypeptide of interest as compared to an expression construct comprising only one promoter operably linked to said coding sequence. The inventors have found that the expression of initially poorly expressed proteins is increased to appreciable levels when using the combination of a promoter and intronic promoter of the invention instead of a single promoter in an expression construct encoding these proteins, as exemplified in the Examples, more specifically in Example 1. The combination of a promoter and an intronic promoter of the invention in an expression construct for an initially poorly expressed protein facilitates the generation of clonal lines and allows for the generation of clonal lines with increased and relevant expression levels, as exemplified in the Examples, more specifically in Example 3. Furthermore, expression of initially highly expressed proteins is even further increased when using the combination of a promoter and an intronic promoter of the invention instead of a single promoter in an expression construct encoding these proteins as exemplified in the Examples, more specifically in Example 5. Furthermore, an increase in total amount of mRNA and an increase in expression as measured on protein level was found as detailed herein below and exemplified in the Examples enclosed. Furthermore, the percentage of high-producer cell lines in a stably transfected pool is significantly higher as compared to pools with a single promoter operably linked to the coding sequence. As the nucleotide sequence of the invention comprising both a promoter and an intronic promoter operably linked to a nucleotide sequence of interest results in an increase in transcription, the present invention is not limited to the use of this sequence in protein and/or polypeptide expression and/or protein and/or polypeptide production but extends to the use of this combination of a promoter and intronic promoter in methods where higher levels of transcript are desired, for instance in methods for producing noncoding RNA transcripts as further specified herein. Furthermore, a further benefit of the invention is that, apart from an increase in transcription level and/or increase in expression level of the protein or polypeptide of interest, the invention allows for different transcripts to be formed as further detailed herein.

The inventors identified an expression enhancing element for increasing the expression of a protein or polypeptide of interest. The present invention relates to said expression enhancing element. Application of the expression enhancing element of the invention in an expression construct further comprising a heterologous promoter operably linked to a sequence encoding a protein or polypeptide of interest, results in a marked increase in expression of said protein or polypeptide of interest as compared to such expression using a similar expression construct which only differs to the former expression construct in that the expression enhancing element of the invention is absent. The inventors have found that expression of initially poorly expressed proteins is increased to appreciable levels after insertion of the element in an expression construct encoding these proteins as exemplified in the Examples, more specifically in Example 1. Insertion of the expression enhancing element in an expression construct for an initially poorly expressed protein facilitates the generation of clonal lines and allows for the generation of clonal lines with relevant expression levels, as exemplified in the Examples, more specifically in Example 3. Furthermore, expression of initially highly expressed proteins is even further increased after insertion of the element in an expression construct encoding these proteins as exemplified in the Examples, more specifically in Example 5. Furthermore, an increase in total amount of mRNA level and/or an increase in expression as measured on protein level was found as detailed herein below and exemplified in the Examples enclosed. As the expression enhancing element of the invention may result in an increase in transcription, the present invention is not limited to the use of this element in protein and/or polypeptide expression and/or protein and/or polypeptide production but extends to the use of this element in methods where higher levels of transcript are desired, for instance in methods for producing noncoding RNA transcripts as further specified herein.

The inventors further identified a nucleic acid molecule represented by a nucleotide sequence that has at least 50% identity with SEQ ID NO: 88 for increasing the expression of a protein or polypeptide of interest. The use of said nucleotide sequence is attractive as demonstrated in example 11.

First Aspect

In a first aspect, the present invention provides a nucleic acid construct for increasing transcription and/or expression, comprising a first promoter and a second promoter, which are configured to be both operably linked to an optional nucleotide sequence of interest within an expression construct. "Optional" being understood herein as not necessarily being present in an expression construct. For instance, such nucleotide sequence of interest need not be present in a commercialized expression vector, but may be readily introduced by a person skilled in the art before use in a method of the invention.

Preferably, within this first aspect, said nucleotide construct of the invention comprising a first promoter and a second promoter is capable of increasing the transcription of a nucleotide sequence of interest that is under the control of said first promoter and second promoter. Alternatively or in combination with the increased transcription, said nucleotide construct is also preferably capable of increasing expression of a protein or polypeptide of interest encoded by said nucleotide sequence of interest. Preferably, transcription levels are assessed in an expression system using an expression construct comprising said first promoter and second promoter operably linked to a nucleotide sequence of interest using a suitable assay such as RT-qPCR. Preferably, within this first aspect, the nucleotide construct of the invention comprising the first promoter and second promoter of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% of said nucleotide sequence of interest as compared to transcription using a construct which only differs in that the nucleotide sequence of interest is under the control of a single promoter, preferably when tested in a system as exemplified in the Examples which are enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising a first promoter and second promoter sequence to be tested operably linked to said nucleotide sequence of interest. Transcription is preferably measured using RT-qPCR and transcription levels are compared to transcription levels of said nucleotide sequence of interest which are measured under the same conditions except that said first promoter and second promoter are replaced by a single promoter, preferably a CMV promoter represented by SEQ ID NO: 57, in the expression vector used.

Preferably, within this first aspect, expression levels are established in an expression system using an expression construct comprising said first promoter and second promoter operably linked to a nucleotide sequence encoding a protein or polypeptide of interest. Preferably, said protein or polypeptide of interest is a secreted protein or polypeptide and expression of said protein or polypeptide of interest is detected by a suitable assay such as an enzyme-linked immunosorbent assay (ELISA) assay, Western blotting or, dependent on the identity of the protein or polypeptide of interest, any suitable protein identification and/or quantification assay known to the person skilled in the art. Preferably, the first promoter and second promoter of the invention allow for an increase in expression of protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that the encoding sequence of the protein or polypeptide of interest is under the control of a single promoter, preferably when tested in a system as exemplified in the Examples which are enclosed herein. More specifically, the expression of nucleotide sequence of interest encoding for secreted alkaline phosphatase (SeAP) is measured in a mammalian cell system, most preferably in CHO cells, using a pcDNA3.1 expression vector comprising a first promoter and second promoter sequence to be tested operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector only differs in that said first promoter and second promoter are replaced by a single promoter, preferably a CMV promoter represented by SEQ ID NO: 57, in the expression vector used.

Preferably, within said first aspect, said increase of protein or polypeptide expression is copy number independent as established by an assay suitable to determine copy number dependency by a skilled person such as, but not limit to, a triplex Taqman assay as further detailed in Example 4 of the present invention.

Preferably, within said first aspect, said first promoter is located upstream or at the 5' site of said second promoter. Preferably, said second promoter as defined herein should be devoid of sequence elements that will act as transcription terminators. Transcription terminators well known by the persons skilled in the art are sequences that can result in premature termination of transcription such as, but not limited to, stable hairpin structures, repeat sequences such as long terminal repeats (LTRs) or Alu repeats, polyadenylation motifs and transposable elements.

Within the context of the first aspect of the invention a promoter is a promoter capable of initiating transcription in the host cell of choice. Promoters as used herein include tissue-specific, tissue-preferred, cell-type specific, inducible and constitutive promoters as defined herein in the Definitions section. Promoters that may be comprised within said first or second promoter as defined herein are promoters that may be employed in transcription of nucleotide sequences of interest and/or expression of proteins or polypeptides of interest, preferably in mammalian cells, and include, but are not limited to, the human or murine cytomegalovirus (CMV) promoter, a simian virus (SV40) promoter, a human or mouse ubiquitin C (UBC) promoter, a human or mouse or rat elongation factor alpha (EF1-a) promoter, mouse or hamster beta-actin promoter, or a hamster rpS21 promoter. The Tet-Off and Tet-On responsive elements upstream of a minimal promoter such as a CMV promoter is an example of an inducible mammalian promoter. Examples of suitable yeast and fungal promoters are Leu2 promoter, the galactose (Gall or Ga17) promoter, alcohol dehydrogenase I (ADH1) promoter, glucoamylase (Gla) promoter, triose phosphate isomerase (TPI) promoter, translational elongation factor EF-I alpha (TEF2) promoter, glyceraldehyde-3-phosphate dehydrogenase (gpdA) promoter, alcohol oxidase (AOX1) promoter, or glutamate dehydrogenase (gdhA) promoter. An example of a strong ubiquitous promoter for expression in plants is cauliflower mosaic virus (CaMV) 35S promoter.

In an embodiment within said first aspect, said first and said second promoters are similar promoters. Preferably, said first promoter has at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% identity to said second promoter.

In another embodiment within said first aspect, said first promoter and second promoter are distinct or different promoters. Preferably, said first promoter has less than 80%, 75%, 70%, 65%, 60%, 55%, 50%, 45%, 40%, 35%, 30%, 25%, 20%, 15%, 10% or 5% sequence identity to said second promoter.

In a preferred embodiment within said first aspect, said first promoter sequence comprises or consists of a UBC promoter or a CCT8 promoter and said second promoter comprises or consists of a CMV promoter, or the other way around. Preferably, said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-969 of SEQ ID NO: 1 or with nucleotides 1-614 of SEQ ID NO: 2. Preferably, said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 58, or preferably to SEQ ID NO: 57 Preferred within said first aspect is a nucleotide sequence of the invention wherein said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-969 of SEQ ID NO: 1 and said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 57.

Also preferred within said first aspect is a nucleotide sequence of the invention wherein said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity with nucleotides 1-614 of SEQ ID NO: 2 and said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 57.

Also preferred within said first aspect is a nucleotide sequence of the invention wherein said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 58, or preferably to SEQ ID NO: 57 and wherein said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-969 of SEQ ID NO 1 or with nucleotides 1-614 of SEQ ID NO 2.

Preferably within said first aspect a nucleotide sequence of the invention wherein said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity with to SEQ ID NO: 57 and said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity nucleotides 1-969 of SEQ ID NO: 1. Also preferred is a nucleotide sequence of the invention wherein said first promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 57 and said second promoter comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity with nucleotides 1-614 of SEQ ID NO: 2.

It is to be understood that within said first aspect, said first and/or second promoter does not consist only of a promoter enhancer sequence, such as a sequence selected from the group consisting of SEQ ID NO: 52-54. Preferably, said first promoter and second promoter do not consist only of a promoter enhancer sequence, such as a sequence selected from the group consisting of SEQ ID NO: 52-54. Preferably, a nucleotide sequence of the invention does not comprise or consist of SEQ ID NO: 55 or 56.

In a preferred embodiment within said first aspect, said second promoter is flanked by a first intronic sequence at the 5' site or upstream of said second promoter and a second intronic sequence at the 3' site or downstream of said second promoter. Being "flanked" is understood herein as being positioned in between said indicated sequences optionally separated by 1-50, 1-60, 1-70, 1-80, 1-90, 1-100, 1-200, 1-300, 1-400, 1-500, 1-600, 1-700, 1-800, 1-900, 1-1000, 1-5,000 or 1-100,000 nucleotides, these nucleotides being understood to encompass the 5'-UTR. An intronic sequence is understood to be at least part of the nucleotide sequence of an intron. Preferably, said first intronic sequence at the 5' site or upstream of said second promoter comprises at least a donor splice site or splice site GT. A donor splice site is understood herein as a splice site that, when combined with an acceptor splice site as defined herein, results in the formation of an intron as defined in the Definition section. Preferably, a nucleotide sequence is an intron if at least 2%, 5%, 10%, 15%, 20%, 30%, 40%, 50%, 60%, 70%, 80%, 90% or 100% of the primary RNA loses this sequence by RNA splicing using an assay suitable to detect intron splicing, such as but not limited to reverse-transcriptase polymerase chain reaction (RT-PCR) followed by size or sequence analysis of the RT-PCR. Preferred donor splice sites of the invention are M-W-G-[cut]-G-T-R-A-G-K or M-A-R-[cut]-G-T-R-A-G-K in case the host cell is a mammalian cell, A-G-[cut]-G-T-A-W-K in case the host cell is a plant cell, [cut]-G-T-A-W-G-T-T in case the host cell is a yeast cell and R-G-[cut]-G-T-R-A-G, in case the host cell is an insect cell. "[cut]" is to be understood herein as the specific cut site where splicing will take place. Intron splicing can be assessed functionally using an assay as detailed in the Definition section under "intron". Most preferably, the donor splice site comprised within the first intronic sequence of the invention is C-T-G-[cut]-G-T-G-A-G-G or A-A-A-[cut]-G-T-G-A-G-G. Preferably, said first intronic sequence consists of said donor splice site or splice site GT. Preferably, said first intronic sequence comprises a single donor splice site as defined herein. Preferably, said first intronic sequence is free of an acceptor splice site as defined herein below.

Preferably, within said first aspect said second intronic sequence at the 3' site or downstream of said promoter comprises at least an acceptor splice site which is understood herein as the splice site AG preferably preceded by a pyrimidine rich sequence or polypyrimidine tract nucleotide sequence, optionally separated from splice site AG by 1-50 nucleotides, and optionally further comprising a branch site comprising the sequence Y-T-N-A-Y, at the 5' site of the polypyrimidine tract nucleotide sequence, wherein the branch site may have the nucleotide sequence C-Y-G-A-C. An acceptor splice site is understood herein as a splice site that, when combined with a donor splice site encompassed within a construct, results in the formation of an intron as defined in the Definition section. Preferably, the acceptor splice site or splice site AG has the sequence [Y-rich]-N-Y-A-G-[cut]. Preferably, the acceptor splice site or splice site AG has the sequence [Y-rich]-N-Y-A-G-[cut]-R in case the host cell is a mammalian cell, [Y-rich]-D-Y-A-G-[cut]-R or [Y-rich]-D-Y-A-G-[cut]-R-W in case the host cell is a plant cell, [Y-rich]-A-Y-A-G-[cut] in case the host cell is a yeast cell and [Y-rich]-N-Y-A-G-[cut] in case the host cell is an insect cell. "[Y-rich]" is to be understood herein as the polypyrimidine tract which is preferably defined as a consecutive sequence of at least 10 nucleotides comprising at least 6, 7, 8, 9 or preferably 10 pyrimidine nucleotides. Preferably, said acceptor splice site or splice site GT has the sequence Y-A-G-[cut]-R. Preferably, said second intronic sequence comprises a single acceptor splice site. In an embodiment, said second intronic sequence is free of a donor splice site as defined herein. In an alternative embodiment, said second intronic sequence comprises both a donor splice site and an acceptor splice site as defined herein. Most preferably, said second intronic sequence is an intron as defined in the Definition section. Preferably, the second promoter and the intronic sequences flanking the second promoter are configured to form an intronic promoter (referred is to FIG. 1). An intronic promoter is known to a person skilled in the art as a promoter located within an intronic sequence. Preferably, said intronic promoter is an intron as defined in the Definition section. Preferably, the boundaries of the intronic promoter of the present invention are being formed by the donor splice site of the intronic sequence at the 5' site or upstream of the second promoter of the invention and the acceptor splice site of the intronic sequence at the 3' site or downstream of the second promoter of the invention. The intronic promoter of the invention can have a length that is comparable or similar to naturally occurring introns, preferably comparable or similar to naturally occurring introns in the host cell or organism as defined herein. Preferably, said intronic promoter as defined herein is at most 12,000 nucleotides in length. Preferably, said first intronic sequence at the 5' site or upstream of said second promoter is located at the 3' site or downstream of said first promoter. Preferably, the first promoter and second promoter, the intronic sequences flanking the second promoter, and a nucleotide sequence encoding a protein or polypeptide of interest are configured in such a way that the first promoter is upstream of the second promoter, wherein the second promoter is flanked by said intronic sequences to form an intronic promoter, and wherein said first promoter and second promoter are configured to be both upstream and operably linked to the nucleotide sequence encoding a protein or polypeptide of interest (FIG. 1). The intronic promoter may comprise further expression enhancing elements, but preferably the intronic promoter is free of further splice sites apart from the donor and acceptor splice sites as defined herein within the first and second intronic sequences as defined herein. Preferably, one or more expression enhancing sequences are comprised within said first and/or said second promoter. Without being wished to be bound by any theory, transcription starting from either of the two promoters may result in different transcripts (pre-mRNAs) which, upon splicing result in different mRNAs as illustrated in FIG. 1. In support of this theory, the inventors found that different transcripts are formed using a construct of the invention (referred is in this respect to FIG. 1, Example 8 and FIG. 10). Furthermore, the increased activity is found to be severely diminished by 4 nucleotides mutation in the intronic promoter which prevents correct intron splicing (referred in this respect is to FIG. 9 and Example 7), also supporting the theory that both promoters are active in the construct. Therefore, a further benefit of the invention is that, apart from an increase in transcription of the nucleotide sequence of interest and/or an increase in expression level of the protein or polypeptide of interest, the invention allows for different transcripts to be formed. "Different transcripts" are understood herein as transcripts that are structurally different or distinct, i.e. having a different or distinct nucleotide sequence. Therefore a further benefit of the invention is to direct or redirect the splicing of a nucleotide sequence of interest. Depending on the location of the intronic splice sites, the transcripts may have a different or distinct UTR sequence and/or a different or distinct coding sequence. It is also possible that only one type of transcript is formed, e.g. in case the 5'-UTR sequences of said first and second intronic sequences are the same. Assessment whether different transcripts are formed can be done using any suitable method known to the person skilled in the art, such as but not limited to Rapid amplification of cDNA ends Polymerase Chain Reaction (RACE-PCR).

Preferably, within said first aspect, said first intronic sequence at the 5' site or upstream of said second promoter, has at least 80%, 90%, 91%, 92%, 93%, 94%, 95%, 96%, 97%, 98%, 99% or 100% sequence identity with nucleotides 970-1449 of SEQ ID NO: 1 or at least 80%, 90%, 91%, 92%, 93%, 94%, 95%, 96%, 97%, 98%, 99% or 100% sequence identity with nucleotides 667-1228 of SEQ ID NO: 2, preferably comprising at least a donor splice site or splice site GT.

Preferably, within said first aspect, said intronic sequence downstream or at the 3' site of said second promoter comprises a nucleotide sequence having at least 80%, 90%, 91%, 92%, 93%, 94%, 95%, 96%, 97%, 98%, 99% or 100% sequence identity with nucleotides 171-277 of SEQ ID NO: 14, nucleotides 171-274 of SEQ ID NO: 19, nucleotides 133-210 of SEQ ID NO: 20, nucleotides 134-211 of SEQ ID NO: 21, nucleotides 134-226 of SEQ ID NO: 22, nucleotides 134-226 of SEQ ID NO: 23, nucleotides 133-225 of SEQ ID NO: 24, nucleotides 134-226 of SEQ ID NO: 25, nucleotides 146-257 of SEQ ID NO: 26, or nucleotides 147-223 of SEQ ID NO: 27, preferably comprising at least an acceptor splice site AG preceded by a TC-rich nucleotide sequence, optionally separated from splice site AG by 1-50 nucleotides and a branch site comprising the sequence Y-T-N-A-Y or C-Y-G-A-C, at the 5' site of the TC-rich nucleotide sequence.

In a preferred embodiment within said first aspect, said first promoter is flanked at its 3' site by said first intronic sequence. In an embodiment, said first promoter and said first intronic sequence are not aligned in nature but aligned in a construct of the invention by recombination. In another embodiment, said sequence comprising both said first promoter flanked at its 3' site by said first intronic sequence is derived from a naturally occurring sequence. In a preferred embodiment, said nucleotide sequence comprising both a first promoter and a first intronic sequence according to the present invention is a sequence derived from the UBC ubiquitin gene. Preferably, said sequence is derived from a mammalian UBC ubiquitin gene. More preferably, said nucleotide sequence comprising both a first promoter and a first intronic sequence according to the present invention is derived from the *Cricetulus griseus* homologous gene of the human UBC ubiquitin gene, said gene being indicated as the *Cricetulus* sp. gene for polyubiquitin, or CRUPUQ (GenBank D63782). In a preferred embodiment, said nucleotide sequence derived from CRUPUQ is comprising both a first promoter and a first intronic sequence of the invention and is a contiguous sequence of at least 500, 600, 700, 800, 900, 1000 or 1117 in length, preferably at least 1449 nucleotides in length of SEQ ID NO: 1. Preferably, said nucleotide sequence having at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 1 is at most 8000 7000, 6000, 5000, 4000, 3000, 2000, 1900, 1800, 1700, 1600, 1500 or 1449 in length. Most preferably, said sequence being 1449 nucleotides in length. Preferably, said nucleotide sequence is at most 8000, 7000, 6000, 5000, 4000, 3000, 2000, 1900, 1800, 1700, 1600, 1500 or 1449 nucleotides in length and has at least 65% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 70% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 75% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 80% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 85% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 90% identity with SEQ ID NO: 1 over its whole length. Preferably, said nucleotide sequence is at most 8000, 7000, 6000, 5000, 4000, 3000, 2000, 1900, 1800, 1700, 1600, 1500 or 1449 nucleotides in length and has at least 95% identity with SEQ ID NO: 1 over its whole length. Also preferred is a sequence of at most 8000 nucleotides having at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 1.

In a further preferred embodiment within said first aspect, said nucleotide sequence comprising both a first promoter and a first intronic sequence according to the present invention is a sequence derived from a CCT8 gene. Preferably, said sequence is derived from a mammalian CCT8 gene. More preferably, said nucleotide sequence comprising both a first promoter and a first intronic sequence according to the present invention is derived from the human or *Homo sapiens* CCT8 gene. In a preferred embodiment, said nucleotide sequence derived from said CCT8 gene comprising both a first promoter and a first intronic sequence of the invention is a contiguous sequence of at least 500, 600, 700, 791 or 1223 in length, preferably at least 1228 nucleotides in length of SEQ ID NO: 2. Preferably, said nucleotide sequence having at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 2 is at most 8000 nucleotides in length. Preferably, said nucleotide sequence is at most 8000, 7000, 6000, 5000, 4000, 3000, 2000, 1900, 1800, 1700, 1600, 1500 or 1228 in length. Most preferably, said sequence being 1228 nucleotides in length. Preferably, said nucleotide sequence is at most 8000, 7000, 6000, 5000, 4000, 3000, 2000, 1900, 1800, 1700, 1600, 1500 or 1228 nucleotides in length and has at least 65% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 70% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 75% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 80% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 85% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 90% identity with SEQ ID NO: 2 over its whole length. Preferably, said nucleotide sequence is at most 8000, 7000, 6000, 5000, 4000, 3000, 2000, 1900, 1800, 1700, 1600, 1500 or 1228 nucleotides in length and has at least 95% identity with SEQ ID NO: 2 over its whole length. Also preferred is a sequence of at most 8000 nucleotides having at least 65%, 70%, 75%, 80%, 85%, 90%, 91%, 92%, 93%, 94%, 95%, 96%, 97%, 98%, 99% or 100% identity with SEQ ID NO: 2 over its whole length.

Preferably within said first aspect, said nucleotide sequence comprising a first promoter and a first intronic sequence as defined herein has at least 50%, 55%, 60%, 65%, 70%, 75%, 80%, 85%, 90%, 91%, 92%, 93%, 94%, 95%, 96%, 97%, 98%, 99% or 100% identity to any of SEQ ID NO: 1, 2 and 59-61 over its whole length. Preferably, said nucleotide sequence comprising a first promoter and a first intronic sequence as defined herein comprises or consists of any of the sequences selected from the group consisting of SEQ ID NO: 1, 2 and 59-61. Most preferably, said nucleotide sequence comprising a first promoter and a first intronic sequence as defined herein comprises or consists of any of the sequences selected from the group consisting of SEQ ID NO: 1, 2 and 59.

Preferably, the nucleotide construct of the first aspect further comprises one or more additional expression regulating sequences, wherein preferably said first promoter, said intronic sequences as defined herein, and optionally said additional expression regulating sequence are all configured to be operably linked to an optional nucleotide sequence of interest. An "additional expression regulating sequence" is to be understood herein as a sequence or element in addition to the first and/or second promoter and/or the first and/or second intronic sequence as defined herein above, and may be an additional expression enhancing sequence and/or a distinct expression enhancing sequence. An additional expression regulating sequence as encompassed by the present invention can be, but is not limited to, a transcriptional and/or translational regulation of a gene, including but not limited to, 5'-UTR, 3'-UTR, enhancer, promoter, intron, polyadenylation signal and chromatin control elements such as S/MAR (scaffold/matrix attachment region), ubiquitous chromatin opening element, cytosine phosphodiester guanine island and STAR (stabilizing and anti-repressor element), and any derivatives thereof. Other optional regulating sequences that may be present in the nucleic acid construct of the invention include, but are not limited to, coding nucleotide sequences of homologous and/or heterologous nucleotide sequences, including the Iron Responsive Element (IRE), Translational cis-Regulatory Element (TLRE) or uORFs in 5' UTRs and poly(U) stretches in 3' UTRs. Such one or more additional expression regulating, preferably enhancing elements may be located on any position in the construct, preferably directly aligning or comprised within said first and/or second promoter.

A further preferred regulating sequence within said first aspect comprises or consists of a translation enhancing element. Preferably, a translation enhancing element allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that it is free of said translation enhancing element, preferably when tested in a system as exemplified in the Examples which are enclosed herein. More specifically, preferably the expression of nucleotide sequence of interest encoding for secreted alkaline phosphatase (SeAP) is measured in a mammalian cell system, most preferably in CHO cells, using a pcDNA3 0.1 expression vector comprising a translation enhancing element to be tested and a CMV promoter represented by SEQ ID NO: 57, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said translation enhancing element to be tested.

Preferably, within said first aspect said translation enhancing element comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% sequence identity with any of SEQ ID NO: 3-51 over its whole length, or a translation enhancing element that comprises or consists of a nucleotide sequence that comprises:
  i) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides;
  ii) a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said first nucleotide sequence not comprising a GAA repeat nucleotide sequence; or,
  iii) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence.

The GAA repeat nucleotide sequence is defined herein as comprising at least 3 GAA repeats. The GAA repeat nucleotide sequence may comprise an imperfect GAA repeat. The GAA repeat nucleotide sequence may have at least 50% sequence identity, or at least 60% sequence identity, or at least 70% sequence identity, or at least 80% sequence identity, or at least 90% sequence identity or 100% sequence identity with nucleotides 14-50 of SEQ ID NO: 3. The imperfect GAA repeat may comprise the nucleotide sequence $(GAA)_3ATAA(GAA)_8$.

The TC-rich nucleotide sequence is defined herein as having at least 70%, 80%, 90% or 100% sequence identity with nucleotides 54-68 of SEQ ID NO: 3.

The A-rich nucleotide sequence is defined herein as having at least 70%, 80%, 90% or 100% sequence identity with any one of nucleotides 77-87, nucleotides 93-105, nucleotides 111-121, nucleotides 126-132, or nucleotides 152-169 of SEQ ID NO: 3, respectively.

The GT-rich nucleotide sequence is defined herein as having at least 70%, 80%, 90% or 100% sequence identity with nucleotides 133-148 of SEQ ID NO: 3.

Preferably within said first aspect, said translation enhancing sequence comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 19. Preferably, said translation enhancing sequence is located downstream or at the 3' site of the second promoter sequence of the invention and upstream or at the 5' site of an optional nucleotide sequence encoding a protein or polypeptide of interest. Preferably, said translation enhancing sequence is located downstream or at the 3' site of the second promoter sequence of the invention and upstream or at the 5' site of the second intronic sequence as defined herein.

Most preferably within said first aspect, said nucleic acid construct of the first aspect of the invention comprising a first promoter, a first intronic sequence, a second promoter and a second intronic sequence, has at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 73, 74, 75, or 76.

Preferably within said first aspect, the nucleic acid construct of the invention further comprises a nucleotide sequence of interest operably linked to and/or under the control of said first and second promoters and optionally said additional expression regulating sequence as defined herein. It is to be understood that said first promoter and second promoter, and optionally said additional expression regulating sequence are all configured to be operably linked to the same, single nucleotide sequence of interest. In a preferred embodiment, said nucleotide sequence of interest is a nucleotide sequence encoding a protein or polypeptide of interest. The protein or polypeptide of interest can be a homologous protein or polypeptide, but in a preferred embodiment of the invention the protein or polypeptide of interest is a heterologous protein or polypeptide. A nucleotide sequence encoding a heterologous protein or polypeptide may be derived in whole or in part from any source known to the art, including a bacterial or viral genome or episome, eukaryotic nuclear or plasmid DNA, cDNA or chemically synthesized DNA. The nucleotide sequence encoding a protein or polypeptide of interest may constitute an uninterrupted coding region or it may include one or more introns bounded by appropriate splice junctions, it can further be composed of segments derived from different sources, naturally occurring or synthetic. The nucleotide sequence encoding the protein or polypeptide of interest according to the method of the invention is preferably a full-length nucleotide sequence, but can also be a functionally active part or other part of said full-length nucleotide sequence. The nucleotide sequence encoding the protein or polypeptide of interest may also comprise signal sequences directing the protein or polypeptide of interest when expressed to a specific location in the cell or tissue. Furthermore, the nucleotide sequence encoding the protein or polypeptide of interest can also comprise sequences which facilitate protein purification and protein detection by for instance Western blotting and ELISA (e.g. c-myc or polyhistidine sequences).

Within the context of the invention, the protein or polypeptide of interest may have industrial or medicinal (pharmaceutical) applications. Examples of proteins or polypeptides with industrial applications include enzymes such as e.g. lipases (e.g. used in the detergent industry), proteases (used inter alia in the detergent industry, in brewing and the like), cell wall degrading enzymes (such as, cellulases, pectinases, beta.-1,3/4- and beta.-1,6-glucanases, rhamnogalacturonases, mannanases, xylanases, pullulanases, galactanases, esterases and the like, used in fruit processing wine making and the like or in feed), phytases, phospholipases, glycosidases (such as amylases, beta-glucosidases, arabinofuranosidases, rhamnosidases, apiosidases and the like), dairy enzymes (e.g. chymosin). Mammalian, and preferably human, proteins or polypeptides and/or enzymes with therapeutic, cosmetic or diagnostic applications include, but are not limited to, insulin, serum albumin (HSA), lactoferrin, hemoglobin α and ß, tissue plasminogen activator (tPA), erythropoietin (EPO), tumor necrosis factors (TNF), BMP (Bone Morphogenic Protein), growth factors (G-CSF, GM-CSF, M-CSF, PDGF, EGF, and the like), peptide hormones (e.g. calcitonin, somatomedin, somatotropin, growth hormones, follicle stimulating hormone (FSH), interleukins (IL-x), interferons (IFN-γ), phosphatases, antibodies, and antibody-like proteins such as, but not limited to, multispecific antibodies like DART (Dual-Affinity Re-Targeting) and Tribody protein, and antibody fragments like Fc, Fab, Fab2, Fv and scFv. Also included are bacterial and viral antigens, e.g. for use as vaccines, including e.g. heat-labile toxin B-subunit, cholera toxin B-subunit, envelope surface protein Hepatitis B virus, capsid protein Norwalk virus, glycoprotein B Human cytomegalovirus, glycoprotein S, interferon, and transmissible gastroenteritis corona virusreceptors and the like. Further included are genes coding for mutants or analogues of the said proteins.

Within the context of the invention, in an alternative embodiment, said nucleotide sequence of interest is not a coding sequence for a protein or a polypeptide but may be a functional nucleotide sequence such as, but is not limited to, a sequence encoding a non-coding RNA, wherein a non-coding RNA is understood to be an RNA not coding for a protein or polypeptide. Preferably, said non-coding RNA is a reference sequence or regulatory molecule that may regulate the expression of genes or regulating the activity or localization of proteins or polypeptides. For instance, a non-coding RNA may be an antisense RNA or miRNA molecule. As the first promoter and second promoter of the invention is believed to work at the level of transcription, i.e. the increase in expression by the sequence of the invention comprising said first promoter and second promoter as shown herein is believed to result from an increase in transcription, the construct of the invention can also be used for producing increased levels of transcripts, as well as producing transcripts with different sequences. Transcription levels can be quantified by using regular transcription quantification methods known by the person skilled in the art such as, but not limited to, Northern blotting and RT-qPCR.

Second Aspect

In a second aspect, the present invention provides an expression vector comprising a nucleic acid construct according to the first aspect of the invention. The nucleic acid construct according to the invention is preferably a vector, in particular a plasmid, cosmid or phage or nucleotide sequence, linear or circular, of a single or double stranded DNA or RNA, derived from any source, in which a number of nucleotide sequences have been joined or recombined into a unique construction which is capable of introducing any one of the nucleotide sequences of the invention in sense or antisense orientation into a cell. The choice of vector is dependent on the recombinant procedures followed and the host cell used. The vector may be an autonomously replicating vector or may replicate together with the chromosome into which it has been integrated. Preferably, the vector contains a selection marker. Useful markers are dependent on the host cell of choice and are well known to persons skilled in the art and are selected from, but not limited to, the selection markers as defined in third aspect of the invention. A preferred expression vector is the pcDNA3.1 expression vector. Preferred selection markers are the neomycin resistance gene, zeocin resistance gene and blasicidin resistance gene.

Third Aspect

In a third aspect, the present invention provides a cell comprising a nucleic acid construct according to the first aspect of the invention, and/or an expression vector according to the second aspect of the invention as defined herein.

Within the context of the invention, a cell may be a mammalian, including human cell, a plant, animal, insect, fungal, yeast or bacterial cell. A recombinant host cell, such as a mammalian, including human, plant, animal, insect, fungal or bacterial cell, containing one or more copies of a nucleic acid construct according to the invention is an additional subject of the invention. By host cell is meant a cell which contains a nucleic acid construct such as a vector and supports the replication and/or expression of the nucleic acid construct. Examples of suitable bacteria are Gram positive bacteria such as several species of the genera *Bacillus, Streptomyces* and *Staphylococcus* or Gram negative bacteria such as several species of the genera *Escherichia* and *Pseudomonas*. Fungal cells include yeast cells. Expression in yeast can be achieved by using yeast strains such as *Pichia pastoris, Saccharomyces cerevisiae* and *Hansenula polymorpha*. Other fungal cells of interest include filamentous fungi cells as *Aspergillus niger, Trichoderma reesei*, and the like. Furthermore, insect cells such as cells or cell lines from *Drosophila melanogaster, Spodoptera frugiperda*, and *Trichoplusia ni*, such as, but not limited to, S2, Sf9, Sf21, and High Five cells, can be used as host cells. Alternatively, a suitable expression system can be a baculovirus system or expression systems using mammalian cells such as CHO, COS, CPK (porcine kidney), MDCK, BHK, Sp2/0, NS0, and Vero cells. A suitable human cell or human cell line is an astrocyte, adipocyte, chondrocyte, endothelial, epithelial, fibroblast, hair, keratinocyte, melanocyte, osteoblast, skeletal muscle, smooth muscle, stem, synoviocyte cell or cell line. Examples of suitable human cell lines also include HEK 293 (human embryonic kidney), HeLa, Per.C6, CAP (cell lines derived from primary human amniocytes), and Bowes melanoma cells. In an embodiment a human cell is not an embryonic stem cell.

Therefore, another aspect of the invention relates to a host cell that is genetically modified, preferably by a method of the invention, in that a host cell comprises a nucleic acid construct as herein defined above. Host cell is a cell that has been genetically modified. The wording host cell may be replaced by modified cell or transformed cell or recombinant cell or modified host cell or transformed host cell or recombinant host cell. For transformation procedures in plants, suitable bacteria include *Agrobacterium tumefaciens* and *Agrobacterium rhizogenes*.

A nucleic acid construct preferably is stably maintained, either as an autonomously replicating element, or, more preferably, the nucleic acid construct is integrated into the host cell's genome, in which case the construct is usually integrated at random positions in the host cell's genome, for instance by non-homologous recombination. Stably transformed host cells are produced by known methods. The term stable transformation refers to exposing cells to methods to transfer and incorporate foreign DNA into their genome. These methods include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

Alternatively, a protein or polypeptide of interest may be expressed in a host cell, e.g., a mammalian cell, relying on transient expression from vectors.

A nucleic acid construct according to the invention preferably also comprises a marker gene which can provide selection or screening capability in a treated host cell. Selectable markers are generally preferred for host transformation events, but are not available for all host cells. A nucleic acid construct disclosed herein can also include a nucleotide sequence encoding a marker product. A marker product can be used to determine if the construct or portion thereof has been delivered to the cell and once delivered is being expressed. Examples of marker genes include, but are not limited to the *E. coli* lacZ gene, which encodes β-galactosidase, and a gene encoding the green fluorescent protein.

Within the context of the invention, examples of suitable selectable markers for mammalian cells include, but are not limited to dihydrofolate reductase (DHFR), glutathione synthetase (GS), thymidine kinase, neomycin, neomycin analog G418, hygromycin, blasticidin, zeocin and puromycin.

Other suitable selectable markers include, but are not limited to, antibiotic, metabolic, auxotrophic or herbicide resistant genes which, when inserted in a host cell in culture, would confer on those cells the ability to withstand exposure to an antibiotic. Metabolic or auxotrophic marker genes enable transformed cells to synthesize an essential component, usually an amino acid, which allows the cells to grow on media that lack this component. Another type of marker gene is one that can be screened by histochemical or biochemical assay, even though the gene cannot be selected for. A suitable marker gene found useful in such host cell transformation experience is a luciferase gene. Luciferase catalyzes the oxidation of luciferin, resulting in the production of oxyluciferin and light. Thus, the use of a luciferase gene provides a convenient assay for the detection of the expression of introduced DNA in host cells by histochemical analysis of the cells. In an example of a transformation process, a nucleotide sequence sought to be expressed in a host cell could be coupled in tandem with the luciferase gene. The tandem construct could be transformed into host cells, and the resulting host cells could be analyzed for expression of the luciferase enzyme. An advantage of this marker is the non-destructive procedure of application of the substrate and the subsequent detection.

When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. Two non-limiting examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin. Other useful markers are dependent on the host cell of choice and are well known to persons skilled in the art.

When a transformed host cell is obtained with a method according to the invention (see below), a host tissue may be regenerated from said transformed cell in a suitable medium, which optionally may contain antibiotics or biocides known in the art for the selection of transformed cells.

Resulting transformed host tissues are preferably identified by means of selection using a selection marker gene as present on a nucleic acid construct as defined herein.

Fourth Aspect

In a fourth aspect, the present invention provides a method for expressing and optionally purifying a protein or polypeptide of interest comprising the step of:
 a) providing a nucleic acid construct according to the first aspect of the invention comprising a nucleotide sequence encoding a protein or polypeptide of interest; and,
 b) contacting a cell with said nucleic acid construct to obtain a transformed cell; and,
 c) allowing said transformed cell to express the protein or polypeptide of interest; and optionally,
 d) purifying said protein or polypeptide of interest.

The method of the invention may be an in vitro or ex vivo method. The method of the invention may be applied on a cell culture, organism culture, or tissue culture. Alternatively, next to the expression in host cells, the protein or polypeptide of interest can be produced in cell-free translation systems using RNAs derived from the nucleic acid constructs of the present invention. The method of the invention may be performed on cultured cells.

The skilled person is capable of transforming cells in accordance with step b). Transformation methods as used in step b) include, but are not limited to transfer of purified DNA via cationic lipid reagents and plyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to express the protein or polypeptide of interest, and optionally said protein or polypeptide is subsequently recovered. For example, the transformed cell may be subjected to conditions leading to expression of the protein or polypeptide of interest. The person skilled in the art is well aware of techniques to be used for expressing or overexpressing the protein or polypeptide of interest. Methods in which the transformed cell does not need to be subjected to specific conditions leading to expression of the protein or polypeptide of interest, but in which the protein or polypeptide of interest is automatically (e.g., constitutively) expressed, are also included in the method of the present invention.

Within the context of the invention, purification steps depend on the expressed protein or polypeptide and the host cell used but can comprise isolation of the protein or polypeptide. When applied to a protein/polypeptide, the term "isolation" indicates that the protein or polypeptide is found in a condition other than its native environment. In a preferred form, the isolated protein or polypeptide is substantially free of other proteins, particularly other homologous proteins. It is preferred to provide the protein or polypeptide in a greater than 40% pure form, more preferably greater than 60% pure form. Even more preferably it is preferred to provide the protein or polypeptide in a highly purified form, i.e., greater than 80% pure, more preferably greater than 95% pure, and even more preferably greater than 99% pure, as determined by SDS-PAGE. If desired, the nucleotide sequence encoding a protein or polypeptide of interest may be ligated to a heterologous nucleotide sequence to encode a fusion protein or polypeptide to facilitate protein purification and protein detection on for instance Western blot and in an ELISA. Suitable heterologous sequences include, but are not limited to, the nucleotide sequences coding for proteins such as for instance glutathione-S-transferase, maltose binding protein, metal-binding polyhistidine, green fluorescent protein, luciferase and beta-galactosidase. The protein or polypeptide may also be coupled to non-peptide carriers, tags or labels that facilitate tracing of the protein or polypeptide, both in vivo and in vitro, and allow for the identification and quantification of binding of the protein or polypeptide to substrates. Such labels, tags or carriers are well-known in the art and include, but are not limited to, biotin, radioactive labels and fluorescent labels.

Preferably, the method of this fourth aspect of the invention allows for an increase in expression of a protein or polypeptide of interest. Preferably, expression levels are established in an expression system using an expression construct according to the first aspect of the invention comprising a first and a second promoter according to the first aspect of the invention, operably linked to a nucleotide sequence encoding a protein or polypeptide of interest. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, the method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) that it is free of said first promoter and said second promoter and is operably linked to a single promoter, preferably when tested in a system as exemplified in the Examples which are enclosed herein. More specifically, the expression of nucleotide sequence of interest encoding for secreted alkaline phosphatase (SeAP) is measured in a mammalian cell system, most preferably in CHO cells, using a pcDNA3.1 expression vector comprising a first promoter and second promoter sequence to be tested operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that said first promoter and second promoter are replaced by a single promoter, preferably a CMV promoter represented by SEQ ID NO: 57, in the expression vector used.

Fifth Aspect

In a fifth aspect, the present invention provides a method for expressing a protein or polypeptide of interest in an organism, comprising the steps of:
 a) providing a nucleic acid construct according to the first aspect of the invention comprising a nucleotide sequence encoding a protein or polypeptide of interest; and, b) contacting a target cell and/or target tissue of an organism, with said nucleic acid construct to obtain a transformed target cell and/or transformed target tissue, allowing said transformed cell to express the protein or polypeptide of interest; and optionally, c) allowing said transformed target cell and/or target tissue to develop into a transformed organism; and, optionally, d) allowing said transformed organism to express the protein or polypeptide of interest, for example, subjecting said transformed organism to conditions leading to expression of the protein or polypeptide of interest, and optionally recovering said protein or polypeptide.

Within the context of the invention, the target cell may be an embryonal target cell, e.g., embryonic stem cell, for example, derived from a non-human mammalian, such as bovine, porcine, etcetera species. Preferably, said target cell is not a human embryonic stem cell. In the case of a multicellular fungus, such target cell may be a fungal cell that can be proliferated into said multicellular fungus. When a transformed plant tissue or plant cell (e.g., pieces of leaf, stem segments, roots, but also protoplasts or plant cells cultivated by suspension) is obtained with the method according to the invention, whole plants can be regenerated from said transformed tissue or cell in a suitable medium, which optionally may contain antibiotics or biocides known in the art for the selection of transformed cells. The method of the invention may be applied in nucleic acid based vaccination and/or gene therapy preferably in a mammal, most preferably in a human. Encompassed within the present invention is a method of treatment comprising the method of the present aspect, wherein the protein or polypeptide of interest is a therapeutic and/or immunogenic protein or polypeptide. The invention also relates to a construct of the first aspect of the invention for treatment, wherein the protein or polypeptide of interest is a therapeutic and/or immunogenic protein or polypeptide. Furthermore, the invention relates to the use of a construct of the first aspect of the invention for the manufacture of a medicament, wherein the protein or polypeptide of interest is a therapeutic and/or immunogenic protein or polypeptide.

Furthermore, a part of the invention is a non-human transformed organism. Said organism is transformed with a nucleotide sequence, recombinant nucleic acid construct, or vector according to the present invention, and is capable of producing the polypeptide of interest. This includes a non-human transgenic organism, such as a transgenic non-human mammalian, transgenic plant (including propagation, harvest and tissue material of said transgenic plant, including, but not limited to, leafs, roots, shoots and flowers), multicellular fungus, and the like.

Preferably, the method of this fifth aspect of the invention allows for an increase in expression of a protein or polypeptide of interest in said organism or at least in one tissue or organelle or organ of said organism. Preferably, expression levels are established in an expression system using an expression construct according to the first aspect of the invention comprising a first and a second promoter according to the first aspect of the invention, operably linked to a nucleotide sequence encoding a protein or polypeptide of interest. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, the method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% in said organism or at least in one tissue or organelle or organ of said organism as compared to a method which only differs in that a construct is used in step a) that it is free of said first promoter and said second promoter and is operably linked to a single promoter, preferably when tested in a system as exemplified in the Examples which are enclosed herein. More specifically, the expression of nucleotide sequence of interest encoding for secreted alkaline phosphatase (SeAP) is measured in a mammalian cell system, most preferably in CHO cells, using a pcDNA3.1 expression vector comprising a first promoter and second promoter sequence to be tested operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that said first promoter and second promoter are replaced by a single promoter, preferably a CMV promoter represented by SEQ ID NO: 57, in the expression vector used. Preferably, said increase of protein or polypeptide expression is copy number independent as established by an assay suitable to determine copy number dependency by a skilled person such as, but not limit to, a triplex Taqman assay as further detailed in Example 4 of the present invention.

Sixth Aspect

In a sixth aspect, the present invention provides a method for transcription and optionally purifying the produced transcript comprising the step of:

a) providing a nucleic acid construct according to the first aspect of the invention comprising a nucleotide sequence of interest; and, b) contacting a cell with said nucleic acid construct to obtain a transformed cell; and, c) allowing said transformed cell to produce a transcript of the nucleotide sequence of interest; and optionally, d) purifying said produced transcript.

In a preferred embodiment of the method according to the invention a nucleic acid construct as defined above is used. The method of the invention may be an in vitro or ex vivo method. The method of the invention may be applied on a cell culture, organism culture, or tissue culture. The method of the invention may be applied in nucleic acid based vaccination and/or gene therapy preferably in a mammal, preferably in a human. Encompassed within the present invention is a method for treatment comprising or consisting of the method of the present aspect, wherein the nucleotide sequence of interest encodes for a therapeutic transcript. The invention also relates to a construct of the first aspect of the invention for use in treatment, wherein the nucleotide sequence of interest encodes for a therapeutic transcript. Furthermore, the invention relates to the use of a construct of the first aspect of the invention for the manufacture of a medicament, wherein the nucleotide sequence of interest encodes for a therapeutic transcript.

The skilled person is capable of transforming cells in accordance with step b). Transformation methods as used in step b) include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to produce a transcript of the nucleotide sequence of interest, and optionally the produced transcript is subsequently recovered. For example, the transformed cell may be subjected to conditions leading to transcription the nucleotide sequence of interest. The person skilled in the art is well aware of techniques to be used for transcription the nucleotide sequence of interest. Methods in which the transformed cell does not need to be subjected to specific conditions leading to transcription of the nucleotide sequence of interest, but in which the nucleotide sequence of interest is automatically (e.g., constitutively) transcribed, are also included in the method of the present invention.

Purification steps depend on the transcript produced. The term "isolation" indicates that the transcript is found in a condition other than its native environment. In a preferred form, the isolated transcript is substantially free of other cellular components, particularly other homologous cellular components such as homologous proteins. It is preferred to provide the transcript in a greater than 40% pure form, more preferably greater than 60% pure form. Even more preferably it is preferred to provide the transcript in a highly purified form, i.e., greater than 80% pure, more preferably greater than 95% pure, and even more preferably greater than 99% pure, as determined by Northern blotting.

Preferably, the method of this aspect of the invention allows for an increase in transcription of a nucleotide sequence of interest. Preferably, transcription levels are established in an expression system using an expression construct according to the first aspect of the invention comprising a first and a second promoter according to the first aspect of the invention operably linked to a nucleotide sequence of interest. Preferably, transcription of said nucleotide sequence of interest is detected by a suitable assay such as RT-qPCR. Preferably, the method of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) that it is free of said first promoter and second promoter and is operably linked to a single promoter, preferably when tested in a system as exemplified in the Examples which are enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising a first promoter and second promoter sequence to be tested operably linked to said nucleotide sequence of interest. Transcription is preferably measured using RT-qPCR and transcription levels are compared to transcription levels of said nucleotide sequence of interest which are measured under the same conditions except that said first promoter and second promoter are replaced by a single promoter, preferably a CMV promoter represented by SEQ ID NO: 57, in the expression vector used.

Seventh Aspect

In a seventh aspect, the present invention provides a method for splicing or redirecting the splicing of a nucleotide sequence of interest, and optionally purifying the produced transcripts comprising the step of:
a) providing a nucleic acid construct according to the first aspect of the invention comprising a nucleotide sequence of interest; and,
b) contacting a cell with said nucleic acid construct to obtain a transformed cell; and,
c) allowing said transformed cell to produce transcripts of the nucleotide sequence of interest resulting in the production of a transcript; and optionally,
d) purifying said produced transcripts.

Preferably within this aspect, said nucleic acid construct used in step a) comprises a nucleotide sequence upstream or at the 5' site of the second intronic sequence of the invention that is different or distinct from the nucleotide sequence upstream or at the 5' site of the first intronic sequence of the invention. Preferably, the nucleotide sequence between first promoter and 5' of said first intronic sequence and the nucleotide sequence between second promoter and 5' of said second intronic sequence differs at least 5%, 10%, 20%, 30%, 40%, 50%, 60%, 70%, 80%, 90% or 100% in nucleotide sequence. Preferably, a method of this aspect of the invention wherein such a nucleic acid construct is used results in the production of two different or distinct transcripts, which differ in nucleotide sequence at the 5' site of the transcripts. In case the nucleotide sequence of interest is located downstream or at the 3' site of the second intronic sequence, the resulting transcripts will differ in sequence upstream of said nucleotide sequence of interest as can be detected by any suitable assay known by the person skilled in the art, such as, but not limited to 5'RACE-PCR.

In a preferred embodiment within this aspect, the nucleotide sequence of interest is a sequence encoding a protein or polypeptide of interest. The method of this aspect can be used to produce two proteins or polypeptides with different or distinct N-termini using the construct of the invention. Preferably, a first protein or polypeptide comprising a first N-terminus and a second protein or polypeptide comprising a second N-terminus are produced using the method of this aspect, wherein preferably, a first nucleotide sequence encoding said first N-terminus is located directly upstream or at the 5' site of said first intronic sequence and a second nucleotide sequence encoding said second N-terminus is located directly upstream or at the 5' site of said second intronic sequence. Preferably said first nucleotide sequence encoding said first N-terminus is located downstream or at the 3' site of said first promoter and upstream or at the 5' site of said first intronic sequence. Preferably said second nucleotide sequence encoding said second N-terminus is located downstream or at the 3' site of said second promoter and upstream or at the 5' site of said second intronic sequence. Preferably, said nucleic acid construct further comprises a nucleotide sequence encoding a C-terminus located downstream or at the 3' site of said second intronic sequence. In this embodiment, it is required that said second intronic sequence is an intron as defined in the Definition section. The difference between the N termini may be limited to a signal sequence and result in identical expressed proteins or polypeptides, wherein the localization of the proteins or polypeptides may differ. If performed in an expression system as earlier defined herein, the method of this embodiment preferably results in the production of two proteins or polypeptides of interest, wherein said first protein or polypeptide will comprise said first N-terminus linked to said C-terminus and said second protein or polypeptide will comprise said second N-terminus linked to said C-terminus, as can be detected by any suitable assay known by the person skilled in the art, such as, but not limited to, ELISA assay, Western blotting or, dependent on the identity of the protein or polypeptide of interest, any suitable protein identification and/or quantification assay known to the person skilled in the art. Preferably, said assay used to detect the two different or distinct proteins or polypeptides produced is specifically adapted to distinguish between the different proteins or polypeptides produced, for instance using a detecting antibody specifically binding to either the first or the second N-terminus of proteins or polypeptides produced.

Eight Aspect

In an eighth aspect, the present invention provides a use of a nucleic acid construct according to the first aspect of the invention, and/or a use of an expression vector according to the second aspect of the invention, and/or a use of a cell according to the third aspect of the invention, for the expression of a protein or polypeptide of interest.

Ninth Aspect

In a ninth aspect, the present invention provides for a nucleic acid construct according to the first aspect of the invention, and/or an expression vector according to the second aspect of the invention, and/or a cell according to the third aspect of the invention for use as a medicament. The invention also relates to a method of treatment comprising the administration of a nucleic acid construct according to the first aspect of the invention, and/or an expression vector according to the second aspect of the invention, and/or a cell according to the third aspect of the invention, wherein preferably said administration is to a mammal, more preferably to a human. Preferably, said treatment is nucleic acid based vaccination and/or gene therapy preferably in a mammal, most preferably in a human. Furthermore, the invention relates to the use of a nucleic acid construct according to the third aspect of the invention, and/or the use of an expression vector according to the second aspect of the invention, and/or the use of a cell according to the third aspect of the invention, for the preparation of a medicament. Preferably said medicament is for nucleic acid based vaccination and/or gene therapy preferably in a mammal, most preferably in a human.

Tenth Aspect

In a tenth aspect, the present invention provides a nucleic acid molecule that is represented by a nucleotide sequence that comprises or consists of an expression enhancing element for increasing transcription of a nucleotide sequence of interest and/or expression of a protein or polypeptide of interest. Preferably, the expression enhancing element of the invention is capable of increasing the transcription of a nucleotide sequence of interest and/or expression of a protein or polypeptide of interest. Preferably in this aspect, the expression enhancing element of the invention capable of increasing the transcription of a nucleotide sequence of interest and/or expression of a protein or polypeptide of interest is located upstream or at the 5' site of a promoter that is operably linked to said nucleotide sequence of interest.

Preferably within this aspect, transcription levels are established in an expression system using an expression construct comprising said expression enhancing element operably linked to a nucleotide sequence of interest using a suitable assay such a RT-qPCR. Preferably, the expression enhancing element of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% as compared to transcription levels using a construct which only differs in that it is free of said expression enhancing element, preferably as exemplified in the Examples which are enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising an expression enhancing element to be tested and a CMV promoter represented by SEQ ID NO: 57, operably linked to said nucleotide sequence of interest. Transcription is preferably measured using RT-qPCR and transcription levels are compared to transcription levels of said nucleotide sequence of interest measured under the same conditions except that the expression vector used is free of said expression enhancing element to be tested.

Preferably within this aspect, expression levels are established in an expression system using an expression construct comprising said expression enhancing element operably linked to a nucleotide sequence encoding a protein or polypeptide of interest. Preferably, said protein or polypeptide of interest is a secreted protein or polypeptide and expression of said protein or polypeptide of interest is detected by a suitable assay such as an enzyme-linked immunosorbent assay (ELISA) assay, Western blotting or, dependent on the identity of the protein or polypeptide of interest, any suitable protein identification and/or quantification assay known to the person skilled in the art. Preferably, the expression enhancing element of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that it is free of said expression enhancing element, preferably when tested in a system as exemplified in the Examples which are enclosed herein. More specifically, preferably the expression of a nucleotide sequence of interest encoding for secreted alkaline phosphatase (SeAP) is measured in a mammalian cell system, most preferably in CHO cells, using a pcDNA3.1 expression vector comprising an expression enhancing element to be tested and a CMV promoter represented by SEQ ID NO: 57, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said expression enhancing element to be tested.

Preferably within this aspect, said nucleic acid molecule is an isolated nucleic acid molecule as defined herein. In a preferred embodiment, said expression enhancing element is a sequence that is derived from the UBC ubiquitin gene. Preferably, said expression enhancing element is derived from a mammalian UBC ubiquitin gene. More preferably, said expression enhancing element is derived from the *Cricetulus griseus* homologous gene of the human UBC ubiquitin gene, said gene being indicated as the *Cricetulus* sp. gene for polyubiquitin, or CRUPUQ (GenBank D63782).

In a preferred embodiment, said expression enhancing element derived from CRUPUQ comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-969 of SEQ ID NO: 1. Preferably, said sequence having at least 50%, 55%, 60%, 65%, 70%, 75%, 80%, 85%, 90%, 91%, 92%, 93%, 94%, 95%, 96%, 97%, 98%, 99% or 100% identity to nucleotides 1-969 of SEQ ID NO: 1 is a promoter as defined in the Definition section. Preferably, said promoter is capable of initiating transcription of a nucleotide sequence of interest and/or expression of a polypeptide or protein or polypeptide of interest encoded by a nucleotide sequence in a host cell as defined herein below. In a further preferred embodiment, said expression enhancing element derived from CRUPUQ comprises or consists of an intronic sequence. An intronic sequence is understood to be at least part of the nucleotide sequence of an intron. Preferably, said intronic sequence comprises at least a donor splice site or splice site GT. A donor splice site is understood herein as a splice site that, when combined with an acceptor splice site as defined herein, results in the formation of an intron as defined in the Definition section. Preferably, a nucleotide sequence is an intron if at least 2%, 5%, 10%, 15%, 20%, 30%, 40%, 50%, 60%, 70%, 80%, 90% or 100% of the primary RNA loses this sequence by RNA splicing using an assay suitable to detect intron splicing, such as but not limited to reverse-transcriptase polymerase chain reaction (RT-PCR) followed by size or sequence analysis of the RT-PCR. Preferred donor splice sites of the invention are M-W-G-[cut]-G-T-R-A-G-K in case the host cell is a mammalian cell, A-G-[cut]-G-T-A-W-K in case the host cell is a plant cell, [cut]-G-T-A-W-G-T-T in case the host cell is a yeast cell and R-G-[cut]-G-T-R-A-G, in case the host cell is an insect cell. "[cut]" is to be understood herein as the specific cut site where splicing will take place. Intron splicing can be assessed functionally using an assay as detailed in the Definition section under "intron". Most preferably, the donor splice site comprised within the expression enhancing element of the invention is C-T-G-[cut]-G-T-G-A-G-G. Preferably, said intronic sequence encompassed within said expression enhancing element consists of said donor splice site or splice site GT. Preferably, said intronic sequence encompassed within said expression enhancing element is free of an acceptor splice site as defined herein below. Preferably, said expression enhancing element comprising an intronic sequence has at least 50%, 55%, 60%, 65%, 70%, 75%, 80%, 85%, 90%, 91%, 92%, 93%, 94%, 95%, 96%, 97%, 98%, 99% or 100% identity to nucleotides 970-1449 of SEQ ID NO: 1. In a preferred embodiment, said expression enhancing element comprises or consists of a promoter and an intronic sequence as defined herein. Preferably, the expression enhancing element of the invention has at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 1 over its whole length. Preferably, said expression enhancing element of the invention that has at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 1 over its whole length comprises both a promoter and an intronic sequence as defined herein. Preferably, said expression enhancing element for increasing expression is a contiguous sequence of at least 500, 600, 700, 800, 900, 1000, 1100 or 1117 in length, preferably at least 1449 nucleotides in length of SEQ ID NO: 1. Preferably, said expression enhancing element having at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 1 is at most 8000 nucleotides in length. Preferably, said expression enhancing element is at most 8000, 7000, 6000, 5000, 4000, 3000, 2000, 1900, 1800, 1700, 1600, 1500 or 1449 in length. Most preferably, said sequence being 1449 nucleotides in length. Preferably, said expression enhancing element is at most 8000, 7000, 6000, 5000, 4000, 3000, 2000, 1900, 1800, 1700, 1600, 1500 or 1449 nucleotides in length and has at least 65% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 70% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 75% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 80% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 85% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 90% identity to SEQ ID NO: 1 over its whole length. Preferably, said expression enhancing element is at most 8000, 7000, 6000, 5000, 4000, 3000, 2000, 1900, 1800, 1700, 1600, 1500 or 1449 nucleotides in length and has at least 95% identity to SEQ ID NO: 1 over its whole length. Preferably, said expression enhancing element comprises or consists of a sequence that is represented by SEQ ID NO: 1.

In a further preferred embodiment within this aspect, said expression enhancing element of the invention is a sequence derived from the CCT8 gene. Preferably, said element is derived from a mammalian CCT8 gene. More preferably, said expression enhancing element is derived from the human or *Homo sapiens* CCT8 gene.

In a preferred embodiment within said aspect, said expression enhancing element derived from the *Homo sapiens* CCT8 gene comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-614 of SEQ ID NO: 2. Preferably, said sequence that has at least 50%, 55%, 60%, 65%, 70%, 75%, 80%, 85%, 90%, 91%, 92%, 93%, 94%, 95%, 96%, 97%, 98%, 99% or 100% identity to nucleotides 1-614 of SEQ ID NO: 2 is a promoter as defined in the Definition section. In a further preferred embodiment, said expression enhancing element derived from the *Homo sapiens* CCT8 gene comprises or consists of an intronic sequence. Preferably, said intronic sequence is an intronic sequence as earlier defined herein comprising at least a donor splice site or splice site GT as earlier defined herein. Preferably said donor splice site has the sequence M-A-R-[cut]-G-T-R-A-G-K, most preferably A-A-A-[cut]-G-T-G-A-G-G. Preferably, said intronic sequence encompassed within said expression enhancing element consists of said donor splice site or splice site GT. Preferably, said expression enhancing element comprising an intronic sequence has at least 50%, 55%, 60%, 65%, 70%, 75%, 80%, 85%, 90%, 91%, 92%, 93%, 94%, 95%, 96%, 97%, 98%, 99% or 100% identity to nucleotides 667-1228 of SEQ ID NO: 2.

In a preferred embodiment within said aspect, said expression enhancing element comprises or consists of a promoter and an intronic sequence as defined herein. Preferably, the expression enhancing element of the invention has at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 2 over its whole length. Preferably, said expression enhancing element of the invention that has at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 2 over its whole length comprises both a promoter and an intronic sequence as defined herein. Preferably, said expression enhancing element for increasing expression is a contiguous sequence of at least 500, 600, 700, 791 or 1223 in length, preferably at least 1228 nucleotides in length of SEQ ID NO: 2. Preferably, said expression enhancing element having at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 2 is at most 8000 nucleotides in length. Preferably, said expression enhancing element is at most 8000, 7000, 6000, 5000, 4000, 3000, 2000, 1900, 1800, 1700, 1600, 1500 or 1228 in length. Most preferably, said sequence being 1228 nucleotides in length. Preferably, said expression enhancing element is at most 8000, 7000, 6000, 5000, 4000, 3000, 2000, 1900, 1800, 1700, 1600, 1500 or 1228 nucleotides in length and has at least 65% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 70% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 75% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 80% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 85% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 90% identity to SEQ ID NO: 2 over its whole length. Preferably, said expression enhancing element is at most 8000, 7000, 6000, 5000, 4000, 3000, 2000, 1900, 1800, 1700, 1600, 1500 or 1228 nucleotides in length and has at least 95% identity to SEQ ID NO: 2 over its whole length. Preferably, said expression enhancing element comprises or consists of a sequence that is represented by SEQ ID NO: 2.

Further preferred is a nucleotide sequence comprising an expression enhancing element as defined herein that has at least 50%, 55%, 60%, 65%, 70%, 75%, 80%, 85%, 90%, 91%, 92%, 93%, 94%, 95%, 96%, 97%, 98%, 99% or 100% identity to any of SEQ ID NO: 59-61 over its whole length. Preferably, said expression enhancing element comprises or consists of any of the sequences selected from the group consisting of SEQ ID NO: 59-61. Most preferably, said expression enhancing element comprises or consists of a sequence that is represented by SEQ ID NO: 59.

Eleventh Aspect

In an eleventh aspect, the present invention provides a nucleic acid construct comprising a nucleic acid molecule according to the tenth aspect of the invention. A nucleic acid construct of the invention comprises an expression enhancing element according to the tenth aspect of the present invention. Preferably, said nucleic acid construct is a recombinant and/or isolated construct as defined herein. Preferably, said nucleic acid construct further comprises a heterologous promoter, wherein preferably said expression enhancing element and said heterologous promoter are configured to be both operably linked to an optional nucleotide sequence of interest as defined herein below. "Heterologous promoter" is to be understood herein as a promoter that is not naturally operably linked to the expression enhancing element of the invention, i.e. a contiguous sequence comprising said expression enhancing element and said heterologous promoter does not occur in nature as neighboring sequences but can be synthesized as a recombinant sequence.

Preferably within this aspect, said heterologous promoter is located within a nucleic acid construct of the invention downstream or at the 3' site of the expression enhancing element of the invention. Preferably, said heterologous promoter is located within a construct of the invention upstream or at the 5' site of the nucleotide sequence of the invention encoding a protein or polypeptide of interest. In an embodiment of the invention the heterologous promoter is a promoter capable of initiating transcription in the host cell of choice. Heterologous promoters as used herein include tissue-specific, tissue-preferred, cell-type specific, inducible and constitutive promoters as defined herein. Heterologous promoters and/or regulating sequences that may be employed in expression of polypeptides according to the present invention, preferably in mammalian cells, include, but are not limited to, the human or murine cytomegalovirus (CMV) promoter, a simian virus (SV40) promoter, a human or mouse ubiquitin C promoter, a human or mouse or rat elongation factor alpha (EF1-a) promoter, mouse or hamster beta-actin promoter, or a hamster rpS21 promoter. The Tet-Off and Tet-On elements upstream of a minimal promoter such as a CMV promoter forms an example of an inducible mammalian promoter. Examples of suitable yeast and fungal promoters are Leu2 promoter, the galactose (Gal1 or Gal7) promoter, alcohol dehydrogenase I (ADH1) promoter, glucoamylase (Gla) promoter, triose phosphate isomerase (TPI) promoter, translational elongation factor EF-I alpha (TEF2) promoter, glyceraldehyde-3-phosphate dehydrogenase (gpdA) promoter, alcohol oxidase (AOX1) promoter, or glutamate dehydrogenase (gdhA) promoter. An example of a strong ubiquitous promoter for expression in plants is cauliflower mosaic virus (CaMV) 35S promoter. Preferably, the nucleic acid construct of the invention comprises a heterologous promoter that is represented by a sequence that has at least 50%, 55%, 60%, 65%, 70%, 75%, 80%, 85%, 90%, 91%, 92%, 93%, 94%, 95%, 96%, 97%, 98%, 99% or 100% to SEQ ID NO: 58. More preferably, the nucleic acid construct of this aspect of the invention comprises a heterologous promoter that is represented by a sequence that has at least 50%, 55%, 60%, 65%, 70%, 75%, 80%, 85%, 90%, 91%, 92%, 93%, 94%, 95%, 96%, 97%, 98%, 99% or 100% to SEQ ID NO: 57.

In a further preferred embodiment within this aspect, the nucleic acid construct of the invention further comprises one or more additional expression regulating elements, wherein preferably said expression enhancing element, said heterologous promoter and said one or more additional expression regulating elements are configured to be all operably linked to an optional nucleotide sequence of interest as defined herein below. An "additional expression regulating element" is to be understood herein as an element in addition to the expression enhancing element and/or promoter as defined herein above which may be an additional expression enhancing element or a distinct expression enhancing element or an expression regulating element in its broadest sense.

An additional expression regulating element as encompassed by the present invention can be involved in the transcriptional and/or translational regulation of a gene, including but not limited to, 5'-UTR, 3'-UTR, enhancer, promoter, intronic sequence, polyadenylation signal and chromatin control elements such as scaffold/matrix attachment regions, ubiquitous chromatin opening element, cytosine phosphodiester guanine pairs and stabilizing and anti-repressor elements, and any derivatives thereof. Other optional regulating elements that may be present in the nucleic acid construct of the invention include, but are not limited to, coding nucleotide sequences of homologous and/or heterologous nucleotide sequences, including the Iron Responsive Element (IRE), Translational cis-Regulatory Element (TLRE) or uORFs in 5' UTRs and poly(U) stretches in 3' UTRs.

Preferably within this aspect, said additional expression regulating element comprises or consists of an intronic sequence as defined herein. Preferably, the intronic sequence encompassed within the additional expression regulating element comprises at least of an acceptor splice site which is understood herein as to comprise the splice site AG preferably preceded by a polypyrimidine tract nucleotide sequence, optionally separated from splice site AG by 1-50 nucleotides, and optionally further comprising a branch site comprising the sequence Y-T-N-A-Y, at the 5' site of the polypyrimidine tract nucleotide sequence, wherein the branch site may have the nucleotide sequence C-Y-G-A-C. An acceptor splice site is understood herein as a splice site that, when combined with a donor splice site encompassed within a construct, results in the formation of an intron as defined in the Definition section. Preferably, the acceptor splice site or splice site AG has the sequence [Y-rich]-N-Y-A-G-[cut]. Preferably, the acceptor splice site or splice site AG has the sequence [Y-rich]-N-Y-A-G-[cut]-R in case the host cell is a mammalian cell, [Y-rich]-D-Y-A-G-[cut]-R or [Y-rich]-D-Y-A-G-[cut]-R-W in case the host cell is a plant cell, [Y-rich]-A-Y-A-G-[cut] in case the host cell is a yeast cell and [Y-rich]-N-Y-A-G-[cut] in case the host cell is an insect cell. "[Y-rich]" is to be understood herein as a polypyrimidine tract which is preferably defined as a consecutive sequence of at least 10 nucleotides comprising at least 6, 7, 8, 9 or preferably 10 pyrimidine nucleotides. Preferably, said acceptor splice site or splice site GT has the sequence Y-A-G-[cut]-R. Preferably, said intronic sequence encompassed within said additional expression regulating element consists of said acceptor splice site or splice site AG. The intronic sequence preferably comprises or consists of a nucleotide sequence having at least 80%, 90%, 91%, 92%, 93%, 94%, 95%, 96%, 97%, 98%, 99% or 100% sequence identity to nucleotides 171-277 of SEQ ID NO: 14, nucleotides 171-274 of SEQ ID NO: 19, nucleotides 133-210 of SEQ ID NO: 20, nucleotides 134-211 of SEQ ID NO: 21, nucleotides 134-226 of SEQ ID NO: 22, nucleotides 134-226 of SEQ ID NO: 23, nucleotides 133-225 of SEQ ID NO: 24, nucleotides 134-226 of SEQ ID NO: 25, nucleotides 146-257 of SEQ ID NO: 26, or nucleotides 147-223 of SEQ ID NO: 27, or nucleotides 970-1449 of SEQ ID NO: 1 or nucleotides 667-1228 of SEQ ID NO: 2. Preferably, said intronic sequence comprised within said additional expression regulating element further comprises a donor splice site as defined herein. Even more preferred, said intronic sequence encompassed within the additional expression regulating element is a intron as defined in the Definition section. Most preferably, the intronic sequence encompassed within the additional expression regulating element comprises or consists of a nucleotide sequence having at least 80%, 90%, 91%, 92%, 93%, 94%, 95%, 96%, 97%, 98%, 99% or 100% sequence identity to nucleotides 171-277 of SEQ ID NO: 14, nucleotides 171-274 of SEQ ID NO: 19, nucleotides 133-210 of SEQ ID NO: 20, nucleotides 134-211 of SEQ ID NO: 21, nucleotides 134-226 of SEQ ID NO: 22, nucleotides 134-226 of SEQ ID NO: 23, nucleotides 133-225 of SEQ ID NO: 24, nucleotides 134-226 of SEQ ID NO: 25, nucleotides 146-257 of SEQ ID NO: 26, or nucleotides 147-223 of SEQ ID NO: 27.

Also preferred within this aspect is an expression regulating element that is a translation enhancing element. Preferably, a translation enhancing element allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that it is free of said translation enhancing element, preferably when tested in a system as exemplified in the Examples which are enclosed herein. More specifically, preferably the expression of nucleotide sequence of interest encoding for secreted alkaline phosphatase (SeAP) is measured in a mammalian cell system, most preferably in CHO cells, using a pcDNA3.1 expression vector comprising a translation enhancing element to be tested and a CMV promoter represented by SEQ ID NO: 57, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said translation enhancing element to be tested.

Preferably within this aspect, said translation enhancing element comprises or consists of a nucleotide sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 3-51 over its whole length. Preferably, said translation enhancing element comprises or consists of a nucleotide sequence that has at least 50%, 55%, 60%, 65%, 70%, 75%, 80%, 85%, 90%, 91%, 92%, 93%, 94%, 95%, 96%, 97%, 98%, 99% or 100 identity to SEQ ID NO: 19 over its whole length. More preferably, said translation enhancing element comprises or consists of a nucleotide sequence that has at least 90% identity to SEQ ID NO: 3-51 over its whole length. Also preferred within this aspect is a translation enhancing element that comprises or consists of a nucleotide sequence that comprises:

i) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides;

ii) a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said expression enhancing element not comprising a GAA repeat nucleotide sequence; or, iii) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence.

The GAA repeat nucleotide sequence, the TC-rich nucleotide sequence, the A-rich nucleotide sequence, the GT-rich nucleotide sequence have already been defined herein in the first aspect of the invention. These definitions also applied here.

Preferably within said aspect, said additional expression regulating element comprises a translation enhancing element as defined herein and an intronic sequence.

Preferably within said aspect, said additional expression regulating element is located within a nucleic acid construct of the invention downstream or the 3' site of a heterologous promoter. Preferably, said additional expression regulating element is located within a nucleic acid construct of the invention upstream or at the 5' site of a nucleic acid sequence encoding a protein or polypeptide of interest. Moreover, preferably a nucleic acid construct of the invention comprises the following nucleotide sequences indicated here in their relative positions in the 5' to 3' direction: (i) an expression enhancing element, (ii) a heterologous promoter, optionally (iii) an additional expression regulating element, and optionally (iv) a nucleotide sequence of interest, wherein preferably said expression enhancing element, said heterologous promoter and said additional expression regulating element are configured to be all operably linked to said optional nucleotide sequence of interest as defined herein below. It is to be understood that said expression enhancing element, said heterologous promoter, and optionally said additional expression regulating element of the nucleic acid construct of the invention are all configured to be operably linked to the same, single nucleotide sequence of interest.

The inventors found an unexpected synergistic effect when the expression enhancing element of the invention is combined with an additional expression regulating element as defined herein in an expression construct for expressing a protein or polypeptide of interest. In a stably transfected pool with both an expression enhancing element and an additional expression regulating element, the protein yield was significantly higher than the yield expected based on addition of the separate effects of either element. Preferably, said increase of protein or polypeptide expression is copy number independent as established by an assay suitable to determine copy number dependency by a skilled person, such as, but not limit to, a triplex Taqman assay as further detailed in Example 4 of the present invention. Preferably, said nucleic acid construct is a recombinant and/or isolated construct as defined herein. Preferably, said nucleic acid construct further comprises a nucleotide sequence of interest operably linked to and/or under the control of said expression enhancing element, said heterologous promoter and optionally said additional expression regulating element as defined herein. The presence of a nucleotide sequence of interest is optional. "Optional" is to be understood herein as not necessarily being present in an expression construct. For instance, such nucleotide sequence of interest need not be present in a commercialized expression vector, but may be readily introduced by a person skilled in the art before use in a method of the invention. It is to be understood that said expression enhancing element, said heterologous promoter, and optionally said additional expression regulating element are all configured to be operably linked to the same, single nucleotide sequence of interest. Preferably, said nucleic acid construct of the tenth aspect of the invention has at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% sequence identity to SEQ ID NO 73, 74, 75 or 76.

In a preferred embodiment within this aspect, said nucleotide sequence of interest is a nucleotide sequence encoding a protein or polypeptide of interest. The protein or polypeptide of interest can be a homologous protein or polypeptide, but in a preferred embodiment of the invention the protein or polypeptide of interest is a heterologous protein or polypeptide. A nucleotide sequence encoding a heterologous protein or polypeptide may be derived in whole or in part from any source known to the art, including a bacterial or viral genome or episome, eukaryotic nuclear or plasmid DNA, cDNA or chemically synthesised DNA. The nucleotide sequence encoding a protein or polypeptide of interest may constitute an uninterrupted coding region or it may include one or more introns bounded by appropriate splice junctions. It can further be composed of segments derived from different sources, naturally occurring or synthetic. The nucleotide sequence encoding the protein or polypeptide of interest according to the method of the invention is preferably a full-length nucleotide sequence, but can also be a functionally active part or other part of said full-length nucleotide sequence. The nucleotide sequence encoding the protein or polypeptide of interest may also comprise signal sequences directing the protein or polypeptide of interest when expressed to a specific location in the cell or tissue. Furthermore, the nucleotide sequence encoding the protein or polypeptide of interest can also comprise sequences which facilitate protein purification and protein detection by for instance Western blotting and ELISA (e.g. c-myc or polyhistidine sequences).

The protein or polypeptide of interest in this aspect has already been defined earlier herein in the first aspect of the invention.

In an alternative embodiment, said nucleotide sequence of interest is not a coding sequence for a protein or a polypeptide but may be a functional nucleotide sequence. This alternative embodiment of this aspect has already been defined earlier herein in the first aspect of the invention.

Twelfth Aspect

In a twelfth aspect, the present invention provides an expression vector comprising a nucleic acid construct according to the eleventh aspect of the invention. The expression vector of the invention preferably is a plasmid, cosmid or phage or nucleotide sequence, linear or circular, of a single or double stranded DNA or RNA, derived from any source, in which a number of nucleotide sequences have been joined or recombined into a unique construction which is capable of introducing any one of the nucleotide sequences of the invention in sense or antisense orientation into a cell. The choice of vector is dependent on the recombinant procedures followed and the host cell used. The vector may be an autonomously replicating vector or may replicate together with the chromosome into which it has been integrated. Preferably, the vector contains a selection marker. Useful markers are dependent on the host cell of choice and are well known to persons skilled in the art and are selected from, but not limited to, the selection markers as defined in third aspect of the invention. A preferred expression vector is the pcDNA3.1 expression vector. Preferred selection markers are the neomycin resistance gene, zeocin resistance gene and blasicidin resistance gene.

Thirteenth Aspect

In a thirteenth aspect, the present invention provides a cell comprising a nucleic acid molecule according to the tenth aspect of the invention, and/or a nucleic acid construct according to the eleventh aspect of the invention, and/or an expression vector according to the twelfth aspect of the invention as defined herein. The type of cell within the context of this aspect is the same as the one defined in the context of the third aspect.

Therefore, another aspect of the invention relates to a host cell that is genetically modified, preferably by a method of the invention, in that a host cell comprises a nucleic acid construct as defined above in the thirteenth aspect. For transformation procedures in plants, suitable bacteria include *Agrobacterium tumefaciens* and *Agrobacterium rhizogenes*.

A nucleic acid construct within the context of this thirteenth aspect is as the one of the third aspect: it is preferably stably maintained, either as an autonomously replicating element, or, more preferably, the nucleic acid construct is integrated into the host cell's genome, in which case the construct is usually integrated at random positions in the host cell's genome, for instance by non-homologous recombination. Stably transformed host cells are produced by known methods. The definition of the term stable transformation and methods encompassed for stable transformation have already been provided under the third aspect.

Alternatively, a protein or polypeptide of interest may be expressed in a host cell, e.g., a mammalian cell, relying on transient expression from vectors.

A nucleic acid construct according to this aspect preferably also comprises a marker gene which can provide selection or screening capability in a treated host cell.

All definitions relating to selectable markers and types of selectable markers including the example of the use of the luciferase gene as selectable marker, the example of a first category of marker based on a cell's metabolism and the use of a mutant cell line which lacks the ability to grow independent of a supplemented media, the example of dominant selection have already been provided in the third aspect. They also apply here in the thirteenth aspect of the invention.

When a transformed host cell is obtained with a method according to the invention (see below), a host tissue may be regenerated from said transformed cell in a suitable medium, which optionally may contain antibiotics or biocides known in the art for the selection of transformed cells.

Resulting transformed host tissues are preferably identified by means of selection using a selection marker gene as present on a nucleic acid construct as defined herein.

Fourteenth Aspect

In a fourteenth aspect, the present invention provides a method for expressing and optionally purifying a protein or polypeptide of interest comprising the step of:
a. providing a nucleic acid construct according to the eleventh aspect of the invention comprising a nucleotide sequence encoding a protein or polypeptide of interest; and,
b. contacting a cell with said nucleic acid construct to obtain a transformed cell; and,
c. allowing said transformed cell to express the protein or polypeptide of interest; and optionally,
d. purifying said protein or polypeptide of interest.

In a preferred embodiment of the method according to the invention, a nucleic acid construct as defined above in the eleventh aspect of the invention is used. The method of the invention may be an in vitro or ex vivo method. The method of the invention may be applied on a cell culture, organism culture, or tissue culture. Alternatively, next to the expression in host cells the protein or polypeptide of interest can be produced in cell-free translation systems using RNAs derived from the nucleic acid constructs of the present invention. The method of the invention may be performed on cultured cells.

The skilled person is capable of transforming cells in accordance with step b). Transformation methods as used in step b) include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to express the protein or polypeptide of interest, and optionally said protein or polypeptide is subsequently recovered. For example, the transformed cell may be subjected to conditions leading to expression of the protein or polypeptide of interest. The person skilled in the art is well aware of techniques to be used for expressing or overexpressing the protein or polypeptide of interest. Methods in which the transformed cell does not need to be subjected to specific conditions leading to expression of the protein or polypeptide of interest, but in which the protein or polypeptide of interest is automatically (e.g., constitutively) expressed, are also included in the method of the present invention.

Purification steps and definitions related to these steps as the definition of an isolated protein or polypeptide are the same as in the method of the fourth aspect and have been earlier defined herein. If desired as defined in the method of the fourth aspect, the nucleotide sequence encoding a protein or polypeptide of interest may be ligated to a heterologous nucleotide sequence to encode a fusion protein or polypeptide to facilitate protein purification and protein detection on for instance Western blot and in an ELISA. Suitable heterologous sequences include, but are not limited to, the nucleotide sequences coding for proteins such as for instance glutathione-S-transferase, maltose binding protein, metal-binding polyhistidine, green fluorescent protein, luciferase and beta-galactosidase. The protein or polypeptide may also be coupled to non-peptide carriers, tags or labels that facilitate tracing of the protein or polypeptide, both in vivo and in vitro, and allow for the identification and quantification of binding of the protein or polypeptide to substrates. Such labels, tags or carriers are well-known in the art and include, but are not limited to, biotin, radioactive labels and fluorescent labels.

Preferably, the method of this fourteenth aspect of the invention allows for an increase in expression of a protein or polypeptide of interest. Preferably, expression levels are established in an expression system using an expression construct according to the eleventh aspect of the invention comprising an expression enhancing element and a heterologous promoter operably linked to a nucleotide sequence encoding a protein or polypeptide of interest according to the eleventh aspect of the invention. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, the method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) that it is free of said expression enhancing element, preferably when tested in a system as exemplified in the Examples which are enclosed herein. More specifically, preferably the expression of nucleotide sequence of interest encoding for secreted alkaline phosphatase (SeAP) is measured in a mammalian cell system, most preferably in CHO cells, using a pcDNA3.1 expression vector comprising an expression enhancing element to be tested and a CMV promoter represented by SEQ ID NO: 57, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said expression enhancing element to be tested. Preferably, said increase of protein or polypeptide expression is copy number independent as established by an assay suitable to determine copy number dependency by a skilled person such as, but not limit to, a triplex Taqman assay as further detailed in Example 4 of the present invention.

Fifteenth Aspect

In a fifteenth aspect, the present invention provides a method for expressing a protein or polypeptide of interest in an organism, comprising the steps of:
a) providing a nucleic acid construct according to the eleventh aspect comprising a nucleotide sequence encoding a protein or polypeptide of interest of the invention; and,
b) contacting a target cell and/or target tissue of an organism, with said nucleic acid construct to obtain a transformed target cell and/or transformed target tissue, allowing said transformed cell to express the protein or polypeptide of interest; and optionally,
c) allowing said transformed target cell to develop into a transformed organism; and, optionally,
d) allowing said transformed organism to express the protein or polypeptide of interest, for example, subjecting said transformed organism to conditions leading to expression of the protein or polypeptide of interest, and optionally recovering said protein or polypeptide.

The target cell may be an embryonal target cell, e.g., embryonic stem cell, for example, derived from a non-human mammalian, such as bovine, porcine, etcetera species. Preferably, said target cell is not a human embryonic stem cell. In the case of a multicellular fungus, such target cell may be a fungal cell that can be proliferated into said multicellular fungus. When a transformed plant tissue or plant cell (e.g., pieces of leaf, stem segments, roots, but also protoplasts or plant cells cultivated by suspension) is obtained with this method according to the invention, whole plants can be regenerated from said transformed tissue or cell in a suitable medium, which optionally may contain antibiotics or biocides known in the art for the selection of transformed cells. This method of the invention may be applied in nucleic acid based vaccination and/or gene therapy preferably in a mammal, most preferably in a human. Encompassed within the present invention is a method of treatment comprising the method of the present aspect, wherein the protein or polypeptide of interest is a therapeutic and/or immunogenic protein or polypeptide. The invention also relates to a construct of the eleventh aspect of the invention for treatment, wherein the protein or polypeptide of interest is a therapeutic and/or immunogenic protein or polypeptide. Furthermore, the invention relates to the use of a construct of the eleventh aspect of the invention for the manufacture of a medicament, wherein the protein or polypeptide of interest is a therapeutic and/or immunogenic protein or polypeptide.

Furthermore, an embodiment of the invention is a non-human transformed organism. Said organism is transformed with a nucleotide sequence, recombinant nucleic acid construct, or vector according to the present invention, and is capable of producing the polypeptide of interest. This includes a non-human transgenic organism, such as a transgenic non-human mammalian, transgenic plant (including propagation, harvest and tissue material of said transgenic plant, including, but not limited to, leafs, roots, shoots and flowers), multicellular fungus, and the like.

Preferably, the method of this aspect of the invention allows for an increase in expression of a protein or polypeptide of interest in said organism or at least in one tissue or organelle or organ of said organism. Preferably, expression levels are established in an expression system using an expression construct according to the eleventh aspect of the invention comprising an expression enhancing element and a heterologous promoter operably linked to a nucleotide sequence encoding a protein or polypeptide of interest according to the eleventh aspect of the invention. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, this method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% A in said organism or at least in one tissue or organelle or organ of said organism. as compared to a method which only differs in that a construct is used in step a) that it is free of said expression enhancing element, preferably when tested in a system as exemplified in the Examples which are enclosed herein. More specifically, preferably the expression of nucleotide sequence of interest encoding for secreted alkaline phosphatase (SeAP) is measured in a mammalian cell system, most preferably in CHO cells, using a pcDNA3.1 expression vector comprising an expression enhancing element to be tested and a CMV promoter represented by SEQ ID NO: 57, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said expression enhancing element to be tested.

Preferably, said increase of protein or polypeptide expression is copy number independent as established by an assay suitable to determine copy number dependency by a skilled person such as, but not limit to, a triplex Taqman assay as further detailed in Example 4 of the present invention.

Sixteenth Aspect

In a sixteenth aspect, the present invention provides a method for transcription and optionally purifying the produced transcript comprising the step of:
a) providing a nucleic acid construct according to the eleventh aspect comprising a nucleotide sequence of interest of the invention; and,
b) contacting a cell with said nucleic acid construct to obtain a transformed cell; and,
c) allowing said transformed cell to produce a transcript of the nucleotide sequence of interest; and optionally,
d) purifying said produced transcript.

In a preferred embodiment of this method according to the invention a nucleic acid construct as defined above in the eleventh aspect is used. The method of the invention may be an in vitro or ex vivo method. The method of the invention may be applied on a cell culture, organism culture, or tissue culture. The method of the invention may be applied in nucleic acid based vaccination and/or gene therapy preferably in a mammal, preferably in a human. Encompassed within the present invention is a method for treatment comprising or consisting of the method of the present aspect, wherein the nucleotide sequence of interest encodes for a therapeutic transcript. The invention also relates to a construct of the eleventh aspect of the invention for use in treatment, wherein the nucleotide sequence of interest encodes for a therapeutic transcript. Furthermore, the invention relates to the use of a construct of the eleventh aspect of the invention for the manufacture of a medicament, wherein the nucleotide sequence of interest encodes for a therapeutic transcript.

The skilled person is capable of transforming cells in accordance with step b). Transformation methods as used in step b) include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to produce a transcript of the nucleotide sequence of interest, and optionally the produced transcript is subsequently recovered. For example, the transformed cell may be subjected to conditions leading to transcription the nucleotide sequence of interest. The person skilled in the art is well aware of techniques to be used for transcription the nucleotide sequence of interest. Methods in which the transformed cell does not need to be subjected to specific conditions leading to transcription of the nucleotide sequence of interest, but in which the nucleotide sequence of interest is automatically (e.g., constitutively) transcribed, are also included in the method of the present invention.

Purification steps depend on the transcript produced. The term "isolation" indicates that the transcript is found in a condition other than its native environment. In a preferred form, the isolated transcript is substantially free of other cellular components, particularly other homologous cellular components such as homologous proteins. It is preferred to provide the transcript in a greater than 40% pure form, more preferably greater than 60% pure form. Even more preferably it is preferred to provide the transcript in a highly purified form, i.e., greater than 80% pure, more preferably greater than 95% pure, and even more preferably greater than 99% pure, as determined by Northern blot.

Preferably, the method of this aspect of the invention allows for an increase in transcription of a nucleotide sequence of interest. Preferably, transcription levels are established in an expression system using an expression construct according to the second aspect of the invention comprising an expression enhancing element and a heterologous promoter operably linked to a nucleotide sequence of interest according to the second aspect of the invention. Preferably, transcription of said nucleotide sequence of interest is detected by a suitable assay such as RT-qPCR. Preferably, the method of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) that it is free of said expression enhancing element, preferably when tested in a system as exemplified in the Examples which are enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising an expression enhancing element to be tested and a CMV promoter represented by SEQ ID NO: 57, operably linked to said nucleotide sequence of interest. Transcription is preferably measured using RT-qPCR and transcription levels are compared to transcription levels of said nucleotide sequence of interest measured under the same conditions except that the expression vector used is free of said expression enhancing element to be tested.

Seventeenth Aspect

In an seventeenth aspect, the present invention provides a use of a nucleic acid molecule according to the tenth aspect of the invention, and/or a use of a nucleic acid construct according to the eleventh aspect of the invention, and/or a use of an expression vector according to the twelfth aspect of the invention, and/or a use of a cell according to the thirteenth aspect of the invention, for the transcription of a nucleotide sequence of interest and/or the expression of a protein or polypeptide of interest.

Eighteenth Aspect

In a eighteenth aspect, the present invention provides for a nucleic acid molecule according to according to the tenth aspect of the invention, and/or a nucleic acid construct according to the eleventh aspect of the invention, and/or an expression vector according to the twelfth aspect of the invention, and/or a cell according to the thirteenth aspect of the invention for use as a medicament. The invention also relates to a method of treatment comprising the administration of a nucleic acid molecule according to the tenth aspect of the invention, and/or a nucleic acid construct according to the eleventh aspect of the invention, and/or an expression vector according to the twelfth aspect of the invention, and/or a cell according to the thirteenth aspect of the invention, wherein preferably said administration is to a mammal, more preferably to a human. Preferably, said treatment is nucleic acid based vaccination and/or gene therapy preferably in a mammal, most preferably in a human. Furthermore, the invention relates to the use of a nucleic acid molecule according to according to the tenth aspect of the invention, and/or the use of a nucleic acid construct according to the eleventh aspect of the invention, and/or the use of an expression vector according to the twelfth aspect of the invention, and/or the use of a cell according to the thirteenth aspect of the invention, for the preparation of a medicament. Preferably said medicament is for nucleic acid based vaccination and/or gene therapy preferably in a mammal, most preferably in a human.

Nineteenth Aspect

In a nineteenth aspect, the present invention provides a nucleic acid molecule that is represented by a nucleotide sequence that has at least 50% identity with SEQ ID NO: 88 for increasing transcription of a nucleotide sequence of interest and/or expression of a protein or polypeptide of interest. Within the context of the nineteenth to twenty seventh aspect, said identity percentage is preferably assessed over the whole length of SEQ ID NO:88. However, it is not excluded that said identity percentage is assessed over part of SEQ ID NO:88 as defined in the section entitled definitions. Preferably, said nucleotide sequence of the invention is capable of increasing the transcription of a nucleotide sequence of interest and/or expression of a protein or polypeptide of interest. Said nucleic acid molecule represented by a nucleotide sequence that has at least 50% identity with SEQ ID NO:88 may be called a transcription regulating sequence.

Preferably within this aspect, transcription levels are established in an expression system using an expression construct comprising said nucleotide sequence operably linked to a nucleotide sequence of interest using a suitable assay such a RT-qPCR. Preferably, the nucleotide sequence of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% as compared to transcription levels using a construct wherein the nucleotide sequence having at least 50% identity with SEQ ID NO:88 has been replaced by an alternative sequence, preferably as exemplified in example 11 which is enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising the nucleotide sequence of the invention operably linked to said nucleotide sequence of interest. Transcription is preferably measured using RT-qPCR and transcription levels are compared to transcription levels of said nucleotide sequence of interest measured under the same conditions except that in the expression vector used the nucleotide sequence having at least 50% identity with SEQ ID NO:88 has been replaced by an alternative sequence, preferably as exemplified in example 11 which is enclosed herein.

Preferably within this aspect, expression levels are established in an expression system using an expression construct comprising said nucleotide sequence having at least 50% identity with SEQ ID NO:88 and which is operably linked to a nucleotide sequence encoding a protein or polypeptide of interest. Preferably, said protein or polypeptide of interest is a secreted protein or polypeptide and expression of said protein or polypeptide of interest is detected by a suitable assay such as an enzyme-linked immunosorbent assay (ELISA) assay, Western blotting or, dependent on the identity of the protein or polypeptide of interest, any suitable protein identification and/or quantification assay known to the person skilled in the art. Preferably, the nucleotide sequence having at least 50% identity with SEQ ID NO:88 allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that said nucleotide sequence has been replaced by an alternative sequence, preferably when tested in a system as exemplified in example 11 which is enclosed herein. More specifically, preferably the expression of a nucleotide sequence of interest encoding for secreted alkaline phosphatase (SeAP) is measured in a mammalian cell system, most preferably in CHO cells, using a pcDNA3.1 expression vector comprising a nucleotide sequence having at least 50% identity with SEQ ID NO:88 operably linked to said nucleotide sequence of interest. Expression is preferably measured by measuring the conversion of any suitable alkaline phosphatase substrate and expression levels are compared to expression levels of said isolated nucleic acid molecule as defined herein. In a preferred embodiment, said nucleotide sequence having at least 50% identity with SEQ ID NO:88 is a sequence that is derived from the UBC ubiquitin gene. Preferably, said nucleotide sequence is derived from a mammalian UBC ubiquitin gene. More preferably, said nucleotide sequence is derived from the *Cricetulus griseus* homologous gene of the human UBC ubiquitin gene, said gene being indicated as the *Cricetulus* sp. gene for polyubiquitin, or CRUPUQ (GenBank D63782).

In a preferred embodiment, said nucleotide sequence comprises or consists of a sequence that has at least 50%, 55%, 60%, 65%, 70%, 75%, 80%, 85%, 90%, 91%, 92%, 93%, 94%, 95%, 96%, 97%, 98%, 99% or 100% identity with SEQ ID NO: 88 over its whole length. Preferably, said sequence having at least 50%, 55%, 60%, 65%, 70%, 75%, 80%, 85%, 90%, 91%, 92%, 93%, 94%, 95%, 96%, 97%, 98%, 99% or 100% identity with SEQ ID NO: 88 over its whole length comprises a promoter as defined in the Definition section. Preferably, said promoter is capable of initiating transcription of a nucleotide sequence of interest and/or expression of a polypeptide or protein or polypeptide of interest encoded by a nucleotide sequence in a host cell as defined herein below. Preferably, said nucleotide sequence for increasing expression is a contiguous sequence of at least 1450, 1500, 1600, 1700, 1800, 1900, 2000, 2100, 2200, 2300, 2400, 2500, 2600 or 2617 in length, preferably at least 2617 nucleotides in length of SEQ ID NO: 88. Preferably, said nucleotide sequence having at least 50%, 51%, 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98%, 99% or 100% identity to SEQ ID NO: 88 is at most 8000 nucleotides in length. Preferably, said nucleotide sequence is at most 8000, 7000, 6000, 5000, 4000, 3000, 2617 in length. Most preferably, said sequence being 2617 nucleotides in length. Preferably, nucleotide sequence is at most 8000, 7000, 6000, 5000, 4000, 3000, 2617 nucleotides in length and has at least 50%, 55%, 60%, 65%, 70%, 75%, 80%, 85%, 90%, 95%, 99% identity to SEQ ID NO: 88 over its whole length.

Twentieth Aspect

In a twentieth aspect, the present invention provides a nucleic acid construct comprising a nucleic acid molecule according to the nineteenth aspect of the invention. A nucleic acid construct of the invention comprises a nucleotide sequence according to the nineteenth aspect of the present invention. Preferably, said nucleic acid construct is a recombinant and/or isolated construct as defined herein. Preferably, said nucleic acid construct further comprises an optional nucleotide sequence of interest as defined herein below wherein the nucleotide sequence of the invention is operably linked to said optional nucleic acid sequence of interest.

In a further preferred embodiment within this aspect, the nucleic acid construct of the invention further comprises one or more additional expression regulating elements, wherein preferably said nucleotide sequence and said one or more additional expression regulating elements are configured to be all operably linked to an optional nucleotide sequence of interest as defined herein below. An "additional expression regulating element" is to be understood herein as an element in addition to the nucleotide sequence as defined herein above which may be an additional expression regulating element or a distinct expression regulating element or an additional expression enhancing element or a distinct expression enhancing element. An additional expression regulating element as encompassed by the present invention can be involved in the transcriptional and/or translational regulation of a gene, including but not limited to, 5'-UTR, 3'-UTR, enhancer, intron, polyadenylation signal and chromatin control elements such as scaffold/matrix attachment regions, ubiquitous chromatin opening element, cytosine phosphodiester guanine pairs and stabilizing and anti-repressor elements, and any derivatives thereof. Other optional regulating elements that may be present in the nucleic acid construct of the invention include, but are not limited to, coding nucleotide sequences of homologous and/or heterologous nucleotide sequences, including the Iron Responsive Element (IRE), Translational cis-Regulatory Element (TLRE) or uORFs in 5' UTRs and poly(U) stretches in 3' UTRs.

Also preferred within this aspect is an expression regulating element that is a translation enhancing element. Preferably, a translation enhancing element allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to expression of said protein or polypeptide using a construct which only differs in that it is free of said translation enhancing element, preferably when tested in a system as exemplified in the Examples which are enclosed herein. More specifically, preferably the expression of nucleotide sequence of interest encoding for secreted alkaline phosphatase (SeAP) is measured in a mammalian cell system, most preferably in CHO cells, using a pcDNA3.1 expression vector comprising a translation enhancing element to be tested and a nucleotide sequence having at least 50% identity with SEQ ID NO: 88, operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that the expression vector is free of said translation enhancing element to be tested.

Preferably within this aspect, said translation enhancing element comprises or consists of a nucleotide sequence that has at least 50%, 55%, 60%, 65%, 70%, 75%, 80%, 85%, 90%, 91%, 92%, 93%, 94%, 95%, 96%, 97%, 98%, 99% or 100% identity to SEQ ID NO: 3-51 over its whole length. Preferably, said translation enhancing element comprises or consists of a nucleotide sequence that has at least 50%, 55%, 60%, 65%, 70%, 75%, 80%, 85%, 90%, 91%, 92%, 93%, 94%, 95%, 96%, 97%, 98%, 99% or 100 identity to SEQ ID NO: 19 over its whole length. More preferably, said translation enhancing element comprises or consists of a nucleotide sequence that has at least 90% identity to SEQ ID NO: 3-51 over its whole length. Also preferred within this aspect is a translation enhancing element that comprises or consists of a nucleotide sequence that comprises:
i) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides;
ii) a TC-rich nucleotide sequence comprising at least 8 consecutive C or T nucleotides, at least 3 A-rich nucleotide sequences comprising at least 5 consecutive A nucleotides, and a GT-rich nucleotide sequence comprising at least 10 nucleotides, at least 80% of which are G or T nucleotides, said expression enhancing element not comprising a GAA repeat nucleotide sequence; or,
iii) a GAA repeat nucleotide sequence, a TC-rich nucleotide sequence comprising at least 8 consecutive C or T nucleotides, at least 3 A-rich nucleotide sequences comprising at least 5 consecutive A nucleotides, a GT-rich nucleotide sequence comprising at least 10 nucleotides, at least 80% of which are G or T nucleotides, wherein said GAA repeat nucleotide sequence is located 3' of any one or more of said TC-rich nucleotide sequence, A-rich nucleotide sequences, and/or GT-rich nucleotide sequence.

The GAA repeat nucleotide sequence, the TC-rich nucleotide sequence, the A-rich nucleotide sequence, the GT-rich nucleotide sequence have already been defined herein in the first aspect of the invention. These definitions also applied here.

Preferably within said aspect, said additional expression regulating element is located within a nucleic acid construct of the invention having at least 50% identity with SEQ ID NO: 88. Preferably, said additional expression regulating element is located within a nucleic acid construct of the invention upstream or at the 5' site of a nucleic acid sequence encoding a protein or polypeptide of interest. Moreover, preferably a nucleic acid construct of the invention comprises the following nucleotide sequences indicated here in their relative positions in the 5' to 3' direction:
optionally (i) an expression regulating preferably enhancing element,
(ii) a nucleotide sequence having at least 50% identity with SEQ ID NO:88,
optionally (iii) an additional expression regulating element, and
optionally (iv) a nucleotide sequence of interest,
wherein preferably said expression enhancing element, said nucleotide sequence having at least 50% identity with SEQ ID NO:88 and said additional expression regulating element are configured to be all operably linked to said optional nucleotide sequence of interest as defined herein below. It is to be understood that said expression enhancing element, said nucleotide sequence having at least 50% identity with SEQ ID NO:88, and optionally said additional expression regulating element of the nucleic acid construct of the invention are all configured to be operably linked to the same, single nucleotide sequence of interest.

The presence of a nucleotide sequence of interest is optional. "Optional" is to be understood herein as not necessarily being present in an expression construct. For instance, such nucleotide sequence of interest need not be present in a commercialized expression vector, but may be readily introduced by a person skilled in the art before use in a method of the invention. It is to be understood that said expression enhancing element, said nucleotide sequence having at least 50% identity with SEQ ID NO:88, and optionally said additional expression regulating element are all configured to be operably linked to the same, single nucleotide sequence of interest.

In a preferred embodiment within this aspect, said nucleotide sequence of interest is a nucleotide sequence encoding a protein or polypeptide of interest. The protein or polypeptide of interest can be a homologous protein or polypeptide, but in a preferred embodiment of the invention the protein or polypeptide of interest is a heterologous protein or polypeptide. A nucleotide sequence encoding a heterologous protein or polypeptide may be derived in whole or in part from any source known to the art, including a bacterial or viral genome or episome, eukaryotic nuclear or plasmid DNA, cDNA or chemically synthesised DNA. The nucleotide sequence encoding a protein or polypeptide of interest may constitute an uninterrupted coding region or it may include one or more introns bounded by appropriate splice junctions. It can further be composed of segments derived from different sources, naturally occurring or synthetic. The nucleotide sequence encoding the protein or polypeptide of interest according to the method of the invention is preferably a full-length nucleotide sequence, but can also be a functionally active part or other part of said full-length nucleotide sequence. The nucleotide sequence encoding the protein or polypeptide of interest may also comprise signal sequences directing the protein or polypeptide of interest when expressed to a specific location in the cell or tissue. Furthermore, the nucleotide sequence encoding the protein or polypeptide of interest can also comprise sequences which facilitate protein purification and protein detection by for instance Western blotting and ELISA (e.g. c-myc or polyhistidine sequences).

The protein or polypeptide of interest in this aspect has already been defined earlier herein in the first aspect of the invention.

In an alternative embodiment, said nucleotide sequence of interest is not a coding sequence for a protein or a polypeptide but may be a functional nucleotide sequence. This alternative embodiment of this aspect has already been defined earlier herein in the first aspect of the invention.

Twenty First Aspect

In a twenty first aspect, the present invention provides an expression vector comprising a nucleic acid construct according to the twentieenth aspect of the invention. The expression vector of the invention preferably is a plasmid, cosmid or phage or nucleotide sequence, linear or circular, of a single or double stranded DNA or RNA, derived from any source, in which a number of nucleotide sequences have been joined or recombined into a unique construction which is capable of introducing any one of the nucleotide sequences of the invention in sense or antisense orientation into a cell. The choice of vector is dependent on the recombinant procedures followed and the host cell used. The vector may be an autonomously replicating vector or may replicate together with the chromosome into which it has been integrated. Preferably, the vector contains a selection marker. Useful markers are dependent on the host cell of choice and are well known to persons skilled in the art and are selected from, but not limited to, the selection markers as defined in third aspect of the invention. A preferred expression vector is the pcDNA3.1 expression vector. Preferred selection markers are the neomycin resistance gene, zeocin resistance gene and blasicidin resistance gene.

Twenty Second Aspect

In a twenty second aspect, the present invention provides a cell comprising a nucleic acid molecule according to the nineteenth aspect of the invention, and/or a nucleic acid construct according to the twentieth aspect of the invention, and/or an expression vector according to the twenty first aspect of the invention as defined herein. The type of cell within the context of this aspect is the same as the one defined in the context of the third aspect.

Therefore, another aspect of the invention relates to a host cell that is genetically modified, preferably by a method of the invention, in that a host cell comprises a nucleic acid construct as defined above in the twentieth aspect. For transformation procedures in plants, suitable bacteria include *Agrobacterium tumefaciens* and *Agrobacterium rhizogenes*.

A nucleic acid construct within the context of this twentieth aspect is as the one of the third aspect: it is preferably stably maintained, either as an autonomously replicating element, or, more preferably, the nucleic acid construct is integrated into the host cell's genome, in which case the construct is usually integrated at random positions in the host cell's genome, for instance by non-homologous recombination. Stably transformed host cells are produced by known methods. The definition of the term stable transformation and methods encompassed for stable transformation have already been provided under the third aspect.

Alternatively, a protein or polypeptide of interest may be expressed in a host cell, e.g., a mammalian cell, relying on transient expression from vectors.

A nucleic acid construct according to this aspect preferably also comprises a marker gene which can provide selection or screening capability in a treated host cell.

All definitions relating to selectable markers and types of selectable markers including the example of the use of the luciferase gene as selectable marker, the example of a first category of marker based on a cell's metabolism and the use of a mutant cell line which lacks the ability to grow independent of a supplemented media, the example of dominant selection have already been provided in the third aspect. They also apply here in the thirteenth aspect of the invention.

When a transformed host cell is obtained with a method according to the invention (see below), a host tissue may be regenerated from said transformed cell in a suitable medium, which optionally may contain antibiotics or biocides known in the art for the selection of transformed cells.

Resulting transformed host tissues are preferably identified by means of selection using a selection marker gene as present on a nucleic acid construct as defined herein.

Twenty Third Aspect

In a twenty third aspect, the present invention provides a method for expressing and optionally purifying a protein or polypeptide of interest comprising the step of:

a. providing a nucleic acid construct according to the twentieenth aspect of the invention comprising a nucleotide sequence encoding a protein or polypeptide of interest; and, b. contacting a cell with said nucleic acid construct to obtain a transformed cell; and, c. allowing said transformed cell to express the protein or polypeptide of interest; and optionally, d. purifying said protein or polypeptide of interest.

In a preferred embodiment of the method according to the invention, a nucleic acid construct as defined above in the twentieenth aspect of the invention is used. The method of the invention may be an in vitro or ex vivo method. The method of the invention may be applied on a cell culture, organism culture, or tissue culture. Alternatively, next to the expression in host cells the protein or polypeptide of interest can be produced in cell-free translation systems using RNAs derived from the nucleic acid constructs of the present invention. The method of the invention may be performed on cultured cells.

The skilled person is capable of transforming cells in accordance with step b). Transformation methods as used in step b) include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to express the protein or polypeptide of interest, and optionally said protein or polypeptide is subsequently recovered. For example, the transformed cell may be subjected to conditions leading to expression of the protein or polypeptide of interest. The person skilled in the art is well aware of techniques to be used for expressing or overexpressing the protein or polypeptide of interest. Methods in which the transformed cell does not need to be subjected to specific conditions leading to expression of the protein or polypeptide of interest, but in which the protein or polypeptide of interest is automatically (e.g., constitutively) expressed, are also included in the method of the present invention.

Purification steps and definitions related to these steps as the definition of an isolated protein or polypeptide are the same as in the method of the fourth aspect and have been earlier defined herein. If desired as defined in the method of the fourth aspect, the nucleotide sequence encoding a protein or polypeptide of interest may be ligated to a heterologous nucleotide sequence to encode a fusion protein or polypeptide to facilitate protein purification and protein detection on for instance Western blot and in an ELISA. Suitable heterologous sequences include, but are not limited to, the nucleotide sequences coding for proteins such as for instance glutathione-S-transferase, maltose binding protein, metal-binding polyhistidine, green fluorescent protein, luciferase and beta-galactosidase. The protein or polypeptide may also be coupled to non-peptide carriers, tags or labels that facilitate tracing of the protein or polypeptide, both in vivo and in vitro, and allow for the identification and quantification of binding of the protein or polypeptide to substrates. Such labels, tags or carriers are well-known in the art and include, but are not limited to, biotin, radioactive labels and fluorescent labels.

Preferably, the method of this twenty third aspect of the invention allows for an increase in expression of a protein or polypeptide of interest. Preferably, expression levels are established in an expression system using an expression construct according to the twenty first aspect of the invention comprising a nucleotide sequence having at least 50% identity with SEQ ID NO: 88 operably linked to a nucleotide sequence encoding a protein or polypeptide of interest Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, the method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) that in said construct the nucleotide sequence having at least 50% identity with SEQ ID NO:88 has been replaced by an alternative sequence, preferably one of those as described in example 11, more preferably when tested in a system as exemplified in example 11 which is enclosed herein. More specifically, preferably the expression of nucleotide sequence of interest encoding for secreted alkaline phosphatase (SeAP) is measured in a mammalian cell system, most preferably in CHO cells, using a pcDNA3.1 expression vector comprising a nucleotide sequence having at least 50% identity with SEQ ID NO:88 operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that in the expression vector the nucleotide sequence having at least 50% identity with SEQ ID NO:88 has been replaced by an alternative sequence, preferably one of those as described in example 11.

Twenty Fourth Aspect

In a twenty fourth aspect, the present invention provides a method for expressing a protein or polypeptide of interest in an organism, comprising the steps of:
a) providing a nucleic acid construct according to the twentieenth aspect comprising a nucleotide sequence encoding a protein or polypeptide of interest of the invention; and,
b) contacting a target cell and/or target tissue of an organism, with said nucleic acid construct to obtain a transformed target cell and/or transformed target tissue, allowing said transformed cell to express the protein or polypeptide of interest; and optionally,
c) allowing said transformed target cell to develop into a transformed organism; and, optionally,
d) allowing said transformed organism to express the protein or polypeptide of interest, for example, subjecting said transformed organism to conditions leading to expression of the protein or polypeptide of interest, and optionally recovering said protein or polypeptide.

The target cell may be an embryonal target cell, e.g., embryonic stem cell, for example, derived from a non-human mammalian, such as bovine, porcine, etcetera species. Preferably, said target cell is not a human embryonic stem cell. In the case of a multicellular fungus, such target cell may be a fungal cell that can be proliferated into said multicellular fungus. When a transformed plant tissue or plant cell (e.g., pieces of leaf, stem segments, roots, but also protoplasts or plant cells cultivated by suspension) is obtained with this method according to the invention, whole plants can be regenerated from said transformed tissue or cell in a suitable medium, which optionally may contain antibiotics or biocides known in the art for the selection of transformed cells. This method of the invention may be applied in nucleic acid based vaccination and/or gene therapy preferably in a mammal, most preferably in a human. Encompassed within the present invention is a method of treatment comprising the method of the present aspect, wherein the protein or polypeptide of interest is a therapeutic and/or immunogenic protein or polypeptide. The invention also relates to a construct of the twentieenth aspect of the invention for treatment, wherein the protein or polypeptide of interest is a therapeutic and/or immunogenic protein or polypeptide. Furthermore, the invention relates to the use of a construct of the twentieenth aspect of the invention for the manufacture of a medicament, wherein the protein or polypeptide of interest is a therapeutic and/or immunogenic protein or polypeptide.

Furthermore, an embodiment of the invention is a non-human transformed organism. Said organism is transformed with a nucleotide sequence, recombinant nucleic acid construct, or vector according to the present invention, and is capable of producing the polypeptide of interest. This includes a non-human transgenic organism, such as a transgenic non-human mammalian, transgenic plant (including propagation, harvest and tissue material of said transgenic plant, including, but not limited to, leafs, roots, shoots and flowers), multicellular fungus, and the like.

Preferably, the method of this aspect of the invention allows for an increase in expression of a protein or polypeptide of interest in said organism or at least in one tissue or organelle or organ of said organism. Preferably, expression levels are established in an expression system using an expression construct according to the twenty first aspect of the invention comprising a nucleotide sequence having at least 50% identity with SEQ ID NO:88 operably linked to a nucleotide sequence encoding a protein or polypeptide of interest. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Preferably, this method of the invention allows for an increase in protein or polypeptide expression of at least 5%, 10%, 15%, 20%, 30%, 40%, 50%, 60%, 70%, 80%, 90%, 100%, 200%, 300%, 500%, 1000%, 1500% or 2000% in said organism or at least in one tissue or organelle or organ of said organism. as compared to a method which only differs in that a construct is used in step a) wherein the nucleotide sequence having at least 50% identity with SEQ ID NO:88 has been replaced by an alternative sequence, preferably one of those as described in example 11, preferably when tested in a system as exemplified in example 11 which is enclosed herein. More specifically, preferably the expression of a nucleotide sequence of interest encoding for secreted alkaline phosphatase (SeAP) is measured in a mammalian cell system, most preferably in CHO cells, using a pcDNA3.1 expression vector comprising a nucleotide sequence having at least 50% identity with SEQ ID NO:88 operably linked to said nucleotide sequence of interest. Expression is preferably measured by measuring the conversion of any suitable alkaline phosphatase substrate and expression levels are compared to expression levels of said nucleotide sequence of interest which are measured under the same conditions except that in the expression vector said nucleotide sequence having at least 50% identity with SEQ ID NO:88 has been replaced by an alternative sequence, preferably one of those as described in example 11.

Twenty Fifth Aspect

In a twenty fifth aspect, the present invention provides a method for transcription and optionally purifying the produced transcript comprising the step of:
  a) providing a nucleic acid construct according to the twentieenth aspect comprising a nucleotide sequence of interest of the invention; and,
  b) contacting a cell with said nucleic acid construct to obtain a transformed cell; and,
  c) allowing said transformed cell to produce a transcript of the nucleotide sequence of interest; and optionally,
  d) purifying said produced transcript.

In a preferred embodiment of this method according to the invention a nucleic acid construct as defined above in the twentieenth aspect is used. The method of the invention may be an in vitro or ex vivo method. The method of the invention may be applied on a cell culture, organism culture, or tissue culture. The method of the invention may be applied in nucleic acid based vaccination and/or gene therapy preferably in a mammal, preferably in a human. Encompassed within the present invention is a method for treatment comprising or consisting of the method of the present aspect, wherein the nucleotide sequence of interest encodes for a therapeutic transcript. The invention also relates to a construct of the twentieenth aspect of the invention for use in treatment, wherein the nucleotide sequence of interest encodes for a therapeutic transcript. Furthermore, the invention relates to the use of a construct of the twentieenth aspect of the invention for the manufacture of a medicament, wherein the nucleotide sequence of interest encodes for a therapeutic transcript.

The skilled person is capable of transforming cells in accordance with step b). Transformation methods as used in step b) include, but are not limited to transfer of purified DNA via cationic lipid reagents and polyethyleneimide (PEI), calcium-phosphate co-precipitation, microparticle bombardment, electroporation of protoplasts and microinjection or use of silicon fibers to facilitate penetration and transfer of DNA into the host cell.

In step c) the transformed cell is allowed to produce a transcript of the nucleotide sequence of interest, and optionally the produced transcript is subsequently recovered. For example, the transformed cell may be subjected to conditions leading to transcription the nucleotide sequence of interest. The person skilled in the art is well aware of techniques to be used for transcription the nucleotide sequence of interest. Methods in which the transformed cell does not need to be subjected to specific conditions leading to transcription of the nucleotide sequence of interest, but in which the nucleotide sequence of interest is automatically (e.g., constitutively) transcribed, are also included in the method of the present invention.

Purification steps depend on the transcript produced. The term "isolation" indicates that the transcript is found in a condition other than its native environment. In a preferred form, the isolated transcript is substantially free of other cellular components, particularly other homologous cellular components such as homologous proteins. It is preferred to provide the transcript in a greater than 40% pure form, more preferably greater than 60% pure form. Even more preferably it is preferred to provide the transcript in a highly purified form, i.e., greater than 80% pure, more preferably greater than 95% pure, and even more preferably greater than 99% pure, as determined by Northern blot.

Preferably, the method of this aspect of the invention allows for an increase in transcription of a nucleotide sequence of interest. Preferably, transcription levels are established in an expression system using an expression construct according to the second aspect of the invention comprising a nucleotide sequence having at least 50% identity with SEQ ID NO:88 operably linked to a nucleotide sequence of interest. Preferably, transcription of said nucleotide sequence of interest is detected by a suitable assay such as RT-qPCR. Preferably, the method of the invention allows for an increase in transcription of at least 5%, 10%, 15%, 20%, 30%, 40%, 50%, 60%, 70%, 80%, 90%, 100%, 200%, 300%, 500%, 1000%, 1500% or 2000% as compared to a method which only differs in that a construct is used in step a) wherein said nucleotide sequence having at least 50% identity with SEQ ID NO:88 has been replaced by an alternative sequence, preferably one of those as described in example 11, preferably when tested in a system as exemplified in example 11 which is enclosed herein. More specifically, preferably the transcription of a nucleotide sequence of interest encoding for secreted alkaline phosphatase (SeAP) is measured in a mammalian cell system, most preferably in CHO cells, using a pcDNA3.1 expression vector comprising a nucleotide sequence having at least 50% identity with SEQ ID NO:88 operably linked to said nucleotide sequence of interest. Transcription is preferably measured using RT-qPCR and transcription levels are compared to transcription levels of said nucleotide sequence of interest measured under the same conditions except that in the expression vector used the nucleotide sequence having at least 50% identity with SEQ ID NO:88 has been replaced by an alternative sequence, preferably one of those as described in example 11.

Twenty Sixth Aspect

In an twenty sixth aspect, the present invention provides a use of a nucleic acid molecule according to the nineteenth aspect of the invention, and/or a use of a nucleic acid construct according to the twentieenth aspect of the invention, and/or a use of an expression vector according to the twenty first aspect of the invention, and/or a use of a cell according to the twenty second aspect of the invention, for the transcription of a nucleotide sequence of interest and/or the expression of a protein or polypeptide of interest.

Twenty Seven Aspect

In a twenty seven aspect, the present invention provides for a nucleic acid molecule according to according to the nineteenth aspect of the invention, and/or a nucleic acid construct according to the twentieth aspect of the invention, and/or an expression vector according to the twenty first aspect of the invention, and/or a cell according to the twenty second aspect of the invention for use as a medicament. The invention also relates to a method of treatment comprising the administration of a nucleic acid molecule according to the nineteenth aspect of the invention, and/or a nucleic acid construct according to the twentieth aspect of the invention, and/or an expression vector according to the twenty first aspect of the invention, and/or a cell according to the twenty second aspect of the invention, wherein preferably said administration is to a mammal, more preferably to a human. Preferably, said treatment is nucleic acid based vaccination and/or gene therapy preferably in a mammal, most preferably in a human. Furthermore, the invention relates to the use of a nucleic acid molecule according to according to the nineteenth aspect of the invention, and/or the use of a nucleic acid construct according to the twentieth aspect of the invention, and/or the use of an expression vector according to the twenty first aspect of the invention, and/or the use of a cell according to the twenty second aspect of the invention, for the preparation of a medicament. Preferably said medicament is for nucleic acid based vaccination and/or gene therapy preferably in a mammal, most preferably in a human.

DEFINITIONS

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. A nucleic acid of the invention is preferably modified as compared to its naturally occurring counterpart by comprising at least 1, 2, 3, 4, 5, 10, 20, 30 or 50 nucleotide mutations as compared to its naturally occurring counterpart. Preferably, a nucleic acid of the invention does not occur in nature. Nucleic acids of the invention can also include nucleotide analogs (e.g., BrdU), and nonphosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, ssRNA, dsRNA, non coding RNAs, hnRNA, premRNA, matured mRNA or any combination thereof. The terms "nucleic acid sequence" and "nucleotide sequence" as used herein are interchangeable, and have their usual meaning in the art. The term refers to a DNA or RNA molecule in single or double stranded form. An "isolated nucleic acid sequence" refers to a nucleic acid sequence which is no longer in the natural environment from which it was isolated. A nucleic acid molecule is represented by a nucleotide sequence. Furthermore, an element such as, but not limited to an expression enhancing element and a transcription regulating element, is represented by a nucleotide sequence.

A "recombinant construct" (or chimeric construct) refers to any nucleic acid sequence or molecule, which is not normally found in nature in a species, in particular a nucleic acid sequence, molecule or gene in which one or more parts of the nucleic acid sequence are present that are not associated with each other in nature. For example, a recombinant construct comprises a promoter that is not associated in nature with part or all of the transcribed region or with another regulating region comprised within said recombinant construct. The term "recombinant construct" is understood to include expression constructs in which a promoter or expression regulating sequence is operably linked to one or more sense sequences (e.g. coding sequences) or to an antisense (reverse complement of the sense strand) or inverted repeat sequence (sense and antisense, whereby the RNA transcript forms double stranded RNA upon transcription), or to any other sequence coding for a functional RNA molecule.

A "nucleic acid construct" is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or transcription of a nucleotide sequence of interest and/or the expression of a peptide or polypeptide of interest in a cell or in a subject A "vector" or "plasmid" is herein understood to mean a man-made (usually circular) nucleic acid molecule resulting from the use of recombinant DNA technology and which is used to deliver exogenous DNA into a host cell. Vectors usually comprise further genetic elements to facilitate their use in molecular cloning, such as e.g. selectable markers, multiple cloning sites and the like (see below). A nucleic acid construct may also be part of a recombinant viral vector for expression of a protein in a plant or plant cell (e.g. a vector derived from cauliflower mosaic virus, CaMV, or tobacco mosaic virus, TMV) or in a mammalian organism or mammalian cell system (e.g. a vector derived from Moloney murine leukemia virus (MMLV; a Retrovirus) a Lentivirus, an Adeno-associated virus (AAV) or an adenovirus (AdV)).

A "transformed cell" are terms referring to a new individual cell (or organism), arising as a result of the introduction into said cell of at least one nucleic acid molecule, especially comprising a chimeric or recombinant construct encoding a desired protein or a nucleic acid sequence which upon transcription yields an antisense RNA for silencing of a target gene/gene family. The host cell may be a plant cell, a bacterial cell (e.g. an *Agrobacterium* strain), a fungal cell (including a yeast cell), an animal (including insect, mammalian) cell, etc. The transformed cell may contain the nucleic acid construct as an extra-chromosomally (episomal) replicating molecule, as a non-replicating molecule or comprises the recombinant construct integrated in the nuclear or organellar DNA of the host cell. The term "organism" as used herein, encompasses all organisms consisting of more than one cell, i.e. multicellular organisms, and includes multicellular fungi.

"Transformation" and "transformed" refers to the transfer of a nucleic acid sequence, generally a nucleic acid sequence comprising a recombinant construct or gene of interest (GOT), into the nuclear genome of a cell to create a "transgenic" cell or organism comprising a transgene. The introduced nucleic acid sequence is generally, but not always, integrated in the host genome. When the introduced nucleic acid sequence is not integrated in the host genome, one may speak of "transfection", "transiently transfected", and "transfected". For the purposes of the present patent specification, the terms "transformation", "transiently transfected", and "transfection" are used interchangeably, and refer to stable or transient presence of a nucleic acid sequence into a cell or organism. When the cell is a bacterial cell, the term usually refers to an extrachromosomal, self-replicating vector which harbors a selectable antibiotic resistance.

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence indicated with a particular SEQ ID NO preferably means sequence identity over the entire length of said particular polypeptide or polynucleotide sequence indicated with said particular SEQ ID NO. However, sequence identity with a particular sequence indicated with a particular SEQ ID NO may also mean that sequence identity is assessed over a part of said SEQ ID NO. A part may mean at least 50%, 60%, 70%, 80%, 90% or 95% of the length of said SEQ ID NO. The sequence information as provided herein should not be so narrowly construed as to require inclusion of erroneously identified bases. The skilled person is capable of identifying such erroneously identified bases and knows how to correct for such errors.

Any nucleotide sequences capable of hybridising to the nucleotide sequences of the invention are defined as being part of the cis-acting elements of the invention. Stringent hybridisation conditions are herein defined as conditions that allow a nucleic acid sequence of at least 25, preferably 50, 75 or 100, and most preferably 150 or more nucleotides, to hybridise at a temperature of about 65° C. or of 65° C. in a solution comprising about 1 M salt or 1 M salt, preferably 6×SSC or any other solution having a comparable ionic strength, and washing at 65° C. in a solution comprising about 0.1 M salt, or 0.1 M salt or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity or at least 90% sequence identity. Moderate hybridization conditions are herein defined as conditions that allow a nucleic acid sequence of at least 50, preferably 150 or more nucleotides, to hybridise at a temperature of about 45° C. or of 45° C. in a solution comprising about 1 M salt or 1 M salt, preferably 6×SSC or any other solution having a comparable ionic strength, and washing at room temperature in a solution comprising about 1 M salt, or 1 M salt preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Identity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Preferred program and parameter for assessing identity for nucleic acid comparison is calculated using EMBOSS Needle Nucleotide Alignment algorithm with the following parameters: DNAfull matrix with the following gap penalties: open=10; extend=0.5 as carried out in example 9.

The term "derived from" in the context of being derived from a particular naturally occuring gene or sequence is defined herein as being chemically synthesized according to a naturally occuring gene or sequence and/or isolated and/or purified from a naturally occuring gene or sequence. Techniques for chemical synthesis, isolation and/or purification of nucleic acid molecules are well known in the art. In general, a derived sequence is a partial sequence of the naturally occuring gene or sequence or a fraction of the naturally occurring gene or sequence. Optionally, the derived sequence comprises nucleic acid substitutions or mutations, preferably resulting in a sequence being at least 50%, 55%, 60%, 65%, 70%, 75%, 80%, 85%, 90%, 91%, 92%, 93%, 94%, 95%, 96%, 97%, 98% or 99% identical over its whole length to the naturally occuring gene partial gene or sequence or partial sequence.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. A polypeptide is represented by an amino acid sequence. A polynucleotide is represented by a nucleotide sequence. A polypeptide is represented by an amino acid sequence.

The term "homologous" when used to indicate the relation between a given nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence of interest, preferably encoding a polypeptide will typically be operably linked to another promoter sequence or, if applicable, another secretory signal sequence and/or terminator sequence than in its natural environment.

When used to indicate the relatedness of two nucleic acid sequences the term "homologous" means that one single-stranded nucleic acid sequence may hybridise to a complementary single-stranded nucleic acid sequence. The degree of hybridisation may depend on a number of factors including the extent of identity between the sequences and the hybridisation conditions such as temperature and salt concentration as discussed later. Preferably, the region of identity is greater than 5 bp, more preferably the region of identity is greater than 10 bp.

The term "heterologous" when used to indicate the relation between a given (recombinant) nucleic acid or polypeptide molecule and a given host organism or host cell, is understood to mean a nucleic acid or polypeptide molecule from a foreign cell which does not occur naturally as part of the organism, cell, genome or DNA or RNA sequence in which it is present, or which is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced.

When used to indicate the relatedness of two nucleic acid sequences, the term the term "heterologous sequence" or "heterologous nucleic acid" is one that is not naturally found operably linked as neighboring sequence of the other sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

"Operably linked" is defined herein as a configuration in which a control sequence or regulating sequence is appropriately placed at a position relative to the nucleotide sequence of interest, preferably coding for the polypeptide of interest such that the control or regulating sequence directs or affects the transcription and/or production or expression of the nucleotide sequence of interest, preferably encoding a peptide or polypeptide of the invention in a cell and/or in a subject. For instance, a promoter is operably linked to a coding sequence if the promoter is able to initiate or regulate the transcription or expression of a coding sequence, in which case the coding sequence should be understood as being "under the control of" the promoter. When one or more nucleotide sequences and/or elements comprised within a construct are defined herein to be "configured to be operably linked to an optional nucleotide sequence of interest", said nucleotide sequences and/or elements are understood to be configured within said construct in such a way that these nucleotide sequences and/or elements are all operably linked to said nucleotide sequence of interest once said nucleotide sequence of interest is present in said construct.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. The term promoter refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter. The promoter does not include the transcription start site (TSS) but rather ends at nucleotide −1 of the transcription site, and does not include nucleotide sequences that become untranslated regions in the transcribed mRNA such as the 5'-UTR. Promoters of the invention may be tissue-specific, tissue-preferred, cell-type specific, inducible and constitutive promoters. Tissue-specific promoters are promoters which initiate transcription only in certain tissues and refer to a sequence of DNA that provides recognition signals for RNA polymerase and/or other factors required for transcription to begin, and/or for controlling expression of the coding sequence precisely within certain tissues or within certain cells of that tissue. Expression in a tissue-specific manner may be only in individual tissues or in combinations of tissues. Tissue-preferred promoters are promoters that preferentially initiate transcription in certain tissues. Cell-type-specific promoters are promoters that primarily drive expression in certain cell types. Inducible promoters are promoters that are capable of activating transcription of one or more DNA sequences or genes in response to an inducer. The DNA sequences or genes will not be transcribed when the inducer is absent. Activation of an inducible promoter is established by application of the inducer. Constitutive promoters are promoters that are active under many environmental conditions and in many different tissue types. Preferably, capability to initiate transcription is established in an expression system using an expression construct comprising said promoter operably linked to a nucleotide sequence of interest using a suitable assay such a RT-qPCR or Northern blotting. A promoter is said to be capable to start transcription if a transcript can be detected or if an increase in a transcript level is found of at least 5%, 10%, 15%, 20%, 30%, 40%, 50%, 60%, 70%, 80%, 90%, 100%, 200%, 300%, 500%, 1000%, 1500% or 2000% as compared to transcription using a construct which only differs in that it is free of said promoter. In a further preferred embodiment, capability to initiate expression is established in an expression system using an expression construct comprising said promoter operably linked to a nucleotide sequence encoding a protein or polypeptide of interest. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. A promoter is said to be capable to initiate expression if the protein or polypeptide of interest can be detected or if an increase in a expression level is found of at least 5%, 10%, 15%, 20%, 30%, 40%, 50%, 60%, 70%, 80%, 90%, 100%, 200%, 300%, 500%, 1000%, 1500% or 2000% as compared to expression using a construct which only differs in that it is free of said promoter. As a first and second promoter of the invention, an induced or constitutive promoter or a combination thereof may be used in the present invention.

An "intron" is a nucleotide sequence within a primary RNA transcript that is removed by RNA splicing or intron splicing while the final mature RNA product is being generated. Assessment whether intron splicing occurs can be done using any suitable method known to the person skilled in the art, such as but not limited to reverse-transcriptase polymerase chain reaction (RT-PCR) followed by size or sequence analysis of the RT-PCR product. Preferably, a nucleotide sequence is an intron if at least 2%, 5%, 10%, 15%, 20%, 30%, 40%, 50%, 60%, 70%, 80%, 90% or 100% of the primary RNA loses this sequence by RNA splicing using an assay suitable to detect intron splicing as indicated above. Preferably, an intron comprises a splice site GT at the 5' end of the nucleotide sequence, and a splice site AG at the 3' end of the nucleotide sequence, which splice site AG is preceded by a pyrimidine rich nucleotide sequence or polypyrimidine tract, optionally separated from splice site AG by 1-50 nucleotides. An intron may further comprise a branch site comprising the sequence Y-T-N-A-Y, at the 5' side of the polypyrimidine tract. The branch site may have the nucleotide sequence C-Y-G-A-C. An "intronic sequence" is understood to be at least part of the nucleotide sequence of an intron.

"Expression" will be understood to include any step involved in the production of the peptide or polypeptide including, but not limited to, transcription, post-transcriptional modification, translation, post-translational modification and secretion.

Optionally, a promoter represented by a nucleotide sequence present in a nucleic acid construct is operably linked to another nucleotide sequence encoding a peptide or polypeptide as identified herein.

An expression vector may be any vector which can be conveniently subjected to recombinant DNA procedures and can bring about the expression of a nucleotide sequence encoding a polypeptide of the invention in a cell and/or in a subject.

As used herein, the "5'-UTR" is the sequence starting with nucleotide 1 of the mRNA and ending with nucleotide −1 of the start codon. It is possible that a regulating part of the promoter is comprised within the nucleotide sequence becoming a 5'-UTR; however, in such case, the 5'-UTR is still not part of the promoter as herein defined.

The term "control sequences" is defined herein to include all components, which are necessary or advantageous for the expression of a polynucleotide or a polypeptide. Each control sequence may be native or foreign to the nucleic acid sequence harboring or encoding the polynucleotide or the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a host cell to terminate transcription. The terminator sequence is operably linked to the 3' terminus of the nucleic acid sequence of interest, preferably encoding a polypeptide of interest. Any terminator, which is functional in the cell, may be used in the present invention.

The control sequence may also be a suitable leader sequence, a non-translated region of a mRNA which is important for translation by the host cell. The leader sequence is operably linked to the 5' terminus of the nucleic acid sequence of interest, preferably encoding a polypeptide of interest. Any leader sequence, which is functional in the cell, may be used in the present invention.

The control sequence may also be a polyadenylation sequence, a sequence which is operably linked to the 3' terminus of the nucleic acid sequence and which, when transcribed, is recognized by the host cell as a signal to add adenine residues to transcribed mRNA. Any polyadenylation sequence, which is functional in the cell, may be used in the present invention.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

TABLE 1

| Sequence identification | |
|---|---|
| SEQ ID NO: | Description |
| 1 | Expression enhancing element 1 |
| 2 | Expression enhancing element 2 |
| 3 | UN1 |
| 4-13 | sequences derived from UN1 |
| 14 | UN2 |
| 15 | UN1dGAA |
| 16 | UN2dGAA |

TABLE 1-continued

Sequence identification

| SEQ ID NO: | Description |
| --- | --- |
| 17 | R3 |
| 18 | fUN1 |
| 19 | UN2-2 |
| 20 | UN2-3 |
| 21 | UN2-4 |
| 22 | UN2-5 |
| 23 | UN2-6 |
| 24 | UN2-7 |
| 25 | UN2-8 |
| 26 | UN2-9 |
| 27 | UN2-10 |
| 28 | UN1dGAA-2 |
| 29 | UN1dGAA-3 |
| 30 | UN1dGAA-4 |
| 31 | UN1dGAA-5 |
| 32 | UN1dGAA-6 |
| 33 | UN2dGAA-2 |
| 34 | UN2dGAA-3 |
| 35 | UN2dGAA-4 |
| 36 | UN1shuffle |
| 37 | UN1shuffle-2 |
| 38 | UN1shuffle-3 |
| 39 | UN1shuffle-4 |
| 40 | UN1shuffle-5 |
| 41 | UN1shuffle-6 |
| 42 | UN2shuffle-1 |
| 43 | UN2shuffle-2 |
| 44 | CAA1 |
| 45 | CAA2 |
| 46 | CAA3 |
| 47 | CAA4 |
| 48 | CAA5 |
| 49 | CAA6 |
| 50 | TATA1 |
| 51 | TATA2 |
| 52 | CMV promoter enhancer sequence |
| 53 | UBC enhancer region |
| 54 | CMV promoter enhancer sequence |
| 55 | construct |
| 56 | construct |
| 57 | CMV promoter sequence |
| 58 | Minimal CMV promoter sequence |
| 59 | EEE1-Xt |
| 60 | EEE1-80 |
| 61 | EEE1-60 |
| 62 | EEE1-50 |
| 63 | EEE1-SL |
| 64 | HC RACE primer |
| 65 | Light chain vector sequence |
| 66 | Heavy chain vector sequence |
| 67 | HuMab1 protein light chain |
| 68 | HuMab1 protein heavy |
| 69 | HuMab2 protein light chain |
| 70 | HuMab2 protein and heavy chain |
| 71 | pcDNA3.1(+) |
| 72 | SeAP protein |
| 73 | EEE1 + CMV + TEE |
| 74 | EEE1-Xt + CMV + TEE |
| 75 | EEE1-80 + CMV + TEE |
| 76 | EEE1-60 + CMV + TEE |
| 77 | pPNic384 |
| 78 | pPNic602 insert |
| 79 | EF1a promoter |
| 80 | EEE1-A1 |
| 81 | EEE1-A2 |
| 82 | EEE1-A3 |
| 83 | EEE1-B1 |
| 84 | EEE1-B2 |
| 85 | EEE1-B3 |
| 86 | EEE1-B4 |
| 87 | EEE1-B5 |
| 88 | Transcription regulating sequence |

FIGURES

FIG. 1. Schematic map of intronic promoter construct and different transcripts. The construct comprises 2 promoters. Transcription by Promoter 1 results in a primary transcript including the intron that contains the complete Promoter 2 sequence and is bordered by 5' and 3'-splice sites. After intron splicing, said primary transcript results in a mRNA without said intron (Transcript 1) encoding a "Gene". Transcription from Promoter 2 also results in a mRNA (Transcript 2) encoding the same "Gene".

FIG. 2. Schematic map of EEE1 (A) and EEE2 (B) elements showing some features of the UBC and CCT8 genes relevant to their promoter activity in a genomic context. Features include the predicted transcription start site (TSS), 5'-UTRs, exon and intron information.

Figure 3:
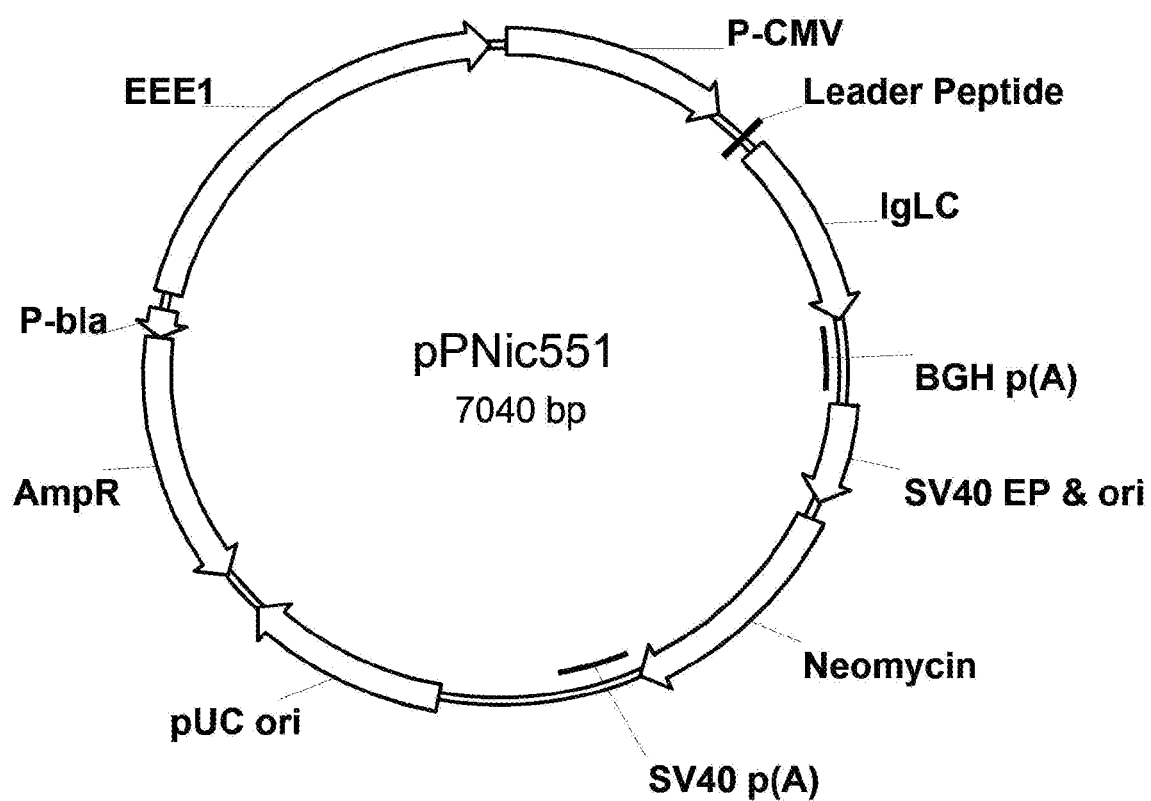

FIG. 3. Schematic map of an expression vector for an Ig light chain (IgLC) with the EEE1 sequence integrated upstream of the CMV promoter.

FIG. 4. Comparison of HuMab1 production by CHO-S pools stably transfected with Reference or EEE1 constructs. Expression vector without (A) and with (B) additional expression regulating element. The bars represent the average exhaust titers of 4 pools derived from 2 independent transfections. Pools were grown in 125 ml shake-flasks in 30 ml CD FortiCHO selection medium.

Figure 5:
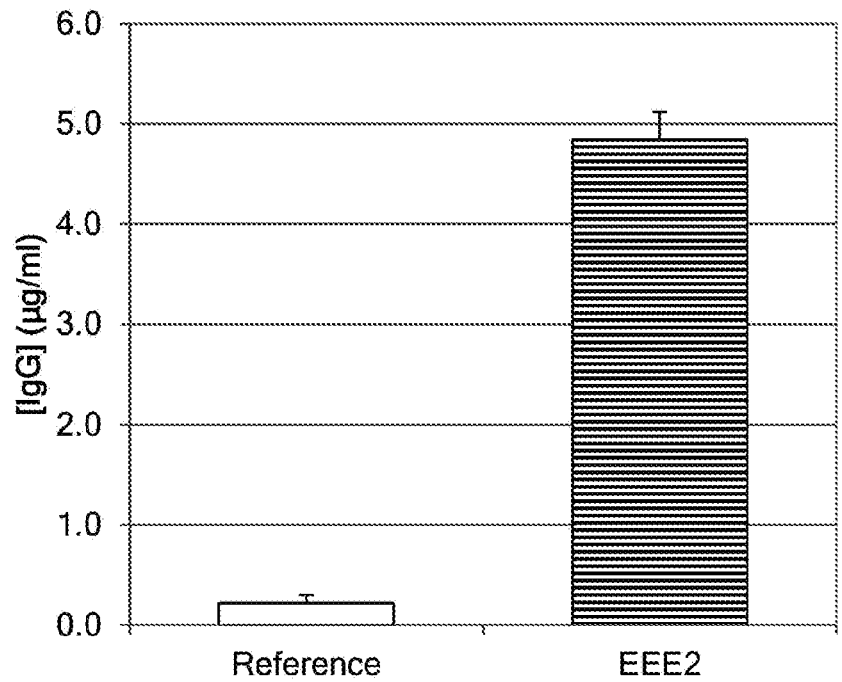

FIG. 5. Comparison of HuMab1 production by CHO-S pools stably transfected with Reference or EEE2 constructs. The bars represent the average exhaust titers of 4 pools derived from 2 independent transfections. Pools were grown in 125 ml shake-flasks in 30 ml CD FortiCHO selection medium.

Figure 6:
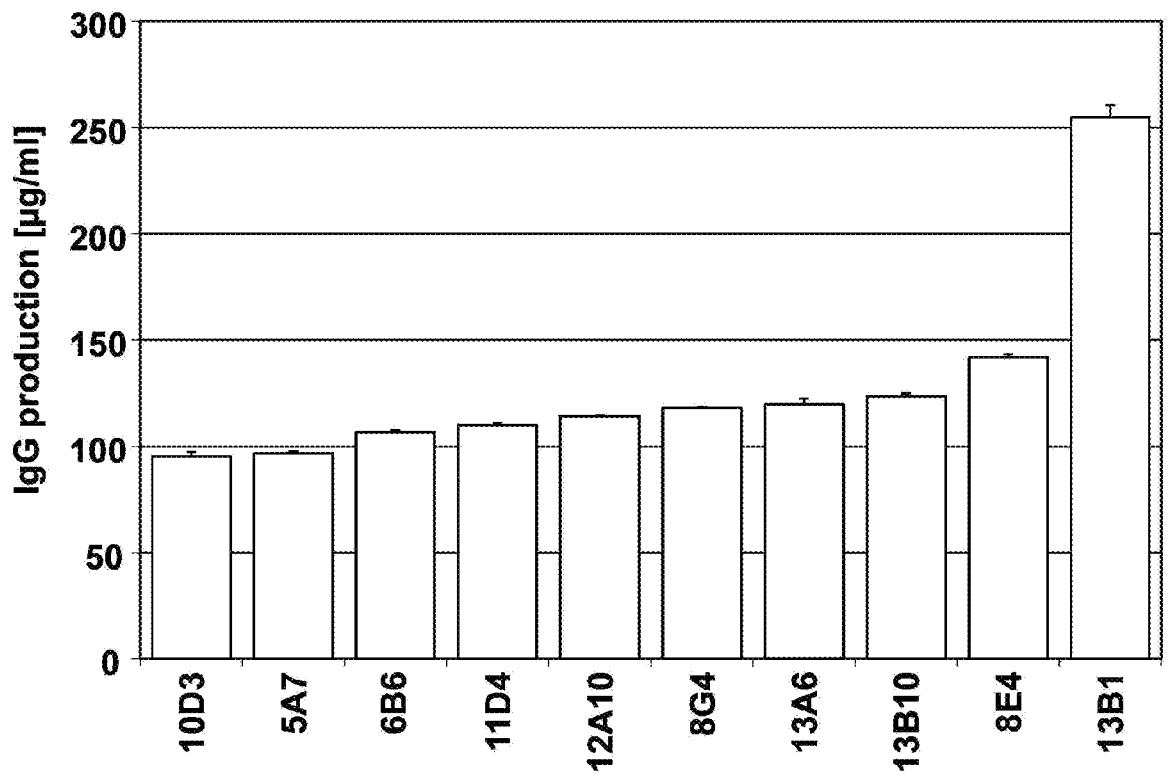

FIG. 6. Analysis of HuMab1 production by top-10 CHO-S clonal cell lines stably transfected with EEE1-TEE constructs harboring EEE1. Cells were grown in 125 ml shake-flasks in 30 ml CD FortiCHO selection medium.

FIG. 7. Comparison of HuMab2 production by CHO-S pools stably transfected with EEE1 in reference vector (A, left panel) and in vector with additional regulating element (A, right panel). The bars represent the average exhaust titers of 4 pools derived from 2 independent transfections. Pools were grown in 125 ml shake-flasks in 30 ml CD FortiCHO selection medium. (B) Analysis of HuMab2 production by top-12 Reference and EEE1-TEE CHO-S clonal cell lines. Cells were grown in 125 ml shake-flasks in 30 ml CD FortiCHO selection medium.

Figure 8:
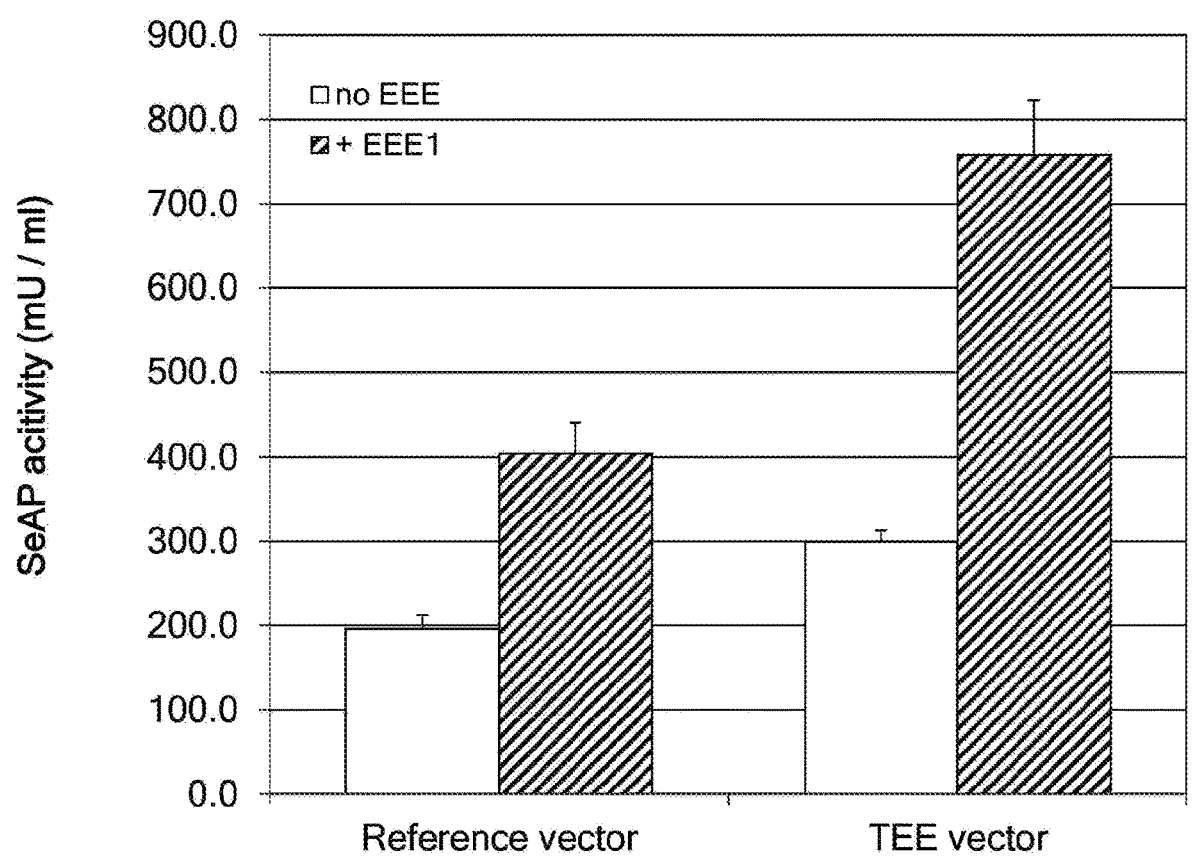

FIG. 8. Comparison of SeAP activity in the exhaust media of CHO-S pools stably transfected with Reference or EEE1 constructs. Expression vector without (left panel) and with (right panel) additional expression regulating element. The bars represent the average activities of 4 pools derived from 2 independent transfections, measured using the SEAP Reporter Gene Assay Kit, Abcam. Pools were grown in 125 ml shake-flasks in 30 ml CD FortiCHO selection medium.

Figure 9:
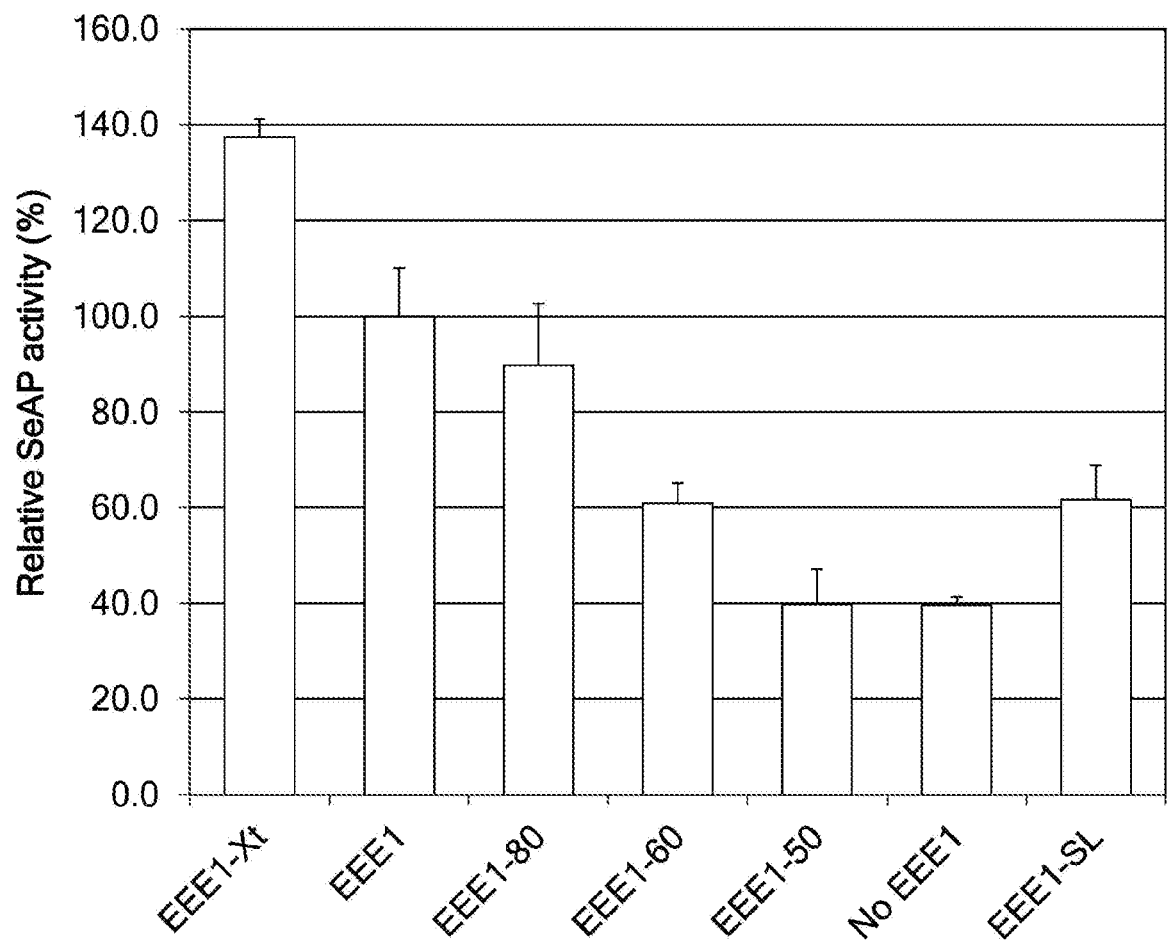

FIG. 9. Comparison of SeAP activity in the exhaust media of CHO-S pools stably transfected with constructs containing different versions of the EEE1 element. The bars represent the average activities of 4 pools derived from 2 independent transfections, measured using the SEAP Reporter Gene Assay Kit, Abcam. Pools were grown in 125 ml shake-flasks in 30 ml CD FortiCHO selection medium.

Figure 10A:
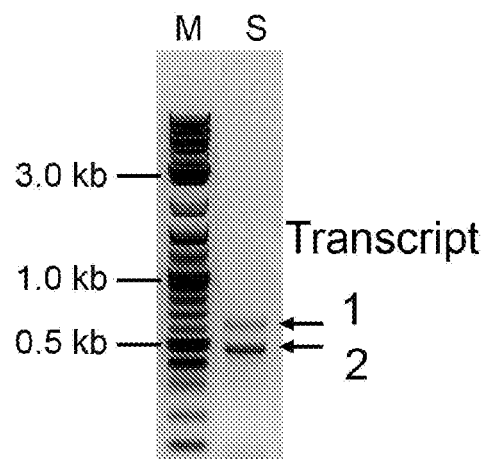

FIG. 10. 5'-RACE amplification of 5'-ends of heavy chain transcripts from CHO-S clones stably transfected with EEE1-TEE constructs expressing HuMab1 (A). Two bands are detected on agarose gel, corresponding to the transcripts generated by the CMV promoter (Transcript 1) and the UBC promoter (Transcript 2). The size difference between Transcript 1 and Transcript 2 is explained in a schematic map of intronic promoter construct and different transcripts (B). The construct comprises 2 promoters, UBC and CMV. The CMV promoter is linked to a TEE sequence which also comprises a short intron. Transcription by the CMV promoter results, after intron splicing, in mRNAs with TEE as 5'-UTR (Transcript 1). The UBC promoter is linked to a partial UBC 5'-UTR region which comprises a 5' splice donor site and precedes the CMV promoter. Transcription by the UBC promoter results in mRNAs with the UBC 5'-UTR sequence (Transcript 2). The large intron which is spliced from the primary transcript runs from the 5'-splice donor sequence in the UBC sequence to the 3'-splice acceptor site in the TEE and contains the complete CMV sequence.

Figure 11:
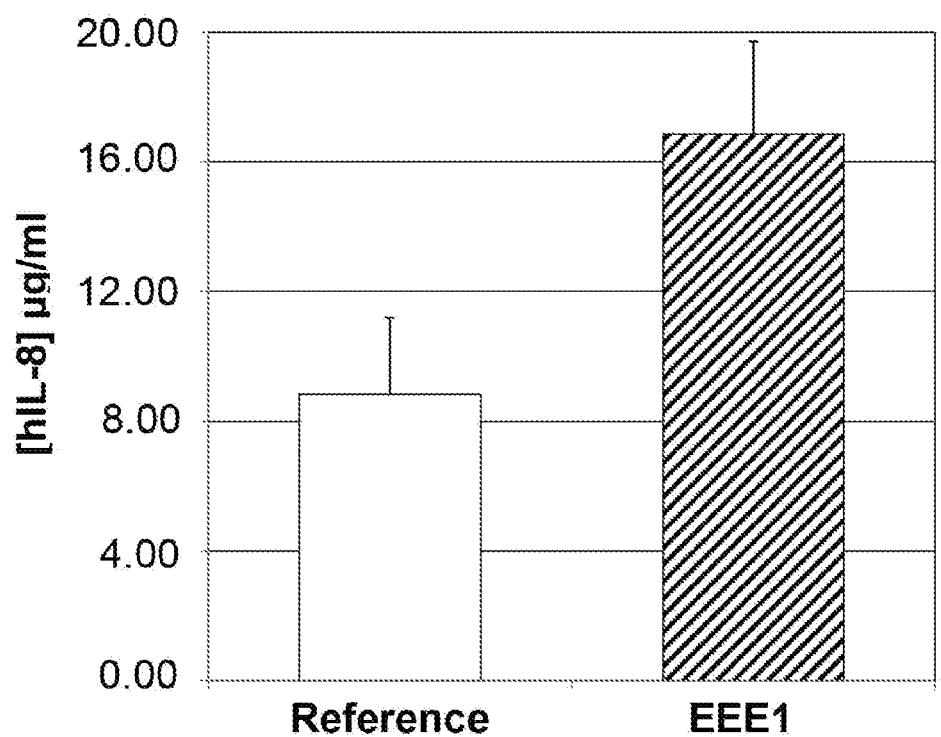

FIG. 11. Effect of EEE in *Pichia pastoris* expressing recombinant human interleukin 8. Each bar represents the average expression of 10 independent clones.

The invention will be explained in more detail in the following Examples section, with reference to the appended figures. The examples serve for illustration purposes only, and do not intend to limit the present invention in any way.

EXAMPLES

Figure 2A:
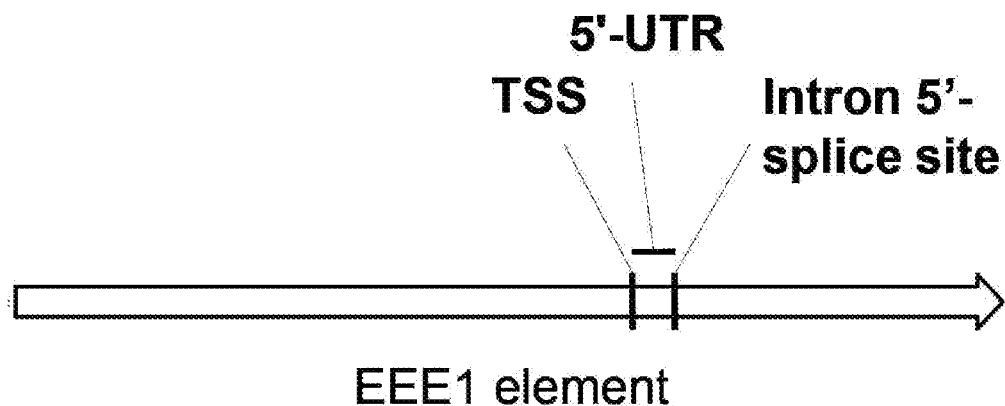
Figure 2B:
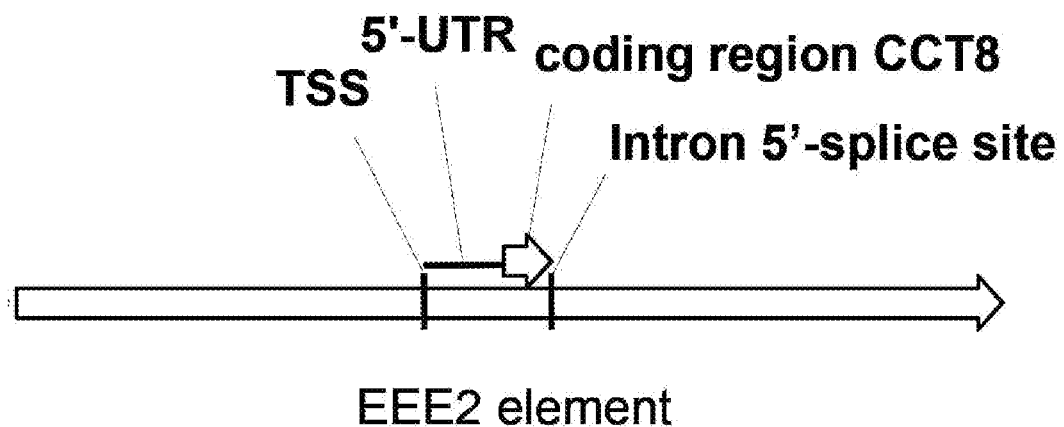

The expression enhancing element represented by SEQ ID NO: 1 is based on the Chinese hamster (*Cricetulus griseus*) ubiquitin-C (UBC) gene. It comprises the predicted promoter sequence and part of the 5'-untranslated region (FIG. 2A). The expression enhancing element represented by SEQ ID NO: 2 is based on the human CCT8 gene (chaperonin containing TCP1, subunit 8). It comprises the predicted promoter sequence and part of the 5'-untranslated region as well as a short sequence encoding 27 amino acids and part of the first intron (FIG. 2B).

Example 1

Expression plasmids were constructed based on the pcDNA3.1 expression vector (SEQ ID NO: 71). The vector was modified by removing the f1-ori. Coding sequences for an IgG1 (HuMab1) heavy (represented by a sequence that is at least 96% identical SEQ ID NO: 68) and light chain (represented by a sequence that is at least 99% identical SEQ ID NO: 67) genes were inserted in this vector (the light chain coding sequence was inserted in the vector represented by SEQ ID NO: 65 and the heavy chain coding sequence was inserted in the vector represented by SEQ ID NO: 66), resulting in the Reference constructs. To generate the EEE1 (Expression Enhancing Element 1) vectors, the EEE1-sequence (SEQ ID NO: 1) was inserted upstream of the CMV promoter (SEQ ID NO: 57) (FIG. 3). EEE2 (SEQ ID NO: 2) was introduced in a similar way, resulting in the EEE2 vectors. A vector with an additional expression regulating element was generated by replacing the pcDNA3.1 5'-UTR for SEQ ID NO: 19 (transcription enhancing element; TEE).

Figure 4A:
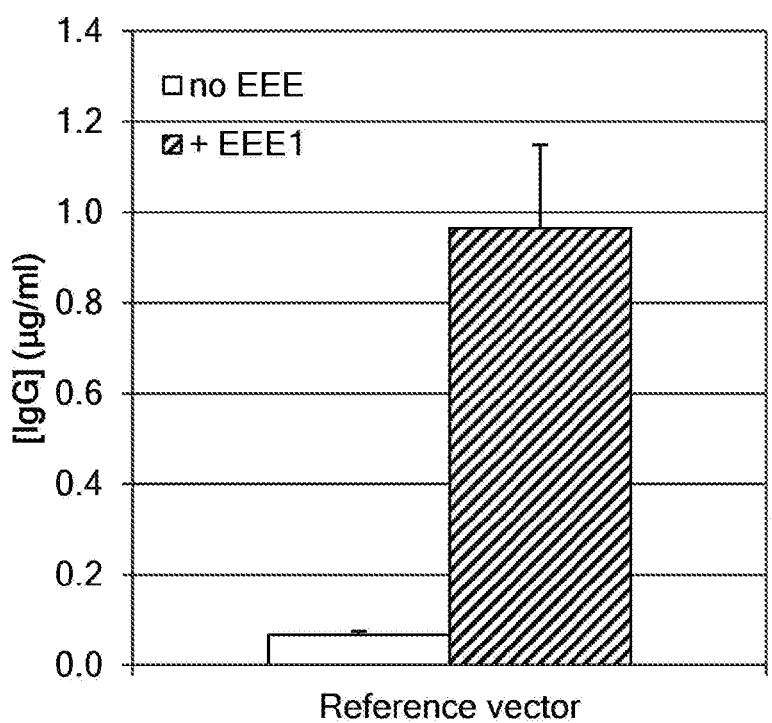
Figure 4B:
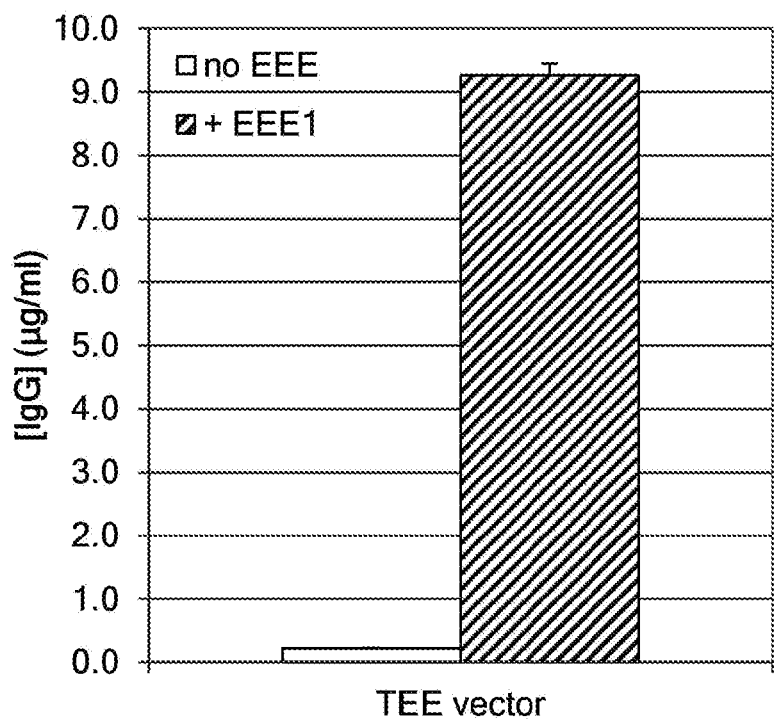

CHO-S cells (Life Technologies) were maintained per manufacturer's instructions. Duplicate transfections were performed using 3E7 cells, 50 µg of linearized DNA and FreeStyle MAX Reagent (Life Technologies). Post-transfection pools were split in two and selected in CD FortiCHO medium supplemented with 8 mM glutamine and 800 µg/ml G418. Selected pools were seeded in 30 ml of the same medium at a density of 3E5 cells/ml in 125 ml shake-flasks. The HuMab1 exhaust titers were determined by ELISA (FIG. 4). Exhaust titers of the Reference pools were too low for accurate determination. This indicates that the antibody is poorly expressed. The EEE1 pools produced approximately 1 µg/ml (FIG. 4A). A similar effect was observed in the vector with an additional expression regulating element. In this vector the introduction of EEE1 increased the production from approximately 0.2 µg/ml to 9-12 µg/ml in stable pools from three independent transfection experiments (FIG. 4B). These data show that a poorly expressed antibody can be expressed at significantly higher levels by introduction of the EEE1 element.

Example 2

The effect of introducing the EEE2 element was studied in a vector harboring an additional expression regulating element (See Example 1, FIG. 4B). CHO-S cells were transfected either with the reference or with the EEE2 constructs as described previously. Antibody exhaust titers of the stably transfected EEE2 pools were over 20 times higher than the Reference pools (FIG. 5).

Example 3

The EEE1-TEE and Reference pools generated previously were seeded in six 96-well plates at a density of 0.5 cell/well in CD FortiCHO selection medium. The Reference cells showed impaired growth as compared to the EEE1-TEE clones and thus no HuMab1 was produced. Clones of EEE1-TEE showed normal growth and HuMab1 production (See below). 100 Clonal EEE1-TEE lines were assessed for HuMab1 production in microtiter plates. The 10 clones with highest specific productivity were expanded to 125 ml shake-flasks. The clones were seeded in 30 ml of CD FortiCHO selection medium at a density of 3E5 cells/ml and HuMab1 exhaust titers were determined by ELISA (FIG. 6). Clones produced up to 0.25 µg/ml HuMab1. These data indicate that the EEE1 can facilitate the generation of clonal lines and allows the generation of clonal lines with relevant expression levels.

Example 4

The copy number of antibody expressing EEE comprising clones was determined. The PrimerExpress program (Life Technologies) was used to design Taqman primers and probes specific for the heavy- and light chains of HuMab1 and β-2 microglobulin. The primers were combined in a triplex Taqman assay to measure gene copies in gDNA samples of EEE1-TEE HuMab1 clones and pools. The gene copy numbers were compared with HuMab1 titers (Table 2). Clonal cell lines producing similar HuMab1 titers had different numbers of light and heavy chain gene copies (Clone 1 and 2). Also, clones producing very different HuMab1 titers had similar gene copy numbers (Clone 3 and 4). In pools relatively high numbers of light and heavy chain genes were paired with relatively low expression levels. These data (Table 2) indicate that there is no correlation between EEE comprising gene copy number and HuMab1 expression levels.

TABLE 2

Titers of IgG1 and gene copy numbers

|  | IgG titer | LC | HC |
| --- | --- | --- | --- |
| Clone 1 | 123.7 | 36.8 | 25.1 |
| Clone 2 | 118.2 | 1.7 | 1.7 |
| Clone 3 | 143.6 | 3.1 | 1.2 |

TABLE 2-continued

Titers of IgG1 and gene copy numbers

|  | IgG titer | LC | HC |
|---|---|---|---|
| Clone 4 | 7.2 | 4.6 | 0.7 |
| Pool | 9.0 | 17.5 | 21.1 |

Example 5

Figure 7A:
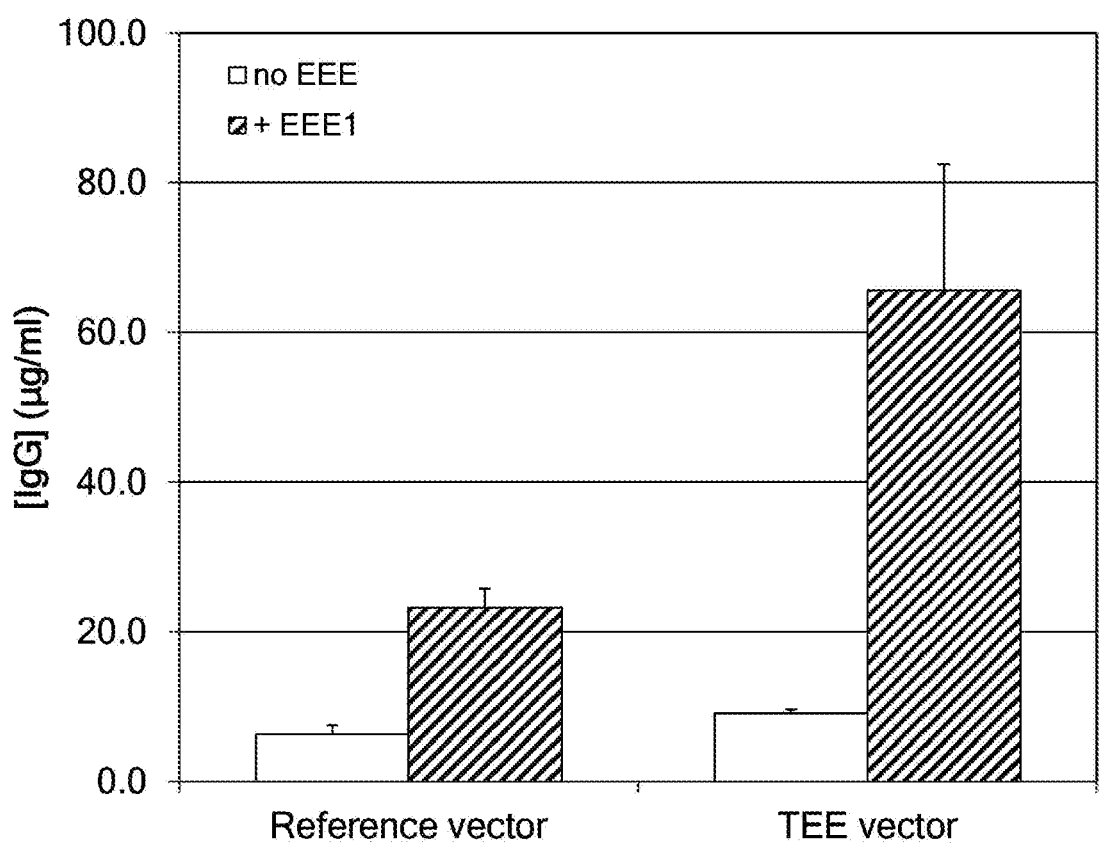
Figure 7B:
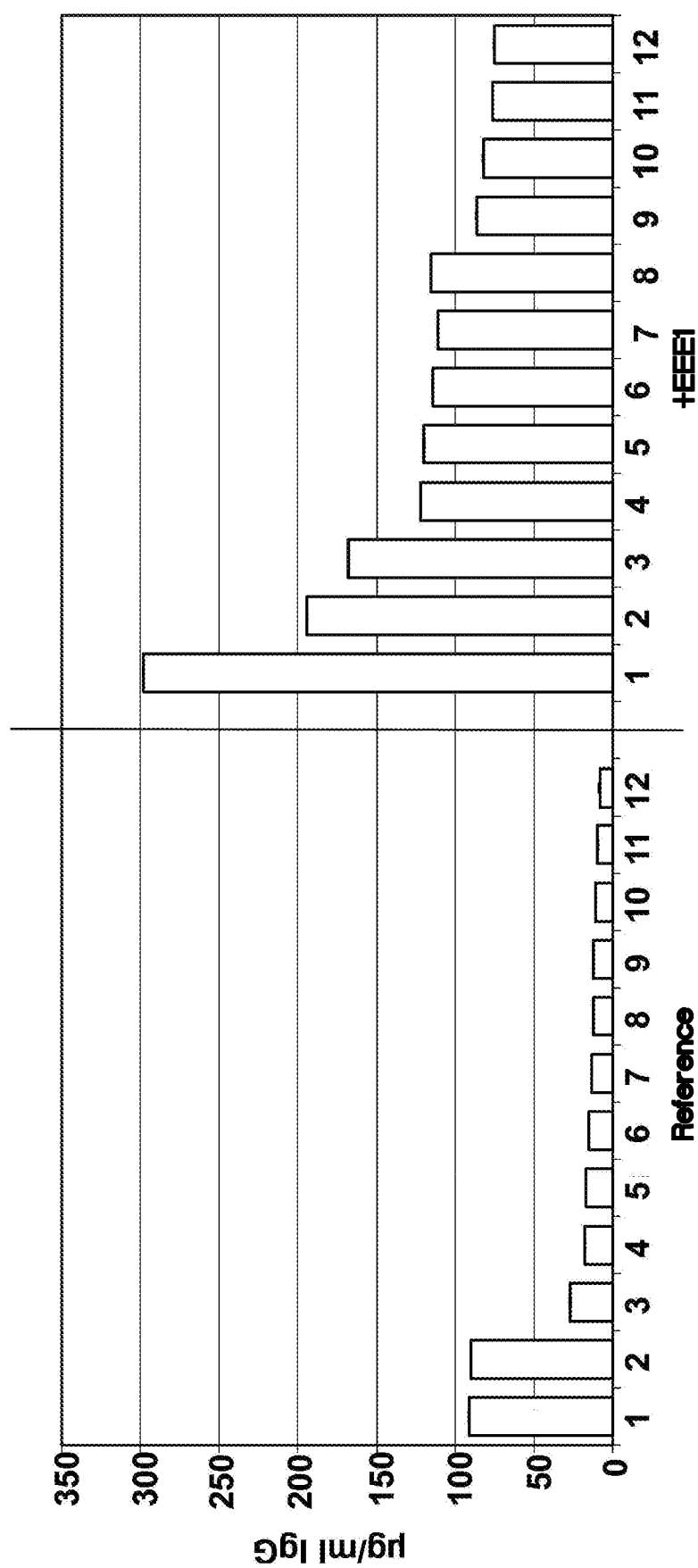

The HuMab1 heavy and light chain genes of the previous examples were replaced by heavy and light chain genes (SEQ ID NO's: 69 and 70) encoding a biosimilar antibody (HuMab2 derived from DrugBank Accession Number DB00072). The constructs were used to generate CHO-S pools as described previously. Using ELISA, the exhaust titers were determined. The data (6.3 μg/ml without enhancing element) indicate that this antibody is produced to a higher level than the antibody from the previous examples. Without any additional expression regulating element introduction of the EEE resulted in a 3.7 fold increase (FIG. 7A, left panel), in the modified vector the increase is 7 fold (FIG. 7A, right panel). Since stand-alone the additional expression regulating element results in a 40% increase, the data also indicate a synergistic effect between the EEE and the additional expression regulating element. Clonal lines were isolated from the Reference and EEE1-TEE pools as described previously. The best EEE1-TEE clones produced 3-fold higher HuMab2 titers as compared to the best Reference clones (FIG. 7B). These data indicate that the EEE1 element can be successfully applied in enhancing recombinant protein expression from stable cell lines.

Example 6

The HuMab1 light chain gene of the constructs from Example 1 was replaced by the gene encoding secreted alkaline phosphatase (SeAP; SEQ ID NO: 72). The constructs were used to generate CHO-S pools as described previously. The SeAP activity was measured in the exhaust medium using the SEAP Reporter Gene Assay Kit, Abcam. The EEE1 pools showed 2-fold higher activity as compared to the Reference pools (FIG. 8). In the EEE1-TEE pools the increase was almost 4-fold as compared to the Reference pool. These data show that EEE1 enhances the expression of a single subunit non-antibody protein in a transfected cell line.

Example 7

The SeAP constructs used in Example 6 all comprised the CMV promoter. Two TEE vector variants were made that contained the human EF-1α promoter instead of CMV (SEQ ID NO: 79). The constructs were used to generate CHO-S pools as described previously. The SeAP activity was measured in the exhaust medium using the SEAP Reporter Gene Assay Kit, Abcam. The EEE1-TEE pool with EF-1α as intronic promoter produced 2.8-fold higher SeAP activity as compared to the Reference EF-1α promoter pool without EEE1. These data show that EEE1 enhances the expression of a protein in an intronic promoter construct when the intronic promoter is not the CMV promoter, such as the EF-1α promoter.

Example 8

The EEE1 element of the EEE1 SeAP-expression vector was replaced by the following variants: 1. EEE1-80 represented by SEQ ID NO: 60 has a 290 bp truncation from the 5'-end; 2. EEE1-60 represented by SEQ ID NO: 61 with a 580 bp truncation from the 5'-end; 3. EEE1-50 represented by SEQ ID NO: 62 with a 725 bp truncation from the 5'-end; 4. EEE1-Xt represented by SEQ ID NO: 59 with a 800 bp extension from the genomic C. griseus UBC sequence at the 5'-end; 5. EEE1-SL (SEQ ID NO: 63) has all major predicted splice donor and acceptor sites mutated. SeAP activity in the supernatant of cells transfected with the EEE1 element was set at 100%, which decreased to 39% activity without the EEE1 element (FIG. 9). The 5' truncations of the EEE1-80 and EEE1-60 constructs gradually decreased activity but still showed enhanced activity as compared to the No-EEE construct. The EEE1-50 element decreased SeAP activity to 40%, which is similar to the No-EEE construct. The EEE1-Xt construct showed almost 40% increased activity as compared to the EEE1 construct. The data suggest that sequences with more than 50% identity to EEE1 can function as expression enhancing elements. The EEE1-Xt construct produced almost 40% increased activity as compared to the EEE1 construct, which shows that additional enhancer sequences reside in the region upstream of the genomic sequence from which EEE1 was taken. The activity of the EEE1 element is severely impaired by 4 nt mutations of the EEE1-SL construct which prevent correct intron splicing, resulting in a significant reduction in SeAP expression as compared to the EEE1 construct.

Example 9

The EEE1 element of the EEE1 SeAP-expression vector was replaced by 9 variants of the EEE1 element, which can be grouped based on 2 different types of mutations. The first type of EEE1 variants (EEE1-A) all had changes within the EEE1 or EEE1-Xt element with more than 30 percent of nucleotides mutated, each in another of the 3 regions which each consisted of at least 244 bp. The second type of EEE1 variants (EEE1-B) also had the same size as the EEE1 element (1,449 bp) with at least 96 percent sequence identity, with mutations that targeted different functional sequences of the EEE1 sequence. The different mutations are listed in Table 3.

TABLE 3

Modifications of EEE1

Type A: More than 30% mutated in 3 regions of EEE1

| Variant | SEQ ID NO: | Identity to EEE1[1] | Modified EEE1 region | Size modified region (bp) |
|---|---|---|---|---|
| EEE1-A1 | 80 | 71.6%[2] | 5' promoter region | 1,526 |
| EEE1-A2 | 81 | 95.0% | 3' promoter region | 244 |
| EEE1-A3 | 82 | 81.8% | intron region | 480 |

TABLE 3-continued

| Modifications of EEE1 | | | |
|---|---|---|---|
| Type B: Mutations that target specific domains of EEE1 | | | |
| Variant | SEQ ID NO: | Identity to EEE1[1)] | Modification of EEE1 sequence |
| EEE1-B1 | 83 | 97.9% | 1: 7 nt changed in nt 144-152<br>2: 4 nt changed in nt 612-615<br>3: 4 nt changed in nt 667-670<br>4: 6 nt changed in nt 816-823<br>5: 5 nt changed in nt 1,106-1,112<br>6: 5 nt changed in nt 1,432-1,438 |
| EEE1-B2 | 84 | 96.5% | 50 single bp mutations = 50% of CG's mutated in nt 227-1,409; predicted transcription factor binding sites maintained. |
| EEE1-B3 | 85 | 99.7% | 5 single bp mutations = 50% of CG's mutated in nt 549-603 |
| EEE1-B4 | 86 | 96.5% | 50 single bp mutations = 50% of CG's mutated in nt 227-1,409; 8 predicted sites for transcription factors SP1, HSF, and NFκB affected. |
| EEE1-B5 | 87 | 96.0% | 51 bp mutations in 12 regions with predicted transcription factor binding activity spanning nt 105-1,449 were mutated. |
| EEE1-B6[3)] | 63 | 99.7% | 4 single bp mutations eliminating predicted and known splice-donor or acceptor sites, including known donor site (nt 970), nt 545 and 552 in promoter region, nt 1,267 in intron region. |

[1)]Identity calculated using EMBOSS Needle Nucleotide Alignment algorithm with the following parameters: DNAfull matrix with the following gap penalties: open = 10; extend = 0.5
[2)]% identity EEE1-A1 calculated relative to EEE1-Xt
[3)]This is referred to as EEE1-SL in Example 8

Figure 10B:
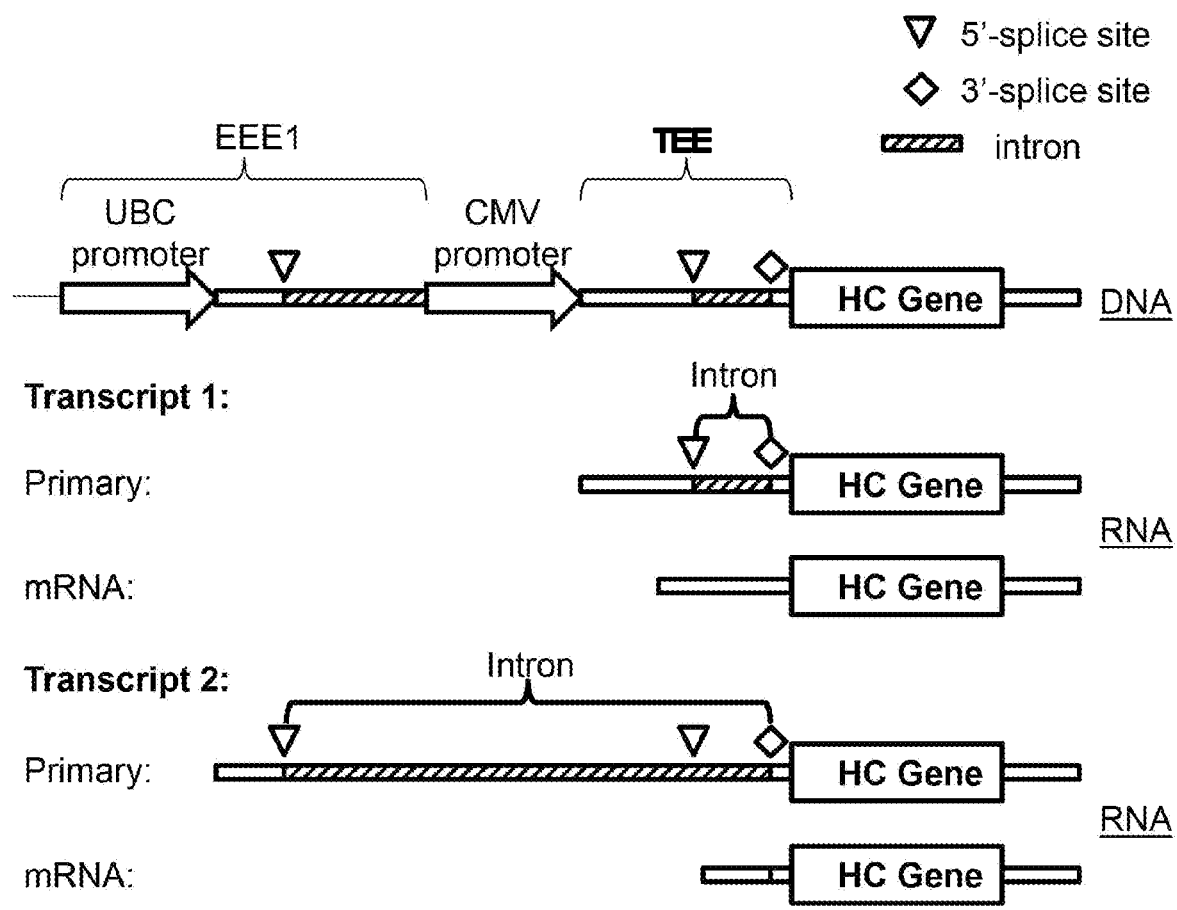

SeAP activity in the supernatant of cells transfected with the different variants was measured. Activity of cells with EEE1 element was used as reference (100%). Without EEE1 element the activity was 24% in this experiment. SeAP activity of cells transfected with the EEE1-A2 and EEE1-A3 constructs was decreased to 75% and 48% relative to EEE1, respectively (Table 4). This is higher than the 24% activity observed with the No-EEE construct in this experiment. The EEE1-A1 construct decreased SeAP activity to 30% relative to the EEE1-Xt construct on which it is based, which is still higher than the No-EEE construct which produces only 18% of SeAP activity relative to the EEE1-Xt construct. The data show that EEE1 variants with as little as 72% overall identity and locally 50% identity to the genomic UBC sequence can function as expression enhancing elements.

SeAP activity of cells transfected with the EEE1-B1 to B6 constructs was decreased by up to 42% relative to the EEE1 construct (Table 4). The data show that mutations in regions with a predicted functionality in the intronic promoter activity of the EEE1 element can significantly limit the expression enhancement capability of the EEE1 element. For instance, mutating 4 nt involved in intron-splicing resulted in 38% decreased SeAP titers (EEE1-B6). Mutation of different sets of CpG's also resulted in decreased SeAP titers (B1, B2, B4).

TABLE 4

| SeAP activity of EEE1 variants | |
|---|---|
| Construct | |
| | Activity relative to EEE1 (%)[1)] |
| No-EEE1 | 24 |
| EEE1 | 100 |
| EEE1-A2 | 75 |
| EEE1-A3 | 48 |
| EEE1-B1 | 58 |
| EEE1-B2 | 60 |
| EEE1-B3 | 73 |
| EEE1-B4 | 58 |
| EEE1-B5 | 84 |
| EEE1-B6 | 62 |
| | Activity relative to EEE1-Xt (%)[1)] |
| No-EEE1 | 18 |
| EEE1-Xt | 100 |
| EEE1-A1 | 30 |

TABLE 4-continued

[1)]Values represent the average activities of 4 pools derived from 2 independent transfections, measured using the SEAP Reporter Gene Assay Kit, Abcam. Pools were grown in 125 ml shake-flasks in 30 ml CD FortiCHO selection medium

Example 10

A EEE1-TEE CHO-S clone from Example 3 was grown and cells were harvested in log-phase. Total RNA was isolated from the cells using AllPrep DNA/RNA Mini Kit (Qiagen). cDNA was synthesized using the Epicentre Exact Start Eukaryotic mRNA 5' and 3' RACE Kit. First strand cDNA was amplified using the 5' RACE primer from the kit combined with a heavy chain specific primer (SEQ ID NO: 64) and ZymoTaq DNA polymerase. The PCR product was analyzed on 1.2% agarose gels, showing two discrete bands (FIG. 10A) which were separately isolated and inserted in a PCR4-TOPO vector (Life Technologies). Sequencing analysis revealed that the upper band seen on the agarose gel corresponds to the transcript initiated from the CMV promoter. The lower band corresponds to the transcript initiated from the UBC promoter. Both products have the predicted intronic sequence spliced out correctly. The differences in size correspond to the different lengths of the 5'-UTRs, as depicted in FIG. 10B. The data show that both promoters contribute to transcription.

Example 11

CHO-S pools stable transfected with constructs with three different single promoters were compared by the SeAP activity in the supernatant. Pools were grown in 125 ml shake-flasks in 30 ml CD FortiCHO selection medium and SeAP activity was measured using the SEAP Reporter Gene Assay Kit (Abcam) in 4 pools per construct derived from 2 independent transfections. The constructs either contained the CMV promoter (Example 6), the EF-1α promoter (Example 7), or the UBC promoter (Example 11). The UBC promoter produced 2.7-fold higher SeAP activity as compared to the CMV promoter construct. The UBC promoter produced 6.0-fold higher SeAP activity as compared to the EF-1α promoter. The data shows that the expression with the UBC promoter alone is higher as compared to the CMV promoter or the EF-1α promoter alone.

Example 12 Methanol Induced Secretion of IL8 in Pichia pastoris GS115 Integrative Transformants Plasmids for stable transformation of Pichia pastoris with human interleukin 8 (hIL-8) expression constructs were generated in plasmid pPIC9K (Life Technologies). Insertion of the hIL-8 gene in pPIC9K resulted in plasmid pPNic384 (SEQ ID NO: 77), which contains the hIL-8 gene under control of the AOX1 promoter. The EEE1 sequence was inserted upstream of the AOX1 promoter as a AatII-AleI fragment (SEQ ID NO: 78) in pPNic384, resulting in plasmid pPNic602.

The expression vectors were linearized by digestion with SalI and transformed into P. pastoris strain GS115 using electroporation as recommended (Invitrogen, 2008). Transformants were plated on RDB agar plates (Regeneration Dextrose Medium, a medium lacking histidine). After incubation at 30° C. for 48 h, large colonies were observed. A control transformation without DNA was performed resulting in no colonies. Randomly 10 clones per construct were picked from the transformation plate and grown to saturation in 800 µl BMG (Buffered minimal medium with 1% glycerol), in 2 ml deep well plates. The plate was kept in a shaking incubator (Infors-HT Microton) set at 30° C., 1000 rpm for 18 hours. The optical density of the culture was between 5-10 absorbance units at 600 nm. The cells were harvested and the medium replaced by 800 µl of BMM (Buffered minimal medium with 0.5% methanol) in 2 ml deep well plates. The cells were grown in the shaking incubator and every 24 hours 0.5% methanol (final concentration) was added to the culture to maintain induction. After 72 hours of methanol induction the culture supernatant were collected and assayed for secreted hIL8 yields using the AlphaLISA hIL8 kit (Perkin Elmer). The data show (FIG. 11) that there is a significant difference between the IL8 yields of the reference and the EEE1 transformants, suggesting that the EEE1 sequence upstream of the promoter improves the hIL8 yields compared to expression plasmid without the EEE1 sequence.

The invention claimed is:

1. A nucleic acid construct comprising a first promoter, a second promoter, and a single nucleotide sequence of interest, wherein said first promoter and second promoter are constitutive promoters and are both operably linked to said single nucleotide sequence of interest, and wherein said second promoter is an intronic promoter flanked by a first intronic sequence located upstream of said second promoter and a second intronic sequence located downstream of said second promoter, and wherein said single nucleotide sequence of interest is under the control of said first promoter and said second promoter, and wherein said first promoter and said first intronic sequence comprise the sequence of SEQ ID NO: 1 and said second intronic sequence comprises the sequence of SEQ ID NO: 19.

2. The nucleic acid construct according to claim 1, wherein said nucleic acid construct further comprises an additional expression regulating sequence, and wherein said additional expression regulating sequence, said first promoter and said second promoter are all operably linked to said nucleic acid sequence of interest.

3. The nucleic acid construct according to claim 1, wherein said nucleotide sequence of interest encodes a protein or polypeptide of interest.

4. An expression vector comprising the nucleic acid construct according to claim 1.

5. An in vitro cell comprising the nucleic acid construct according to claim 1.

6. A non-human cell comprising the nucleic acid construct according to claim 1.

7. The nucleic acid construct according to claim 2, wherein said additional expression regulating sequence comprises or consists of an intron.

8. The nucleic acid construct according to claim 3, wherein said protein or polypeptide of interest is a heterologous protein or polypeptide.

9. The nucleic acid construct according to claim 1, wherein said second promoter is a human or murine cytomegalovirus (CMV) promoter.

* * * * *